(12) United States Patent
Renfro et al.

(10) Patent No.: US 9,972,224 B2
(45) Date of Patent: *May 15, 2018

(54) FIBERS WITH MULTICOMPONENT FIBERS USED FOR CODING

(71) Applicant: Eastman Chemical Company, Kingsport, TN (US)

(72) Inventors: Larry Wayne Renfro, Kingsport, TN (US); Andrew Ervin McLeod, Jonesborough, TN (US); Humberto Collazo, Kingsport, TN (US); Ernest Phillip Smith, Blountville, TN (US)

(73) Assignee: Eastman Chemical Company, Kingsport, TN (US)

( * ) Notice: Subject to any disclaimer, the term of this patent is extended or adjusted under 35 U.S.C. 154(b) by 274 days.

This patent is subject to a terminal disclaimer.

(21) Appl. No.: 14/748,819

(22) Filed: Jun. 24, 2015

(65) Prior Publication Data

US 2015/0377792 A1 Dec. 31, 2015

Related U.S. Application Data

(60) Provisional application No. 62/164,135, filed on May 20, 2015, provisional application No. 62/018,182, (Continued)

(51) Int. Cl.
*G09F 3/00* (2006.01)
*G01N 21/84* (2006.01)
(Continued)

(52) U.S. Cl.
CPC ............ *G09F 3/0297* (2013.01); *A24D 3/00* (2013.01); *A24D 3/04* (2013.01); *A24D 3/063* (2013.01);
(Continued)

(58) Field of Classification Search
CPC .......... G09F 3/0297; A24D 3/00; A24D 3/04; A24D 3/063; A24D 3/10; D01D 5/082;
(Continued)

(56) References Cited

U.S. PATENT DOCUMENTS 1,822,098 A 9/1931 Huntress
4,280,925 A 7/1981 Kiefer
(Continued)

FOREIGN PATENT DOCUMENTS

CN 202298350 U 7/2012
WO WO 97/13896 A1 4/1997
(Continued)

OTHER PUBLICATIONS

Notification of Transmittal of the International Search Report and the Written Opinion of the International Searching Authority, or the Declaration dated Sep. 30, 2015 received in International Application No. PCT/US2015/037582.
(Continued)

*Primary Examiner* — Hezron E Williams
*Assistant Examiner* — Marrit Eyassu
(74) *Attorney, Agent, or Firm* — Dennis V. Carmen

(57) ABSTRACT

Disclosed are fibers which contains identification fibers. The identification fibers can contain a plurality of distinct features, or taggants, which vary among the fibers and/or along the length of the identification fibers of the fibers, a fiber band, or. The disclosed embodiments also relate to the method for making and characterizing the fibers. Characterization of the fibers can include identifying distinct features, combinations of distinct features, and number of fibers with various combinations of distinct features to supply chain information. The supply chain information can be used to
(Continued)

track the fibers, fiber band, or yarn from manufacturing through intermediaries, conversion to final product, and/or the consumer.

20 Claims, 17 Drawing Sheets

Related U.S. Application Data filed on Jun. 27, 2014, provisional application No. 62/105,011, filed on Jan. 19, 2015.

(51) Int. Cl.

| G01N 33/36 | (2006.01) |
| G06K 9/62 | (2006.01) |
| G06M 11/00 | (2006.01) |
| D01G 15/46 | (2006.01) |
| G06K 7/10 | (2006.01) |
| G06K 19/06 | (2006.01) |
| G09F 19/00 | (2006.01) |
| D06P 5/00 | (2006.01) |
| D01D 5/08 | (2006.01) |
| D06M 23/16 | (2006.01) |
| D01D 5/36 | (2006.01) |
| D01F 1/04 | (2006.01) |
| D01F 1/06 | (2006.01) |
| D01F 2/28 | (2006.01) |
| G07D 7/12 | (2016.01) |
| A24D 3/04 | (2006.01) |
| G07D 7/2033 | (2016.01) |
| A24D 3/06 | (2006.01) |
| A24D 3/10 | (2006.01) |
| G06K 7/14 | (2006.01) |
| A24D 3/00 | (2006.01) |
| D06P 5/30 | (2006.01) |
| D06M 101/20 | (2006.01) |
| D06M 101/32 | (2006.01) |
| D06M 101/34 | (2006.01) |

(52) U.S. Cl.
CPC .............. *A24D 3/10* (2013.01); *D01D 5/082* (2013.01); *D01D 5/36* (2013.01); *D01F 1/04* (2013.01); *D01F 1/06* (2013.01); *D01F 2/28* (2013.01); *D01G 15/46* (2013.01); *D06M 23/16* (2013.01); *D06P 5/00* (2013.01); *G01N 21/84* (2013.01); *G01N 33/365* (2013.01); *G06K 7/10* (2013.01); *G06K 7/1413* (2013.01); *G06K 9/62* (2013.01); *G06K 9/6217* (2013.01); *G06K 19/06046* (2013.01); *G06M 11/00* (2013.01); *G07D 7/12* (2013.01); *G07D 7/2033* (2013.01); *G09F 19/00* (2013.01); *D06M 2101/20* (2013.01); *D06M 2101/32* (2013.01); *D06M 2101/34* (2013.01); *D06P 5/30* (2013.01); *G01N 2021/8444* (2013.01); *G06K 2007/10504* (2013.01)

(58) Field of Classification Search
CPC .... D01D 5/36; D01F 1/04; D01F 1/06; D01F 2/28; D01G 15/46; D06M 23/16; D06P 5/00; G01N 21/84; G01N 33/365; G06K 7/10; G06K 7/1413; G06K 9/62; G06K 9/6217; G06K 19/06046; G06M 11/00
USPC ......................................................... 73/159
See application file for complete search history.

(56) References Cited

U.S. PATENT DOCUMENTS

| 4,496,619 | A | | 1/1985 | Okamoto | |
| 4,640,035 | A | * | 2/1987 | Kind | G09F 3/00 149/123 |
| 4,756,557 | A | | 7/1988 | Kaule et al. | |
| 5,167,764 | A | | 12/1992 | Nielsen et al. | |
| 5,344,297 | A | | 9/1994 | Hills | |
| 5,540,994 | A | | 7/1996 | Hernandez | |
| 5,876,650 | A | | 3/1999 | Burlone et al. | |
| 6,746,766 | B2 | | 6/2004 | Bond et al. | |
| 6,887,701 | B2 | | 5/2005 | Anderson et al. | |
| 6,964,931 | B2 | | 11/2005 | Carlyle et al. | |
| 7,122,248 | B2 | | 10/2006 | Tam et al. | |
| 7,128,848 | B2 | | 10/2006 | Pourdeyhimi et al. | |
| 7,163,744 | B2 | | 1/2007 | Nightingale et al. | |
| 7,244,497 | B2 | | 7/2007 | Hartmann et al. | |
| 7,338,877 | B1 | | 3/2008 | Meyer et al. | |
| 7,357,986 | B2 | | 4/2008 | Tam et al. | |
| 7,531,235 | B2 | | 5/2009 | Den Toonder et al. | |
| 7,684,652 | B2 | | 3/2010 | Zorab et al. | |
| 7,851,391 | B2 | | 12/2010 | Bond et al. | |
| 7,892,642 | B2 | | 2/2011 | Van Malderen | |
| RE42,188 | E | | 3/2011 | Tam et al. | |
| 7,995,196 | B1 | * | 8/2011 | Fraser | G06K 9/00577 356/71 |
| 8,137,811 | B2 | | 3/2012 | Merchant et al. | |
| 8,171,567 | B1 | * | 5/2012 | Fraser | G06T 1/0021 713/176 |
| 8,177,938 | B2 | | 5/2012 | Sumnicht | |
| 8,338,800 | B2 | | 12/2012 | Bortz et al. | |
| 8,375,958 | B2 | | 2/2013 | Hutchens | |
| 8,862,264 | B2 | | 10/2014 | Phan et al. | |
| 2002/0063364 | A1 | | 5/2002 | Taylor et al. | |
| 2002/0160188 | A1 | | 10/2002 | Tam et al. | |
| 2003/0006324 | A1 | | 1/2003 | Pettigrew et al. | |
| 2003/0058990 | A1 | * | 3/2003 | Kaiser | G01N 23/223 378/45 |
| 2004/0034214 | A1 | | 2/2004 | Nightingale et al. | |
| 2005/0227068 | A1 | * | 10/2005 | Dugan | D01D 5/36 428/364 |
| 2005/0227563 | A1 | | 10/2005 | Bond | |
| 2007/0243234 | A1 | | 10/2007 | Gabriele et al. | |
| 2010/0029158 | A1 | | 2/2010 | Kamiyama et al. | |
| 2010/0062251 | A1 | | 3/2010 | Merchant et al. | |
| 2010/0063208 | A1 | | 3/2010 | Merchant et al. | |
| 2010/0149531 | A1 | * | 6/2010 | Tang | G01J 1/58 356/317 |
| 2011/0008606 | A1 | | 1/2011 | Sun | |
| 2011/0111225 | A1 | | 5/2011 | Gabriele et al. | |
| 2012/0000480 | A1 | | 1/2012 | Sebastian et al. | |
| 2012/0231690 | A1 | | 9/2012 | Pourdeyhimi et al. | |
| 2013/0313484 | A1 | | 11/2013 | Sun | |
| 2014/0210127 | A1 | | 7/2014 | Sebastian | |

FOREIGN PATENT DOCUMENTS

| WO | WO 02/068736 A1 | 9/2002 |
| WO | WO 2006/020109 A2 | 2/2006 |
| WO | WO 2010/063945 A1 | 6/2010 |
| WO | WO 2012/054675 A2 | 4/2012 |

OTHER PUBLICATIONS

Office Communication notification dated May 5, 2016 received in co-pending U.S. Appl. No. 14/748,743.
Office Communication notification dated Mar. 1, 2017 received in co-pending U.S. Appl. No. 14/748,841.
Office Communication notification dated Feb. 27, 2017 received in co-pending U. S. Appl. No. 14/748,738.
Office Communication notification dated Mar. 13, 2017 received in co-pending U.S. Appl. No. 14/748,743.
Office Communication notification dated Sep. 7, 2017 received in co-pending U.S. Appl. No. 14/748,738.

(56) References Cited

OTHER PUBLICATIONS

Office Communication notification dated Sep. 11, 2017 received in co-pending U.S. Appl. No. 14/748,743.
Hendrick, Erin et al.; "Cellulose Acetate Fibers with Fluorescing Nanoparticles for Anti-counterfeiting and pH-sensing Applications"; Journal of Engineered Fibers and Fabrics, vol. 5, Issue 1; pp. 21-30; 2010.
Huang, C. et al.; "Unbreakable Codes in Electrospun Fibers: Digitally Encoded Polymers to Stop Medicine Counterfeiting"; Advanced Materials, vol. 22, Issue 24; pp. 2657-2668; May 5, 2010.
Konwarh, Rocktotpal et al.; "Electrospun cellulose acetate nanofibers: The present status and gamut of biotechnological applications"; Biotechnology Advances, vol. 31; pp. 421-437; 2013.
Lomas, B. and Simmens, S. C.; "The preparation of cross-sections of textile materials by grinding"; Journal of Microscopy, vol. 92, Part 1; pp. 37-45; Aug. 1970.
McBride, Murdoch; "Tobacco's Illicit Trade—How Legislation, Enforcement and Public Awareness Are Key to Tackling Illicit Trade, Part I—Overview"; Tobacco International; pp. 17-27; Dec. 2013.
Co-pending U.S. Appl. No. 14/748,884, filed June 24, 2015; McLeod et al.
Co-pending U.S. Appl. No. 14/748,841, filed June 24, 2015; Gaynor et al.

\* cited by examiner

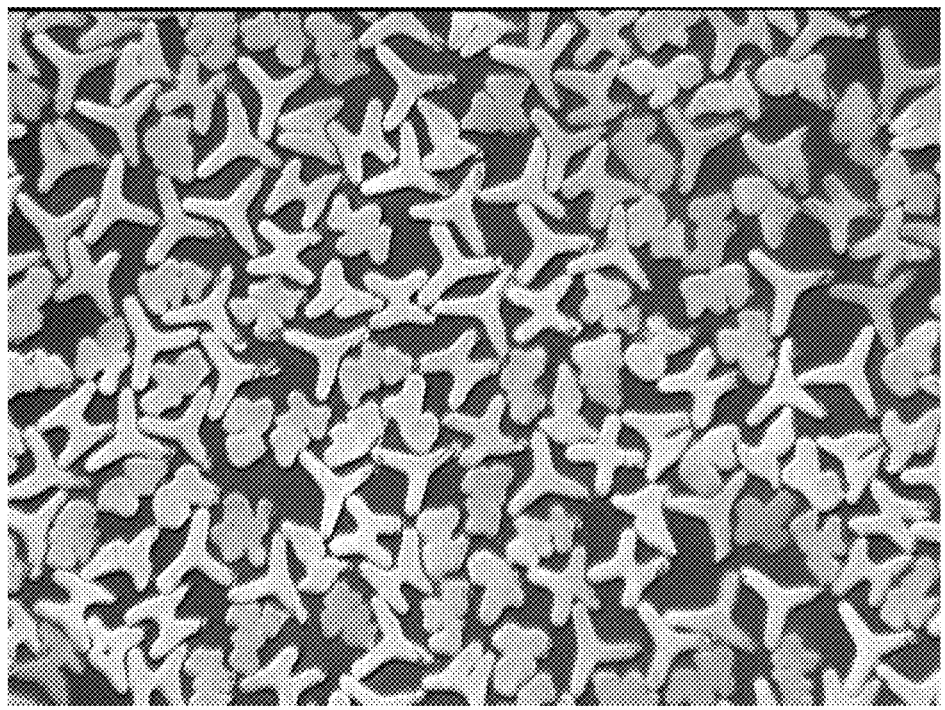
FIGURE 1(a) – Photomicrograph of fibers produced using triangle, circle, and square shaped spinneret holes

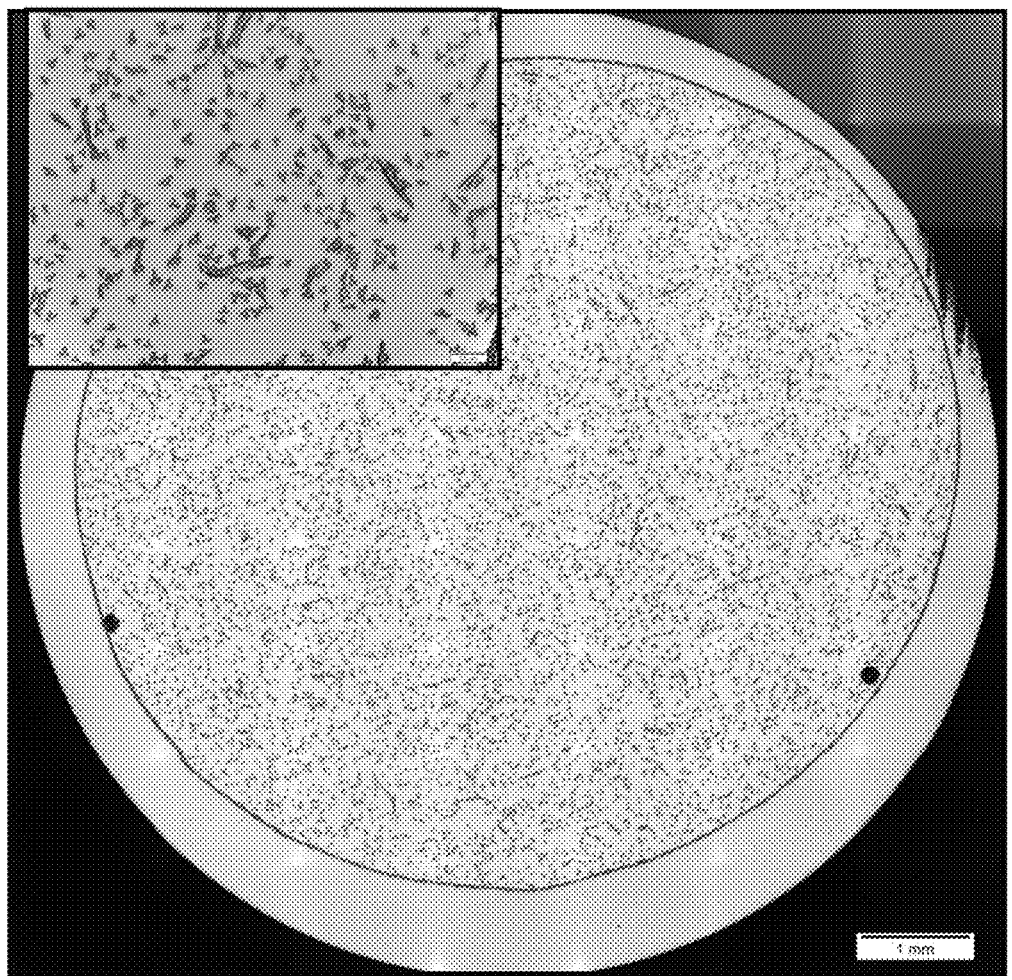
FIGURE 1(b) – Stitched image of full filter rod cross-section of Example 3 with an expanded region

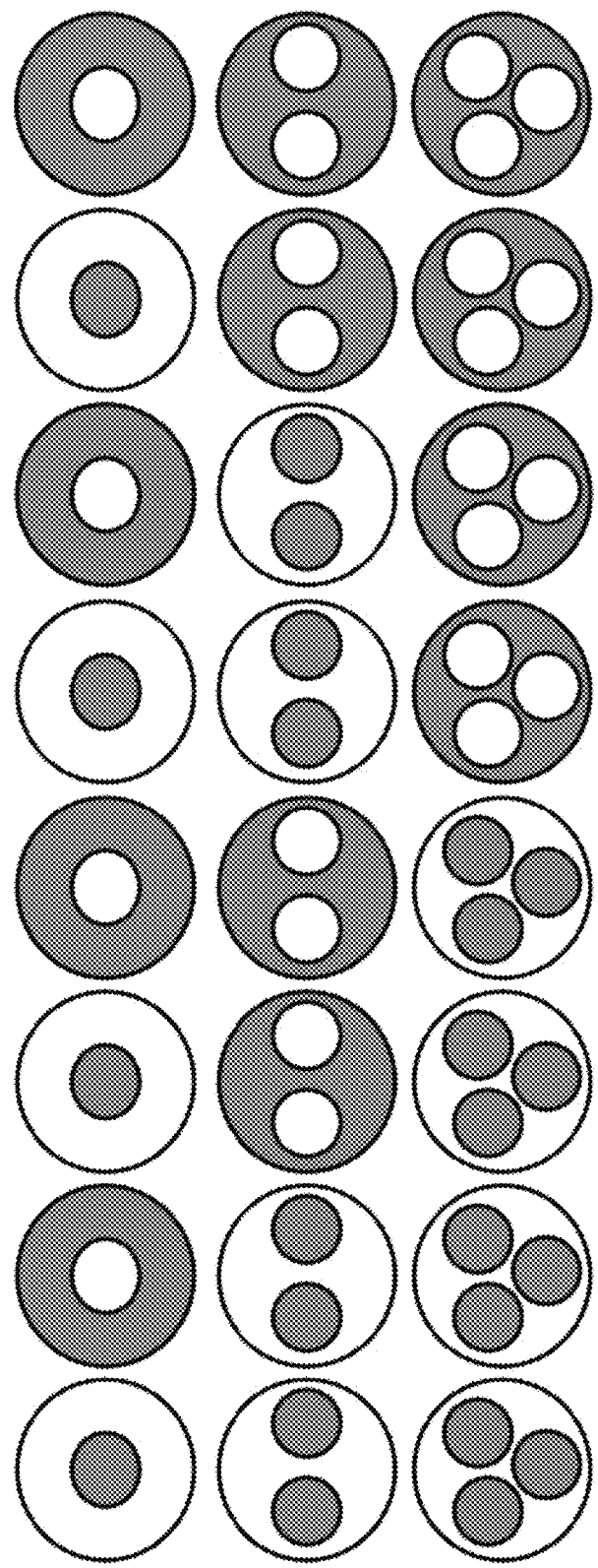
FIGURE 2

FIBERS WITH MULTICOMPONENT FIBERS USED FOR CODING

CROSS REFERENCES TO RELATED APPLICATIONS

This application claims priority under 35 U.S.C. 119(e) to U.S. Provisional Application Ser. No. 62/018,182, filed Jun. 27, 2014, U.S. Provisional Application Ser. No. 62/105,011, filed Jan. 19, 2015, and U.S. Provisional Application Ser. No. 62/164,135, filed May 20, 2015, each of which is incorporated herein by reference in its entirety.

TECHNICAL FIELD

This present disclosure relates to fibers, a fiber band or a yarn, containing identification fibers. The identification fibers can exhibit a plurality of distinct features, or taggants, which vary among the fibers of a fiber band or yarn. The present disclosure also relates to the method for making and characterizing the fiber band or yarn. Characterizing of the fiber band or yarn can include identifying distinct features, combinations of distinct features and/or the number of fibers with each combination of distinct features and correlating the distinct features supply chain information. The supply chain information can be used to track the fiber band or yarn from manufacturing through intermediaries, conversion to final product, and/or the consumer.

BACKGROUND

Many industries have a need to mark, tag, or identify products that allows for the tracking and tracing of products through the supply chain. One of the primary purposes for such track and trace systems is the combating of illicit trade such as counterfeiting and black market sales.

Anti-counterfeiting measures (ACMs) can be regarded as three different types: Type I (Overt), Type II (Covert) and Type III (Forensic). Type I ACMs are features incorporated into an article that are readily identified and observable to the naked eye. Examples include watermarks, color shifting inks, colored fibers, bands, or strips incorporated into the article, and holograms. Type II ACMs are features that are incorporated into the article that require some form of instrument to identify the feature in the field. The instruments required are generally those that are readily available and transportable. Some examples include the incorporation of very small text (requiring the use of a magnifying glass), UV responsive inks or threads (requiring illumination with a UV light), and barcodes or RFID tags (requiring a specialized reader). Type III ACMs are hidden attributes that require specialized laboratory equipment to identify. Some Type III examples include nano-text, micro-taggants, DNA inks, and chemical additives.

As stated above, there are many widely-used packaging and labelling taggants and anti-counterfeiting measures (ACMs) in many industries, but these more overt solutions are often susceptible to countermeasures such as destruction, modification, duplication, repackaging, or relabeling. Altering the physical features of the raw materials of a product can provide a more covert solution that is much more difficult to evade. These taggants may be used to track the fibers through the supply chain. The taggants may change the physical properties of the fibers, yarn fiber bands, and/or derivative articles in a manner that is difficult to copy or alter but is detectable using image analysis and/or other mechanical methods.

There is a need to manufacture, test, and track fibers in fiber bands or yarns and their derivative articles across a wide spectrum of industries. The ability to identify the source of a fiber band, yarn and/or an article comprising the fiber band or yarn can be achieved by embedding some form of a code in the fiber(s) during the manufacturing process that can then be later identified, retrieved, and used to identify the fiber band and/or the article.

Identification tags can be incorporated into the fibers, fiber band, or yarn that can denote, for example, manufacturer, manufacture site, customer, and ship-to location among other supply chain information that might be useful for the track and trace of the fiber band, yarn and/or article.

The disclosed exemplary embodiments can be used, for example, to combat the continuing and growing illicit-trade problem of tobacco products, particularly cigarettes. It has been estimated that 10-12% of all cigarette sales are illicit, either counterfeit copies or sales that avoid paying excise taxes on the cigarettes (Tobacco International, "Tackling Illicit Trade, Pt. I," December 2013). To combat this illicit trade requires a global effort consisting of manufacturers, distributors, regulators, and customs/law enforcement, as well as retailers who sell the cigarettes to consumers. There is a need to be able to track and ultimately trace components used in the construction of a cigarette. For example, the ability to track part of the supply chain path of acetate tow contained in the filter of a black market cigarette may give helpful information on the source of these illicit cigarettes.

There is a need for a traceable acetate tow that is readily manufactured, does not impact the performance of a cigarette filter, and is detectable, not only in an acetate tow band, but also in a single or a set of cigarettes/cigarette filters. There is a need for a traceable acetate tow that is readily accepted by cigarette manufacturers and consumers, such as an acetate tow that does not require adding chemicals which may impact taste and/or require regulatory approval. There is a need for traceable acetate tow that does not impact the pressure drop and yield of a cigarette filter. There is a need for traceable acetate tow that maintains its traceability when bloomed, plasticized, and formed into a filter.

BRIEF SUMMARY

In a first embodiment, fibers, a fiber band or yarn comprise identification fibers. The identification fibers comprise multicomponent fibers, wherein each of the multicomponent fibers comprises 2 to 100 segments. Each of the identification fibers exhibits at least one distinct feature. Each of the multicomponent fibers exhibit the at least one distinct feature comprising one or more taggant segment counts, one or more taggant segment shapes, one or more taggant segment sizes, one or more taggant segment geometrical relationships, or one or more taggant segment pointers. The identification fibers comprise one or more groups of distinguishable identification fibers, each group of the distinguishable identification fibers being formed by the identification fibers having the same distinct feature or a same combination of the distinct features The number of the identification fibers in each group of the distinguishable identification fibers is defined as a fiber count and at least one of the fiber counts corresponds to a taggant fiber count. The distinct features in each group of the distinguishable identification fibers and the one or more taggant fiber counts are representative of a code of the fibers.

In a second embodiment, an acetate tow band comprises fibers comprising standard fibers and identification fibers. The standard fibers comprise cellulose acetate fibers. The identification fibers comprise multicomponent fibers, wherein each of the multicomponent fibers comprises 2 to 100 segments. Each of the identification fibers exhibits at least one distinct feature. Each of the multicomponent fibers exhibit the at least one distinct feature comprising one or more taggant segment counts, one or more taggant segment shapes, one or more taggant segment sizes, one or more taggant segment geometrical relationships, or one or more taggant segment pointers. The identification fibers comprise one or more groups of distinguishable identification fibers, each group of the distinguishable identification fibers being formed by the identification fibers having the same distinct feature or a same combination of the distinct features. The number of the identification fibers in each group of the distinguishable identification fibers is defined as a fiber count and at least one of the fiber counts corresponds to a taggant fiber count. The distinct features in each group of the distinguishable identification fibers and the one or more taggant fiber counts are representative of at least one supply chain component of the acetate tow band.

In a third embodiment, a method for making identification fibers comprises spinning one or more polymers into the multicomponent fibers using one or more multicomponent spinpacks. The identification fibers comprise multicomponent fibers, wherein each of the multicomponent fibers comprises 2 to 100 segments. Each of the identification fibers exhibits at least one distinct feature. Each of the multicomponent fibers exhibit the at least one distinct feature comprising one or more taggant segment counts, one or more taggant segment shapes, one or more taggant segment sizes, one or more taggant segment geometrical relationships, or one or more taggant segment pointers. The identification fibers comprise one or more groups of distinguishable identification fibers, each group of the distinguishable identification fibers being formed by the identification fibers having the same distinct feature or a same combination of the distinct features. The number of the identification fibers in each group of the distinguishable identification fibers is defined as a fiber count and at least one of the fiber counts corresponds to a taggant fiber count. The distinct features in each group of the distinguishable identification fibers and the one or more taggant fiber counts establish a code of the fibers.

In a fourth embodiment, a method of characterizing a fiber sample comprising (1) applying imaging technology to the fiber sample, (2) detecting the groups of the distinguishable identification fibers, and (3) counting a number of each of the distinguishable identification fibers. The fiber sample comprises fibers, wherein the fibers comprise identification fibers and standard fibers. The identification fibers comprise multicomponent fibers, wherein each of the multicomponent fibers comprises 2 to 100 segments. Each of the identification fibers exhibits at least one distinct feature. Each of the multicomponent fibers exhibit the at least one distinct feature comprising one or more taggant segment counts, one or more taggant segment shapes, one or more taggant segment sizes, one or more taggant segment geometrical relationships, or one or more taggant segment pointers. The identification fibers comprise one or more groups of distinguishable identification fibers, each group of the distinguishable identification fibers being formed by the identification fibers having the same distinct feature or a same combination of the distinct features The number of the identification fibers in each group of the distinguishable identification fibers is defined as a fiber count and at least one of the fiber counts corresponds to a taggant fiber count. The distinct features in each group of the distinguishable identification fibers and the one or more taggant fiber counts are representative of at least one supply chain component of the of the fiber sample.

BRIEF DESCRIPTION OF THE DRAWINGS

FIGS. 1(a) illustrates a fiber band containing cellulose acetate fibers with three cross-section shapes and 1(b) illustrates a illustrates a stitched-together photomicrograph of a filter rod of Example 3.

FIG. 2 illustrates a non-limiting example of sets of identification fibers that could be used to represent supply chain information.

DETAILED DESCRIPTION

Figure 3A:
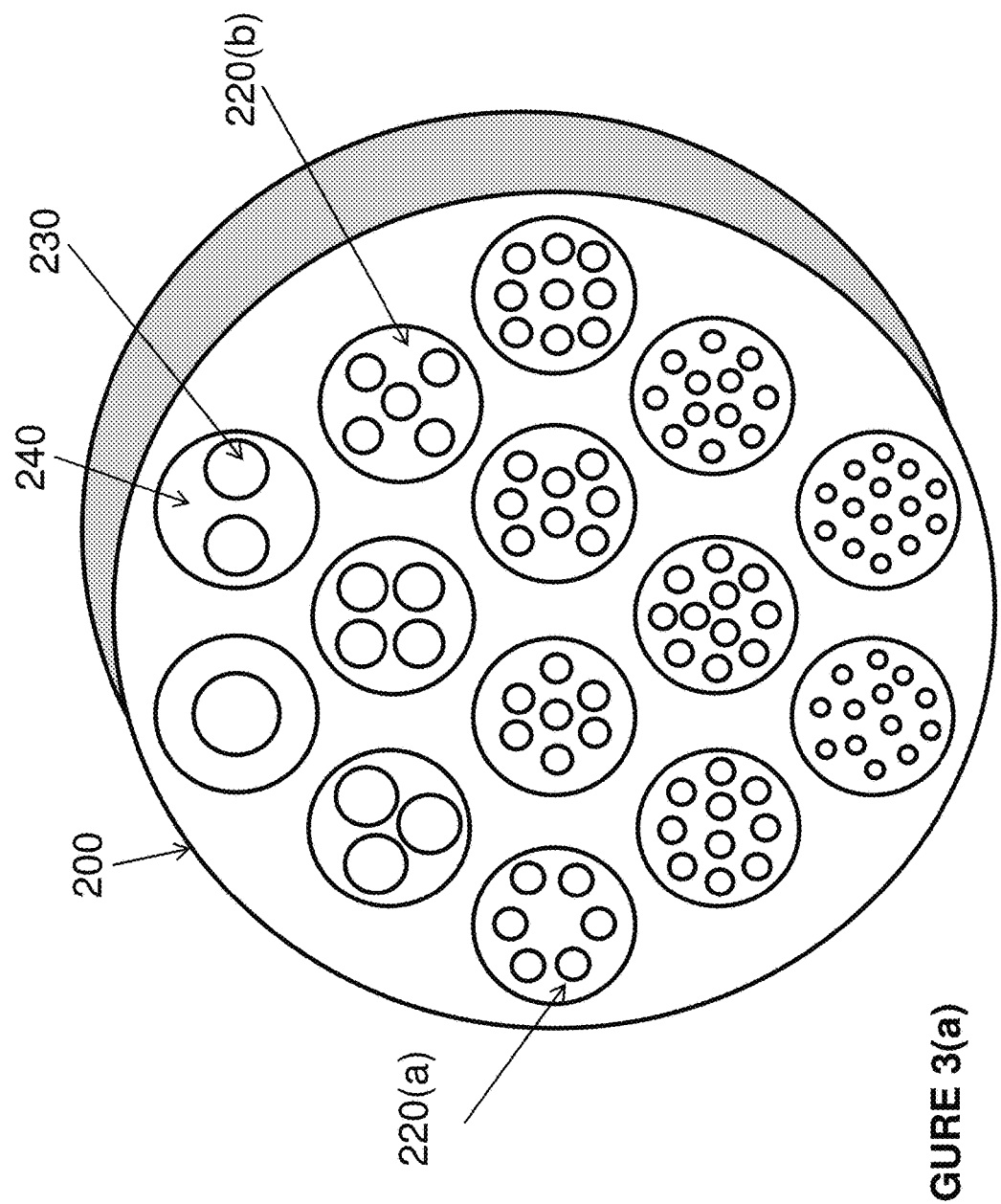
FIGS. 3(a) and 3(b) illustrate non-limiting examples of a multicomponent fiber spinpacks capable of producing multicomponent fibers with different numbers of segments.

In a first embodiment, fibers, a fiber band or a yarn comprise identification fibers. The identification fibers comprise multicomponent fibers, wherein each of the multicomponent fibers comprises 2 to 100 segments. Each of the identification fibers exhibits at least one distinct feature. Each of the multicomponent fibers exhibit the at least one distinct feature comprising one or more taggant segment counts, one or more taggant segment shapes, one or more taggant segment sizes, one or more taggant segment geometrical relationships, or one or more taggant segment pointers. The identification fibers comprise one or more groups of distinguishable identification fibers, each group of the distinguishable identification fibers being formed by the identification fibers having the same distinct feature or the same combination of the distinct features. The number of the identification fibers in each group of the distinguishable identification fibers is defined as a fiber count and at least one of the fiber counts corresponds to a taggant fiber count. The distinct features in each group of the distinguishable identification fibers and the one or more taggant fiber counts establish a code of the fibers.

Unless otherwise indicated, all numbers expressing quantities of ingredients, properties such as molecular weight, reaction conditions, and so forth used in the specification and claims are to be understood as being modified in all instances by the term "about."

It is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "fibers", as used herein, refers to thin flexible threadlike objects. Fibers can be natural fibers or man-made. The term "polymer", as used herein refers to the base material from which the fibers are made. Non-limiting examples of polymers include acrylic, modacrylic, aramid, nylon, polyester, polypropylene, rayon, polyacrylonitrile, polyethylene, PTFE, and cellulose acetate. The term "filament", as used herein, refers to a single fiber. The term "fiber band", as used herein, refers to multiple fibers placed adjacent to each other along their lengths such that the fibers remain untwisted or entangled and form a substantially rectangular cross section with a high width-to-depth ratio. Fiber bands are often formed to allow for effective crimping of the fibers and can be cut into a staple or processed as a continuous band, depending on the end use. Fiber bands are typically not woven or knitted into a fabric article unless first converted into staple to form a thread. Fibers can also be in the form of yarns. The term "yarn, as used herein, refers to multiple fibers placed adjacent to each other along their lengths, often twisted or entangled together to improve fiber cohesiveness and performance, and typically forming a substantially rounded cross section. Yarn can be processed as continuous strands or cut into smaller lengths, depending on the end use.

Fibers can be identification fibers and/or standard fibers. The term "standard fibers", as used herein, refers to fibers which are manufactured for the primary purpose and use in producing articles. Standard fibers have not been purposefully manipulated to comprise distinct features used to identify and track the standard fibers, yarn, a fiber band, and/or an article comprising standard fibers. The term "identification fibers", as used herein, refers to the fibers having distinct features such that the identification fibers can be used to identify and track the standard fibers, yarn, a fiber band, and/or an article comprising the standard fibers and the identification fibers.

The term "multicomponent fibers", as used herein, are fibers which contain 2 or more distinguishable segments per filament.

The term "distinct features", as used herein, refers to variances among fibers that can be identified using imaging technology. Non-limiting examples of distinct features include cross-section shapes, cross-section sizes, optical properties, and surface markings. For multicomponent fibers, non-limiting examples of distinct features also include segment counts, segment shapes, segment sizes, segment geometrical relationships, and segment pointers. The term "combination of distinct features", as used herein, refers to the two or more distinct features exhibited by an identification fiber.

The term "distinguishable identification fibers", as used herein, refers to identification fibers having the same distinct feature or combination of distinct features. The term a "group of the distinguishable identification fibers", as used herein, refers to one or more filaments of the distinguishable identification fibers. The term "reference fiber", as used herein, refers to a particular distinguishable identification fiber that can be used, for example, to calibrate distinct features, such as cross-section size, of other distinguishable identification fibers. The identification fibers consist of all of the groups of the distinguishable identification fibers.

The term "fiber counts", as used herein, refers to the number of each of the distinguishable identification fibers that are physically present in the fibers, yarn, fiber bands, and/or article. The term "taggant fiber counts", as used herein, refers to the collection of fiber count alternatives for each of the distinguishable identification fibers which can be established used by one or more entity (e.g., manufacturer) in a system for embedding and/or determining standard fibers, yarn, fiber band, and/or article supply chain information.

The term, "cross-section shapes", as used herein, refers to the contours of fibers when viewed on the plane cutting through the fibers at right angles to their length. The term "taggant cross-section shapes", as used herein refers to a collection of cross-section shapes used by one or more entity (e.g., manufacturer) in a system for embedding and/or determining standard fibers, yarn, and/or fiber band supply chain information. Reference cross-section shape refers to the cross-section shape of the reference fiber.

The term, "cross-section sizes", as used herein, refers to the quantitative dimension of fibers when viewed on the plane cutting through the fibers at right angles to their length. For a circular cross-section shape, the cross-section size can be the diameter of the cross-section. For a noncircular cross-section shape, the area of the cross-section can be determined and the cross-section size can be characterized as the effective diameter. The effective diameter is the corresponding diameter of a circular cross-section having the same area. For noncircular cross sections, the cross section size can also be characterized by the circumcised diameter, defined as the diameter of the smallest circle that can completely encompass the cross section. The term "taggant cross-section sizes", as used herein refers to a collection of cross-section sizes used by one or more entity (e.g., manufacturer) in a system for embedding and/or determining standard fibers, yarn, and/or fiber band supply chain information. Reference cross-section size refers to the cross-section size of the reference fiber.

The term, "optical properties", as used herein, refers to electromagnetic radiation responses observed when the fibers and/or segments of multicomponent fibers are exposed to a specific electromagnetic radiation sources. The term includes color which can be observed with the human eye as well as with an instrument such as one capable of identifying a spectrophotometric signature. Non-limiting examples of electromagnetic radiation include x-ray, ultraviolet, visible light, infrared, and so-called "T-ray" (terahertz frequencies). The term "taggant optical properties", as used herein refers to a collection of known optical properties used by one or more manufacturer in a system for determining fibers, fiber band, and/or yarn supply chain information.

The term, "segment counts", as used herein, refers to the numbers of segments present in each of the multicomponent fibers. Multicomponent fibers with different segment counts are distinguishable identification fibers. The term "taggant segment counts", as used herein, refers to a collection of segment counts for each of the distinguishable multicomponent fibers which can be used by one or more entity (e.g., manufacturer) in a system for embedding and/or determining standard fibers, yarn, fiber band, and/or article supply chain information.

The term, "segment shapes", as used herein, refers to the cross-section shape of segments within a multicomponent fiber. The term "taggant segment shapes", as used herein, refers to a collection of cross-section shapes used by one or more entity (e.g., manufacturer) in a system for embedding and/or determining standard fibers, yarn, and/or fiber band supply chain information.

The term, "segment sizes", as used herein, refers to the cross-section size of segments within a multicomponent fiber. The term "taggant segment sizes", as used herein, refers to a collection of cross-section sizes used by one or more entity (e.g., manufacturer) in a system for embedding and/or determining standard fibers, yarn, and/or fiber band supply chain information.

The term, "segment geometrical relationships", as used herein, refers to the relative location of one or more segments of a multicomponent fiber. The term "taggant geometrical relationships", as used herein refers to a collection of geometrical relationships used by one or more manufacturer in a system for determining fibers, fiber band, and/or yarn supply chain information.

The term "segment pointers" as used herein, refers to physical features of the multicomponent fiber used to give orientation for assessing the geometrical relationship of segments. The term "taggant segment pointers", as used herein refers to a collectin of segment pointers used by one or more manufacturer in a system for determining fibers, fiber band, and/or yarn chain information.

The term "majority of fibers", as used herein, refers to greater than 50 percent of the fibers in the yarn or fiber band based on the total number of fibers.

The term "total identification fibers number", as used herein, refers to the sum of each of the identification fibers in the yarn or fiber band. The term "taggant total identification fibers number", as used herein, refers to the total number of identification fibers used by one or more entity (e.g., manufacturer) in a system for embedding and/or determining fibers, fiber band, and/or yarn supply chain information.

The term, "cellulose acetate", as used herein, refers to an acetate ester of cellulose wherein the hydrogen in the hydroxyl groups of the cellulose glucose unit is replaced by acetyl groups through an acetylation reaction. In some embodiments, suitable cellulose acetates may have a degree of substitution less than about 3 acetyl groups per glucose unit, preferably in the range of 2.2 to about 2.8, and most preferably in the range of 2.4 to 2.7.

The terms, "cellulose acetate tow", "acetate tow", or "acetate tow band" as used herein, refers to a continuous, crimped fiber band comprising of cellulose acetate fibers.

The term, "article", as used herein, refers to a unit produced from standard fibers, yarn, and/or a fiber band, including other components and additives needed to meet the functional requirements of the intended use. Non-limiting examples include fabrics and other textile products, non-wovens, absorbent products, filters, filter rods, cigarette filters and liquid storage reservoirs. The term "article comprising fibers, yarn and/or fiber bands", as used herein, refers to the article comprising the fibers, yarn and/or fiber bands with a recognition that, in some embodiments, significant physical changes can occur to the fibers, yarn and/or fiber band, when it is used to make an article.

The term, "filter", as used herein refers to a semi-permeable fibrous material. Non-limiting examples of filters include a filter rod, and items made from a filter rod such as a cigarette filter. The term "filter rod", as used herein, refers to a rod-like article, of any cross-sectional shape, produced from a fiber band and other components or additives, which can be subsequently used as a whole unit, or cut into lengths to form multiple units, for filtration of a vapor stream. Filter rods can be used to filter tobacco products, for example, traditional cigarette filters and/or other applications for other tobacco products including heat-not-burn products. Filter rods can also be used for new products comprising tobacco and other ingredients such as, for example, other plants or plant derivatives. Filter rods can be used to filter other plants and plant derivatives, with or without tobacco present. Additionally filter rods can be used to filter any vapor stream used to deliver an active ingredient such as in e-cigarette.

The term, "cigarette filter", as used herein, refers to a component of the cigarette or other smoking device which removes or decreases one or more elements from a smoke stream. The term cigarette filter is intended to encompass the filter on any smoking device including the non-limiting examples of a cigarette, a cigarette holder, a cigar, a cigar holder, a pipe, a water pipe, a hookah, an electronic smoking device, a roll-your-own cigarette, a roll-your-own cigar, and a paper.

The term, "supply chain information" as used herein, refers to information regarding the production of the standard fibers, yarn, and/or fiber band and information regarding the distribution of the standard fibers, yarn, and/or fiber band after its production. Supply chain information includes "supply chain components" such as, for example, manufacturer, manufacture site, manufacture line, production run, production date, a package, bale, customer, customer ship-to location, warehouses, freight carrier, and/or shipment paths or routes. Supply chain components can apply to fibers, yarn, fiber bands, and/or articles.

The term, "manufacturer", as used herein, refers to the entity that produces the standard fibers, yarn and/or fiber band.

The term "manufacture site", as used herein, refers to the geographic location or locations of the manufacturer, designated by any level of specificity including full address, continent, country, state, province, county, or city.

The term "manufacture line", as used herein, refers to specific process equipment or set of equipment used by the manufacturer to produce the standard fibers, yarn, and/or fiber band.

The term "production run", as used herein, refers to a group or set of similar or related goods that are produced by using a particular set of manufacturing procedures, processes, or conditions and/or product specifications.

The term "customer", as used herein, refers to an entity to which the fibers, fiber band, and/or yarn is sold and shipped for further processing into an intermediate article or a finished product article; or an entity that purchases the fibers, yarn and/or fiber band for resale.

The term, "ship-to location", as used herein, refers to the geographic location of the customer designated for delivery of the fibers, yarn and/or, fiber band by any level of specificity including full address, continent, country, state, province, county, or city.

The term, "bale" as used herein, refers to a packaged unit of fiber bands, typically of a cubical shape, compressed to a high density, and wrapped, contained, and protected by packaging material.

The term, "warehouse" as used herein, refers to the geographical location of the warehouse designated for delivery of the fibers, yarn and/or, fiber band by any level of specificity including full address, continent, country, state, province, country, or city.

The term, "correlating", as used herein refers to establishing the relationship between two or more pieces of information.

The term, "manufacturer specific taggants", as used herein, refers to the particular taggants incorporated into fibers, yarn and/or, fiber band by a particular manufacturer. The term, "manufacturer specific taggant set" refers to the taggant cross-section shapes and/or taggant cross-section sizes associated with a particular manufacturer.

The term, "fibers are produced", "producing fibers", and "fiber production process", as used herein, refers to the process steps of spinning fibers up through the gathering of the fibers.

The term, "identification fibers are packaged", as used herein, refers to the process steps of transferring identification fibers from the spinning machine and packaging the identification fibers, for example, onto a spool or into a bale. The identification fibers would subsequently need to be removed from the package in order to be incorporated into fibers, yarns, fiber band, and/or article comprising the standard fibers.

The term, "spinneret hole geometry", as used herein, refers to the overall structure of the spinneret hole which can be described most completely and generally, although not exclusively, by the cross-section shape and size of the hole at any point in its line through the spinneret. The term, "distinguishable spinneret hole", as used herein, refers to the spinneret hole with a distinguishable spinneret hole geometry. Each of the distinguishable identification fibers are produced using the same distinguishable spinneret hole geometry. The term "reference spinneret holes", as used herein, refers to the spinneret holes used to produce the reference fibers.

The term, "multicomponent fiber spinpack", as used herein refers to a mechanical system comprising two or more polymer inlets, polymer distribution plates, and polymer outlets wherein the polymer outlets are configured to produce multicomponent fibers.

The term "fiber sample", as used herein, refers to the item comprising fibers, in any physical form, being analyzed using imaging technology. The fiber sample can comprise a portion of a set of fibers, yarn, a fiber band, or an article which has been prepared for image analysis.

The terms, "imaging technology", and "image analysis techniques" as used herein, refer to the equipment and software used to detect and quantify differences in reflection, absorption, transmission, and emittance of electromagnetic radiation. Imaging technology encompasses both electromagnetic radiation level detection and automated shape and/or size recognition.

The term, "fibers are incorporated into a matrix", as used herein refers to the immobilizing at least some of the fibers, yarns, a fiber band, or an article, typically in a polymer that will not interfere with testing.

Fibers, a fiber band, and/or a yarn comprise individual fibers. The material from which the fibers are made is not particularly limiting. The fibers can comprise, for example, acrylic, modacrylic, aramid, nylon, polyester, polypropylene, rayon, or cellulose acetate. In one aspect, the fibers comprise cellulose acetates, cellulose triacetates, cellulose propionates, cellulose butyrates, cellulose acetate-propionates, cellulose acetate-butyrates, cellulose propionate-butyrates, cellulose acetate-phthalates, starch acetates, acrylonitriles, vinyl chlorides, vinyl esters, vinyl ethers, and the like, any derivative thereof, any copolymer thereof, and any combination thereof. In one aspect, the fibers comprise cellulose acetate. In one aspect, the fibers comprise natural fibers such as, for example, cotton, hemp, and/or silk.

In one aspect, the fibers, fiber band, or yarn comprises standard fibers and one or more identification fibers. Fibers are typically produced from a polymer. In one aspect, one or more of the identification fibers comprise the same polymer as the standard fibers. In another aspect, one or more of the identification fibers comprise a different polymer than the standard fibers band.

In one aspect, one or more of the identification fibers can be multicomponent fibers. Multicomponent fibers contain two or more distinct polymer compositions (components) within one cross section. They can be tailored to suit aesthetic and functional requirements for numerous applications and can produce fibers with unique optical or physical properties. Multicomponent fibers typically comprise 2 or 3 components and 2 or more segments. The polymer compositions can be distinguished as comprising different polymers, as comprising different additives, and/or comprising polyermer compositions having different physical characteristics (e.g., different degrees of crystallinity).

The structure of the multicomponent fibers is not particularly limiting and includes without limitation sections comprising sheath/core, "islands in the sea", side-by-side, and segmented pie. The segments only need be distinguishable from one another using imaging technology.

The size of the individual fibers is not particularly limiting. The size can be given in terms of effective diameter, and in one aspect, the effective diameter of the fibers range, for example, from 0.1 μm to 1000 μm, 1 μm to 500 μm, 1 μm to 100 μm, 1 μm to 30 μm, 10 μm to 1000 μm, 10 μm to 500 μm, 10 μm to 100 μm, 10 μm to 30 μm. In one aspect, the standard fibers comprise cellulose acetate for which size is often given in terms of denier per filament (dpf) which is defined as the weight, in grams, of a single filament 9000 meters in length. In one aspect, the size of the fibers ranges from 0.5 to 1000 dpf; 0.5 to 500 dpf; 0.5 to 100; 0.5 to 5 dpf; 0.5 to 30 dpf; 0.5 to 10 dpf; 1 to 1000 dpf; 1 to 500 dpf; 1 to 100; 1 to 5 dpf; 1 to 30 dpf; 1 to 10 dpf. In one aspect, the dpf of the fibers ranges from, for example, 1 to 30 dpf, 1 to 20 dpf, 1 to 10 dpf, 2 to 30 dpf, 2 to 20 dpf, or 2 to 10 dpf.

The number of fibers making up a fiber band is not particularly limiting. In one aspect, the number of fibers in a fiber band can range from 10 to 50,000. In other non-limiting examples, the number of fibers in a fiber band ranges from 10 to 40,000; 10 to 30,000; 10 to 20,000; 10 to 10,000; 10 to 1000; 100 to 50,000; 100 to 40,000; 100 to 30,000; 100 to 20,000; 100 to 10,000; 100 to 1000; 200 to 50,000; 200 to 40,000; 200 to 30,000; 200 to 20,000; 200 to 10,000; 200 to 1000; 1000 to 50,000; 1000 to 40,000; 1000 to 30,000; 1000 to 20,000; 1000 to 10,000; 5000 to 50,000; 5000 to 40,000; 5000 to 30,000; 5000 to 20,000; 5000 to 10,000; 10,000 to 50,000; 10,000 to 40,000; 10,000 to 30,000; or 10,000 to 20,000.

In one aspect, essentially all of the fibers in the fiber band or yarn are identification fibers. In this aspect, the identification fibers can be distinguishable from standard fibers in a different fiber band or yarn (and will be combined with standard fibers to product an article) or the identification fibers can be used interchangeably with standard fibers for the production of articles. In another aspect, one or more identification fibers are distinguishable from the majority of fibers in the same fiber band or yarn. In yet another aspect, the number of identification fibers ranges from 0.001 to 100 percent of the fibers; or 0.01 to 50 percent of the fibers; or 0.01 to 25 percent of the fibers; or 0.01 to 10 percent of the fibers; or 0.01 to 5 percent of the fibers; or 0.01 to 1 percent of the fibers, each based on the total number of fibers. In another aspect, the number of identification fibers ranges from 0.01 to 100 percent of the fibers; or 1 to 100 percent of the fibers; or 25 to 100 percent of the fibers; or 50 to 100 percent of the fibers; or 30 to 80 percent of the fibers.

Each of the identification fibers exhibit at least one distinct feature. In one aspect, the distinct features can include cross-section shapes. In another aspect, the distinct features can include cross-section sizes. In another aspect, the distinct features can include cross-section shapes and cross-section sizes. In one aspect, distinct features are representative of at least one supply chain component of fibers, yarn, fiber band, and/or an article. In one aspect, the distinct features in each group of the distinguishable identification fibers and the fiber counts are representative of at least one supply chain component of fibers, yarn, fiber band, and/or an article.

In one aspect, the identification fibers exhibit 1 to 50 distinct features. In other aspects, the number of distinct features ranges from 1 to 20, 1 to 15, or 1 to 10, or 1 to 5, 1 to 3, 2 to 50, 2 to 20, 2 to 15, 2 to 10, 2 to 5, 3 to 50, 3 to 20, 3 to 15, 3 to 10, 3 to 5, 4 to 50, 4 to 20, 4 to 15, or 4 to 10.

In one aspect, the distinct features can include cross-section shapes, cross-section sizes, optical properties, segment counts, segment geometrical relationships, and/or segment pointers. The distinct features can be used alone or in any combination. In one aspect, the distinct features can include taggant cross-section shapes, taggant cross-section sizes, taggant optical properties, and/or taggant segment counts, taggant segment geometrical relationships, and/or taggant segment pointers.

In one aspect, fiber cross-section shapes can be used as a taggant. In one aspect, distinct features comprise one or more cross-section shapes. Cross-section shapes vary such that either the human eye or an image analysis technique can differentiate shapes. For example, two shapes are significantly different when compared to the variability among the fibers of either cross-section shape. In one aspect, a fiber band comprises one or more identification fibers with one or more taggant cross-section shapes. In one aspect, the number of taggant cross-section shapes ranges from 1 to 50. In other aspects, the number of taggant cross-section shapes ranges from 1 to 20, 1 to 15, or 1 to 10, or 1 to 5, 1 to 3, 2 to 50, 2 to 20, 2 to 15, 2 to 10, 2 to 5, 3 to 50, 3 to 20, 3 to 15, 3 to 10, 3 to 5, 4 to 50, 4 to 20, 4 to 15, or 4 to 10.

In one aspect, the number of identification fibers with distinct features which comprise one or more taggant cross-section shapes ranges from 0.01 to 100 percent of the fibers; or 0.01 to 50 percent of the fibers; for 0.01 to 25 percent of the fibers; for 0.01 to 10 percent of the fibers; or 0.01 to 5 percent of the fibers; or 0.01 to 1 percent of the fibers.

Many cross-section shapes have been commercialized for various fiber types, materials, and processes. These shapes are most typically governed and created by altering the shape of the hole in the extrusion jet or spinneret used in the fiber production process. In a dry spinning process, like that of cellulose acetate in an acetone "dope" solution, a number of unique fiber cross-section shapes can be obtained through the use of various spinneret hole geometries. The variety and distinctiveness of the cross-section shapes are enhanced due to the shrinkage of the cross section as the acetone evaporates. Many of these shapes are sufficiently unique and differentiated such that they can be easily identified and/or counted in fiber bands, and/or acetate tow bands, either by the human eye with the aid of magnification, or with automated image analysis techniques.

For some fiber applications, the fiber cross-section shape is not critical to the functionality of an article made from the fibers, yarn, or fiber band. For these applications, the number of taggant cross-section shapes and the number of identification fibers having different taggant cross-section shapes are not particularly limited. For other fiber applications, however, the fiber cross-section shape is used to impart functionality to an article made from the fibers, yarn, or fiber band. For these applications, the number of taggant cross-section shapes and/or the number of identification fibers having different taggant cross-section shapes may be smaller. One skilled in the art can select the number of taggant cross-section shapes and the number of identification fibers having distinct features of taggant cross-section shapes so as to enable determination of the supply chain information without significantly impacting article properties.

In the application of filter rods and/or cigarette filters comprising acetate tow, the total number of identification fibers may be limited by the impact of the taggant cross-section shape on final product performance, particularly yield, defined as the pressure drop that can be obtained for a certain weight of product in the filter. By far, the most common shape used for acetate tow in cigarette filtration is the Y cross section (made from an equilateral triangular spinneret hole geometry) and the most common shape used for acetate yarn is multi-lobed (made from a circular or octagonal spinneret hole geometry). As the number of non-Y shape fibers increases, the impact (positive or negative) on yield may materially impact article functionality. One method, among others, for compensating for this yield shift is adjusting the average denier per filament (dpf) of the fibers.

Non-limiting examples of cross-section shapes include crescent, dogbone, triangle, square, pacman, multilobe, X-shaped, Y-shaped, H-shaped. Non-limiting examples of spinneret hole geometries used to make various cross-section shapes include triangle, circle, rectangle, square, flattened round, trapezoid, hexagon, pentagon, and D-shaped. In another aspect, spinneret hole geometry is selected from the group consisting of circle, rectangle, square, flattened round, trapezoid hexagon, pentagon, and D-shaped.

The disclosed embodiments may, for example, enable the use of fiber cross-section sizes as a taggant. In one aspect, distinct features comprise one or more cross-section sizes. Cross-section sizes vary such that either the human eye or an image analysis technique can differentiate sizes. The fibers, yarn, or fiber band can have one or more identification fibers with one or more taggant cross-section sizes. The number of taggant cross-section sizes ranges from, for example, 1 to 50, 1 to 25; 1 to 20; 1 to 10; 1 to 5; 1 to 3; 2 to 20; 2 to 10; 2 to 5; or 3 to 10.

In one aspect, the number of identification fibers with distinct features which comprise taggant cross-section sizes ranges from 0.01 to 100 percent of the fibers; or 0.01 to 50 percent of the fibers; for 0.01 to 25 percent of the fibers; for 0.01 to 10 percent of the fibers; or 0.01 to 5 percent of the fibers; or 0.01 to 1 percent of the fibers, based on the total number of fibers.

In one aspect, one or more identification fibers have one or more taggant cross-section sizes that are larger than the average cross-section size of the standard fibers. In one aspect, the ratio of the larger taggant cross-section sizes to the average cross-section size ranges from 20:1 to 1.5:1, or 10:1 to 1.5:1, or 5:1 to 1.5:1, or 3:1 to 1.5:1, 20:1 to 1.3:1, or 10:1 to 1.3:1, or 5:1 to 1.3:1, or 3:1 to 1.3:1, or 20:1 to 1.1:1, or 10:1 to 1.1:1, or 5:1 to 1.1:1, or 3:1 to 1.1:1. In one aspect, one or more identification fibers have cross-section sizes that are smaller than the average cross-section size of the standard fibers. In one aspect, the ratio of the smaller cross-section sizes to the average cross-section size ranges from 1:20 to 1:1.5, or 1:10 to 1:1.5, or 1:5 to 1:1.5, or 1:2 to 1:1.5, or 1:20 to 1:1.3, or 1:10 to 1:1.3, or 1:5 to 1:1.3, or 1:2 to 1:1.3, or 1:20 to 1:1.1, or 1:10 to 1:1.1, or 1:5 to 1:1.1, or 1:2 to 1:1.1. The cross-section sizes can be determined by either the effective diameter or the circumcised diameter.

In yet another aspect, one or more taggant cross-section sizes varies along the length of one or more identification fibers such that the cross-section size varies from 0.25 times to 4.0 times; 0.25 times to 2.0 times; 0.5 times to 4.0 times; or 0.5 times to 2.0 times the average identification fiber cross-section size.

The number or percentage of identification fibers with taggant cross-section sizes that can be incorporated into a multiple-filament product, like acetate tow for cigarette filters, is potentially limited by a few factors. First, the number may be limited by the impact of the diameter differences on final product performance, particularly yield. This yield shift could be compensated by adjusting the average denier per filament (dpf) of the standard fibers. Second, the number may be dictated by the capability of the analytical technique to accurately count individual fibers of unique cross-section diameter. If the correlation among the distinct features and the manufacturer-specific taggants includes the number of identification fibers with one or more cross-section sizes, discrete gaps in filament number or percentage may be desired in order to facilitate number differentiation.

Optical properties encompass the effects of a substance or structure on electromagnetic radiation. The effects include absorption, scattering, refraction, fluorescence, and polarization. Electromagnetic radiation includes visible, ultraviolet, and infrared light as well as x-rays, microwaves, and radio waves. The effects impact some wavelengths more than others which impart distinctive, identifying characteristics. The effects can be detected by various forms of spectroscopy or by direct observation.

An example is a dye which absorbs portions of the visible light spectrum more than other parts and, thereby, imparts a distinctive color which can be observed directly or measured with a spectrometer.

The disclosed embodiments may use optical properties as a taggant. In one aspect, distinct features comprise one or more optical properties. Optical properties vary such that either the human eye or an image analysis technique can differentiate the optical properties. A fiber band or yarn can have one or more identification fibers with one or more taggant optical properties. In one aspect, taggant optical properties are imparted by taggant compounds which emit or absorb light at distinguishable $\lambda_{max}$ (wavelength of maximum emission or absorption) where the number of taggant compounds which product distinguishable λmax range from 1 to 10, or 1 to 5, or 1 to 3. In another aspect, taggant optical properties are distinguishable taggant colors where the number of taggant colors range from 1 to 10, or 1 to 5, or 1 to 3.

Some non-limiting examples of compounds which can be used for one or more taggant optical properties of the identification fibers include organic dyes, organometallic phosphorescent compounds, inorganic fluorescent/phosphorescent molecules, inorganic quantum dots, and/or organic quantum dots. Additional non-limiting example compounds include Cromophtal Red 2030 (CAS No. 84632-65-5), Copper Phthalocyanine (CAS No. 147-14-8) FD&C Yellow Lake No. 5 (CAS No. 12225-21-7), and titanium dioxide in anatase, rutile, and/or mixed phase. In one aspect taggant optical properties are used to distinguish segments in multicomponent fibers.

For multicomponent identification fibers, additional distinct features include segment counts, segment shapes, segment sizes, segment geometrical relationships, and segment pointers. For example, if the multicomponent fibers have any number from 2 to 20 islands per multicomponent fiber, then the number of taggant segment counts is 19, with 2-20 islands for each taggant segment count. Alternatively, if the multicomponent fibers have either 5, 10, or 20 islands per multicomponent fiber, then the number of taggant segment counts would be 3 with 5, 10, or 20 islands per taggant segment count. If the multicomponent fibers have either 50 or 100 segments per multicomponent fiber, then number of taggant segment counts would be 2, with 50 or 100 taggant segment counts. The number of taggant segment counts directly correlates to the number of multicomponent distinguishable identification fibers.

The number of segment counts is selected, in part, based upon the ability to manufacture and reliably detect discrete segments of each of the multicomponent distinguishable identification fibers. In one aspect, the ranges of the numbers of segments counts can be 2 to 25, 2 to 15, 2 to 10, 2 to 20, 2 to 15, 2 to 10, 2 to 5, 3 to 20, 3 to 15, 3 to 10, 3 to 5, 4 to 20, 4 to 15, or 4 to 10. In one aspect, segment counts can be correlated to supply chain information.

In one aspect, identification fibers comprise multicomponent fibers and taggant segment geometries can be used to distinguish among multicomponent identification fibers. For example, a first multicomponent fiber with 2 segments in a core/sheath formation is clearly distinguishable from a second multicomponent fiber with 2 segments that are side-by-side. In one aspect, taggant segment geometries are used as a means for increasing the number of multicomponent distinguishable identification fibers.

In one aspect, identification fibers comprise multicomponent fibers and taggant segment pointers can be used to distinguish among multicomponent identification fibers. For example, if multicomponent fibers have 5 islands in the sea wherein the 5 islands make a concentric circle and the colors of the islands are, in order, red, yellow, orange, blue, and green; then a first multicomponent fiber with a notch between the red and yellow island is distinguishable from a second multicomponent fiber with a notch between the orange and the blue islands. In one aspect, taggant segment pointers can be used as a means for increasing the number of multicomponent distinguishable identification fibers.

In one aspect, each of the identification fibers exhibit at least one distinct feature. In one aspect, the identification fibers consist of 1 to 50 groups of the distinguishable identification fibers with each group of distinguishable identification fibers being formed by the identification fibers having the same distinct feature or the same combination of distinct features. In another aspect the number of groups of distinguishable identification fibers ranges from 1 to 25, 1 to 15, 1 to 10, 2 to 25, 2 to 20, 2 to 15, 3 to 24, or 3 to 15.

Groups of distinguishable identification fibers can contain one or more identification fibers having the same distinct feature for the same combination of distinct features. The number of the identification fibers in each group of the distinguishable identification fibers is defined as a fiber count. The fiber count is the actual number of fibers in each group of distinguishable identification fibers. The fiber count corresponds to a taggant fiber count. One skilled in the art recognizes that if there were no variability in manufacturing and no variability in detection, the fiber count would always equal its corresponding taggant fiber count. A robust system for building code into fibers must account for the fact that there is variability. One skilled in the art recognizes that if more than one taggant fiber count is to be used, the two or more taggant fiber counts must be different enough to allow for normal variation in the manufacture and detection of identification fibers and provide a high probability of a correct matching of fiber counts to taggant fiber counts. For example, if the normal variation in fiber counts is +−20%, taggant fiber counts of 20, 40, and 70 may provide correct matching with very high probability.

In one aspect, the fibers, yarn, or fiber band can have taggant fiber counts which correspond to the numbers of fibers (e.g., fiber counts) for each group of distinguishable identification fiber that can be present in the fibers, yarn, or fiber band. The taggant fiber counts of each group of distinguishable identification fiber can be the same or different. In one aspect, taggant fiber counts can be correlated to supply chain information. Also, the number of taggant fiber counts of each group of the distinguishable identification fibers can be the same or different. The taggant fiber counts and the number of taggant fiber counts are selected, in part, based upon the ability to manufacture and reliably detect discrete numbers of each group of the distinguishable identification fibers. The taggant fiber counts can also be limited by the maximum number of identification fibers desired. In one aspect, the number of taggant fiber counts ranges from 1 to 25, 1 to 15, 1 to 10, 1 to 5, 2 to 20, 2 to 15, 2 to 10, 3 to 20, 3 to 15, 3 to 10, 4 to 20, 4 to 15, or 4 to 10.

In one aspect, the distinguishable identification fibers can each exhibit one distinct feature, wherein each type of distinct feature is unique. For example, a first identification fiber can have a taggant cross-section shape, a second identification fiber can have a taggant cross-section size, and a third identification fiber can have a taggant optical property.

In another aspect, distinguishable identification fibers can each exhibit one distinct feature wherein each type of distinct feature is identical. For example a first identification fiber can have a first taggant cross-section shape, a second identification fiber can have a second taggant cross-section shape, a third identification fiber can have third taggant cross-section shape, etc.

In another aspect, distinguishable identification fibers can each exhibit one distinct feature wherein the types of distinct features can be identical or different. For example, a first identification fiber can have a first taggant optical property, a second identification fiber can have a first taggant cross-section size, a third identification fiber can have a second taggant optical property, and a fourth identification fiber can have a first taggant cross-section shape.

In one aspect, each group of distinguishable identification fibers can exhibit one distinct feature or the same combination of distinct features. For example, with 3 distinct features comprising a taggant cross-section shape, a taggant cross-section size, and a taggant optical property, the 7 possible groups of distinguishable identification fibers have the following distinct features: (1) identification fibers having taggant cross-section shape, (2) identification fibers having taggant cross-section size, (3) identification fibers having taggant optical property, (4) identification fibers having taggant cross-section shape at taggant cross-section size, (5) identification fiber having taggant cross-section shape with taggant optical property, (6) identification fibers having taggant cross-section size with taggant optical property, and (7) identification fibers having taggant cross-section shape at taggant cross-section size with taggant optical property.

The number of taggant fiber counts can be varied to produce different codes. For example, if any number from 1-25 specific distinguishable identification fibers can be present in fibers, yarn, or a fiber band (e.g. the fiber count for that group), the number of taggant fiber counts for that group of distinguishable identification fiber is 25 with 1-25 distinguishable identification fibers in each taggant fiber count. Alternatively, if either 10, 25, or 50 of a group of distinguishable identification fiber can be present in fibers, yarn, or a fiber band, the number of taggant fiber counts for that group of distinguishable identification fibers is 3 with 10, 25, or 50 of that specific distinguishable identification fibers as the possible taggant fiber count. The taggant fiber counts and numbers of taggant fiber counts for each group of distinct identification fibers give an additional element that can be correlated to supply chain information.

In another aspect, the distinguishable identification fibers comprise reference fibers. Reference fibers typically have a reference cross-section shape which is different from all of the other identification fibers and the standard fibers. Reference fibers also have a reference cross-section size. In one aspect, the number of reference fibers is larger than the fiber count of any other group of distinguishable identification fibers. In one aspect, the number of reference fibers is larger than the sum of the fiber counts of all of the other groups of distinguishable identification fibers. The cross-section sizes of distinguishable identification fibers can be characterized relative to the reference cross-section size. In one aspect, a group of distinguishable identification fibers can exhibit a relative cross-section size which can be smaller than, the same as, or larger than the reference cross-section size. In another aspect, a group of distinguishable identification fibers can exhibit a relative cross-section size which can be smaller than or larger than the reference cross-section size.

In one aspect, one or more identification fibers have one or more taggant cross-section sizes that are larger than the reference cross-section size. In one aspect, the ratio of the larger taggant cross-section sizes to the reference cross-section size ranges from 20:1 to 1.5:1, or 10:1 to 1.5:1, or 5:1 to 1.5:1, or 3:1 to 1.5:1, 20:1 to 1.3:1, or 10:1 to 1.3:1, or 5:1 to 1.3:1, or 3:1 to 1.3:1, or 20:1 to 1.1:1, or 10:1 to 1.1:1, or 5:1 to 1.1:1, or 3:1 to 1.1:1. In one aspect, one or more identification fibers have cross-section sizes that are smaller than the reference cross-section size. In one aspect, the ratio of the smaller cross-section sizes to the reference cross-section size ranges from 1:20 to 1:1.5, or 1:10 to 1:1.5, or 1:5 to 1:1.5, or 1:2 to 1:1.5, or 1:20 to 1:1.3, or 1:10 to 1:1.3, or 1:5 to 1:1.3, or 1:2 to 1:1.3, or 1:20 to 1:1.1, or 1:10 to 1:1.1, or 1:5 to 1:1.1, or 1:2 to 1:1.1.

An article can comprise the fibers, yarn, and/or a fiber band. The article is not particularly limited. Non-limiting examples of articles comprising the fibers or the fiber band include fabrics and other textile products, non-wovens, absorbent products, filters, filter rods, cigarette filters, liquid storage reservoirs, paper and/or currency. In one aspect, the article comprises a filter rod. In another aspect, the article comprises a cigarette filter. Additional non-limited examples of articles include medical items such as medical tape, bandages, or cloth, wicking devices used for vapor delivery, and pharmaceutical products including packaging.

In one aspect, the fibers, yarn, fiber band, and/or article have determinable supply chain information. The supply chain information can include manufacturer, manufacture site, manufacturing line, production run, production date, package, bale, warehouse, customer, and/or ship-to location. In one aspect, the distinct features in each group of the distinguishable identification fibers and the fiber counts are representative of at least one supply chain component of the acetate tow band In one aspect, the supply chain information comprises supply chain components. In one aspect, at least one supply chain component comprises a manufacturer of the standard fibers, a manufacture site of the standard fibers, a manufacturing line of the standard fibers, a production run of the standard fibers, a production date of the standard fibers, a package of the standard fibers, a warehouse of the standard fibers, a customer of the standard fibers, a ship-to location of the standard fibers, a manufacturer of a yarn or fiber band comprising the standard fibers, a manufacturing site of the yarn or fiber band, a manufacturing line of the yarn or fiber band, a production run of the yarn or fiber band, a production date of the yarn or fiber band, a package of the yarn or fiber band, a warehouse of the yarn or fiber band, a customer of the yarn or fiber band, a ship-to location of the yarn or fiber band, a manufacturer of an article comprising the standard fibers, a manufacture site of the article, a manufacturing line of the article, a production run of the article, a production date of the article, a package of the article, a warehouse of the article, a customer of the article, or a ship-to location of the article.

In another aspect at least one supply chain component comprises the manufacturer of the yarn or fiber band. In one aspect, the supply chain component comprises the manufacture site of the yarn or fiber band. In one aspect the supply chain component comprises the manufacturing line of the yarn or fiber band. The manufacturing line of the yarn or fiber band is the manufacturing line on which the yarn or fiber band was produced. In one aspect, the supply chain component comprises the production run of the yarn or fiber band. The production run of the yarn or fiber band is the production run within which the yarn or fiber band was produced. In one aspect, the supply chain component comprises the production date of the yarn or fiber band. The production date of the yarn or fiber band is the production date on which the yarn or fiber band was produced. In one aspect, the supply chain component comprises the package of the yarn or bale of the fiber band. In one aspect, the supply chain component comprises the warehouse of the yarn or fiber band. The warehouse of the yarn or fiber band is the warehouse to which the manufacturer plans to send or has sent the fiber band. In one aspect, the supply chain component comprises the customer of the yarn or fiber band. The customer of the yarn or fiber band is the customer to whom the manufacturer plans to send or has sent the yarn or fiber band. In one aspect, the supply chain component comprises the ship-to location of the yarn or fiber band. The ship-to location of the yarn or fiber band is the specific geographic location to which the manufacturer plans to send or has sent the yarn or fiber band.

The fibers, yarn, or fiber band can comprise determinable supply chain information. The possible number of groups of distinguishable identification fibers for identification fibers exhibiting, for example, 1-50 distinct features is great. The following non-limiting examples are intended to (1) illustrate the vast array of distinguishable identification fibers possible based upon a relatively low number of and/or combinations of distinct features and (2) illustrate varied approaches by which the distinct features in each group of the distinguishable identification fibers and the fiber counts can be representative of at least one supply chain component of the fibers, yarn, or fiber band.

Although not particularly limited, selection of the distinct features, combinations of distinct features, and coding system can be influenced by several factors. These factors include, but are not limited to, ease of manufacturing identification fibers, yarn and/or fiber bands, comprising identification fibers; ease of detecting identification fibers, either in the fibers, yarn, or fiber band or in an article comprising the fibers, yarn, or the fiber band; impact of the identification fibers on performance characteristics of an article comprising the fibers, yarn, fiber band; and ease of countering the track and trace objective.

The disclosed embodiments may also allow for flexible implementation of a coding system for correlating the identification fibers exhibiting distinct features and/or combinations of distinct features, one or more groups of distinguishable identification fibers and corresponding taggant fiber counts, as well as the number of taggant fiber counts to supply chain information. Described below are non-limiting examples of how coding systems can be readily implemented based upon the above described identification fibers.

In a non-limiting example, standard fibers are medium-sized circles and four manufacturer-specific taggants are used. A first taggant cross-section size, a second taggant cross-section size, a first taggant cross-section shape, and a second taggant cross-section shape. The manufacturer specific taggant cross-section sizes are small and large and the manufacturer specific taggant cross-section shapes are squares and triangles. In this example, eight possible groups of distinguishable identification fibers can be produced: small-sized circles (an example of taggant cross-section size), large-sized circles, small-sized squares (an example of the combination of taggant cross-section size and taggant cross-section shape), medium-sized squares (an example of taggant cross-section shape), large-sized squares, small-sized triangles, medium-sized triangles, and large-sized triangles. For example, when using a code comprised of one circle-shaped, one square-shaped, and one triangle-shaped identification fiber, eighteen sets of distinguishable identifications fibers are possible. If, additionally, one of two manufacturing-specific taggant colors are present for each identification fiber, the number of distinguishable identification fibers grows to 16 and the number of combinations grows to 144 (8 optical combinations per size/shape combinations of identification fibers times 18 size/shape combinations of identification fibers).

The example as described above also illustrates the selection of coding systems for ease of detection of each group of distinguishable identification fibers. The example coding system requires that one and only one of each taggant cross-section shape be detected in the fiber band. Once each taggant cross-section shape has been found, detection and analysis can end with confidence that all distinguishable identification fibers present have been found.

In a another example, if one circle, one square, and one triangle of the original 8 distinguishable identification fibers above are present in one of 3 taggant fiber counts (e.g., taggant fiber counts of 10, 20, or 30), the number of possible sets grows to 486.

FIG. 2 illustrates another non-limiting example of correlating distinct features to supply chain information. In this example, the groups of distinguishable multicomponent identification fibers correlates to supply chain information. The larger the set of possible combinations of distinct features (i.e., applying combinatorics), the more detailed the supply chain information correlation can be. In FIG. 2, multicomponent fibers are shown with 3 taggant segment counts (e.g., 1, 2, and 3 islands), and two taggant colors for each of the segments (islands and sea). In this example, each of the island(s) has the same taggant color within a filament and the island(s) taggant color is different from the sea taggant color. In other words, if the optical taggants are denoted by A and B, there are 2 distinguishable identification fibers for each taggant segment count, one with A color island(s) and B color sea or one with B color island(s) and A color sea (i.e., A/B or B/A). The total number of distinguishable identification fibers for 3 taggant segment counts and 2 taggant colors is 6. The 6 distinguishable identification fibers are shown in the columns labeled as 0 and 7 in FIG. 2. If only one optical taggant formation (i.e., A/B or B/A) is present for each of the 3 segment counts, as illustrated in FIG. 2, the number of possible combinations is 8, which can translate, for example, into numeric code 0-7. If one more taggant color is added, for example, such that taggant colors are A, B, and C, and only 2 taggant colors are present as described above for each identification fiber (i.e., each island in a given filament is the same taggant color and the sea has one different taggant color), the total number of distinguishable identification fibers for each taggant segment count is 6 (i.e., A/B, A/C, B/A, B/C, C/A, or C/B) for a total of 18 possible distinguishable identification fibers when three segment counts are used. Again, if only one optical taggant formation is present for each of the segment counts, then for three segment counts, the number of possible combinations for the distinguishable identification fibers is 216 which can translate into, for example, a numeric code 0-215. If, for example, the manufacturer of a fiber band has 200 customers, the customer information can be readily incorporated into the fiber band using this correlation method.

The Table below shows the increase in the number of possible identification fibers and codes as the number of segment counts increases, for both the 2 taggant color and 3 taggant color examples. As shown in the below Table below, a large number of possible combinations of distinguishable identification fibers can be generated with relatively few taggants. The combinations can translate into codes. Going beyond what is shown in the Table below, under the same assumptions discussed above, except for using four taggant colors, the number of combinations possible for 1, 3, 5, and 10 segment counts is 12, 1,728, 248,832, and 61,917,364,224, respectively.

TABLE

Example of number of possible combinations of distinguishable identification fibers when each number of islands is present in only one optical taggant formation

|  | 2 optical taggants | | 3 optical taggants - only two used in each identification fiber | |
| --- | --- | --- | --- | --- |
| Number of Islands | # possible ID Fibers | # Combinations | # possible ID Fibers | # Combinations |
| 1 | 2 | 2 | 6 | 6 |
| 1-3 | 6 | 8 | 18 | 216 |
| 1-5 | 10 | 32 | 30 | 7,776 |
| 1-10 | 20 | 1,024 | 60 | 60,466,176 |

The example as described illustrates the selection of taggants, combinations, and taggant fiber counts of taggants for ease of manufacturing the identification fibers. Simpler, and thus cheaper, multicomponent spinpacks can be used when the same taggant color is used for all of the islands of a given filament and/or set of filaments. The increase in the number of codes with taggant color allows for several different codes to be incorporated by simply changing the color to a section of one or more multicomponent spinpacks. If the article performance is not impacted by the color, this may be cheaper than having to change out spinpacks to change the number of segments (e.g., islands).

The example as described also illustrates the selection of coding systems for ease of detection of distinguishable identification fibers. The example coding system requires that there be one and only one of taggant color formation for each of the different segment counts (e.g., 1, 2, and 3 islands) and requires that each segment count is present. Once a taggant color formation has been found for each of the different segment counts, detection and analysis can end with confidence that all distinguishable identification fibers present have been found.

The method one uses for including distinct features, combinations of distinct features, taggant fiber counts, and/or number of taggant fiber counts into a code is not particularly limiting. One skilled in the art can readily see that there exists a large number of ways to generate several sets and/or codes based upon a relatively small number of distinct features, groups of distinguishable identification fibers, taggant fiber counts, and/or number of taggant fiber counts.

In a second embodiment, an acetate tow band comprises fibers comprising standard fibers and identification fibers. The standard fibers comprise cellulose acetate fibers. The identification fibers comprise multicomponent fibers, wherein each of the multicomponent fibers comprises 2 to 100 segments. Each of the identification fibers exhibits at least one distinct feature. Each of the multicomponent fibers exhibit the at least one distinct feature comprising one or more taggant segment counts, one or more taggant segment shapes, one or more taggant segment geometrical relationships, or one or more taggant segment pointers. The identification fibers comprise one or more groups of distinguishable identification fibers, each group of the distinguishable identification fibers being formed by the identification fibers having the same distinct feature or a same combination of the distinct features The number of the identification fibers in each group of the distinguishable identification fibers is defined as a fiber count and at least one of the fiber counts corresponds to a taggant fiber count. The distinct features in each group of the distinguishable identification fibers and the one or more taggant fiber counts represent at least one supply chain component of the acetate tow band.

The acetate tow band of the second embodiment encompasses acetate tow bands comprising fibers with any combination of attributes disclosed above. Specifically, the identification fiber composition, the sizes and numbers of fibers, the percentage of distinct features in a fiber band, the distinct features, the number of distinct features, the combinations of distinct features, groups of distinguishable identification fibers, fiber counts, descriptions of cross-section shapes, cross-section sizes, optical properties, surface markings, multicomponent fibers, segment counts, segment shapes, segment sizes, segment geometries, descriptions of segment pointers, the number of identification fibers, the variation among fibers, the supply chain information, and the non-limiting coding/correlation systems apply to the acetate tow band of the second embodiment.

In a third embodiment, a method for making fibers comprising identification fibers comprises spinning one or more polymers into the multicomponent fibers using one or more multicomponent spinpacks. The identification fibers comprise multicomponent fibers, wherein each of the multicomponent fibers comprises 2 to 100 segments. Each of the identification fibers exhibits at least one distinct feature. Each of the multicomponent fibers exhibit the at least one distinct feature comprising one or more taggant segment counts, one or more taggant segment shapes, one or more taggant segment geometrical relationships, or one or more taggant segment pointers. The identification fibers comprise one or more groups of distinguishable identification fibers, each group of the distinguishable identification fibers being formed by the identification fibers having the same distinct feature or a same combination of the distinct features The number of the identification fibers in each group of the distinguishable identification fibers is defined as a fiber count and at least one of the fiber counts corresponds to a taggant fiber count. The distinct features in each group of the distinguishable identification fibers and the one or more taggant fiber counts establish a code of the fibers.

The identification fibers can be combined with standard fibers into a yarn or fiber band. The method for making a yarn or fiber band encompasses making fibers, a fiber band, or yarn comprising the fibers with any combination of attributes disclosed above. Specifically, the identification fiber composition, the sizes and numbers of fibers, the percentage of distinct features in a fiber band, the distinct features, the number of distinct features, the combinations of distinct features, groups of distinguishable identification fibers, fiber counts, descriptions of cross-section shapes, cross-section sizes, optical properties, surface markings, multicomponent fibers, segment counts, segment shapes, segment sizes, segment geometries, descriptions of segment pointers, the number of identification fibers, the variation among fibers, the supply chain information, and the non-limiting coding/correlation systems applied to the above apply equally well to the method for making identification fibers.

In one aspect, at least a portion of the standard fibers are produced on a fiber production process. In another aspect, standard fibers are received from a third party. Obtaining the identification fibers comprises at least one of (i) producing at least a portion of the identification fibers on the standard fibers' fiber production process, (ii) producing at least a portion of the identification fibers on a process distinct from the standard fibers' fiber production process, or (iii) receiving at least a portion of the identification fibers from a third party.

In one aspect, a portion of the identification fibers are coproduced with the standard fibers and a portion of the fibers making up a fiber band or yarn are spun and combined directly downstream of the fiber production process. One skilled in the art will recognize that this can be done by imparting distinct features to groups of identification fibers, such as distinct cross-section shapes or cross-section sizes imparted to a portion of the fibers from a given spinneret or a given spinning cabinet in the fiber production line. In another aspect, distinct features can be uniformly dispersed throughout the fiber band by imparting distinct features to some or all of the fibers uniformly throughout the production line.

In another aspect, the identification fibers are produced and packaged separately from the standard fibers and the identification fibers are combined with the standard fibers to produce a fiber band or yarn. The standard fibers may also have been packaged before combining with the identification fibers, or the identification fibers may be combined with the standard fibers before packaging of the fiber band or yarn.

The spinning process used for producing the fibers is not particularly limited. In one aspect, the fibers are produced using dry spinning, solution spinning, melt spinning, electro spinning, gel spinning, multicomponent spinning, melt blowing, and/or solution blowing. In another aspect, the fibers are produced using dry spinning, solution spinning, melt spinning, electro spinning, gel spinning, and/or multicomponent spinning. In a further aspect, the fibers comprise cellulose acetate and are produced using dry spinning.

In one aspect, the distinct features comprise taggant cross-section shapes and/or taggant cross-section sizes. In one aspect, the number of identification fibers ranges from 0.01 to 50 percent of fibers, based on the total of identification fibers and standard fibers. In other examples of the number of identification fibers ranges from 0.01 to 25 percent, 0.01 to 10 percent, or 0.01 to 5 percent of the fibers.

In one aspect, the distinct features comprise taggant cross-section shapes. The taggant cross-section shapes are produced using spinneret design and process conditions including spinneret hole geometry, draft ratio, and/or mass transfer rates. One skilled in the art of fiber production recognizes how each of these factors can be manipulated to impact taggant cross-section shape. For example, spinneret holes can vary in shape from non-limiting examples of circular, square, triangular, pentagon, octagon, half circle, and three-quarter circle. In one aspect, at least a portion of the spinneret hole geometries are selected from the group consisting of triangle, circle, rectangle, square, flattened round, trapezoid, hexagon, pentagon, and D-shaped. In another aspect, at least a portion of the spinneret hole geometries are selected from the group consisting of circle, rectangle square, flattened round, trapezoid hexagon, pentagon, and D-shaped The draft ratio can also impact the shape. Finally, in spinning processes that include the mass transfer of a solvent or other material the polymer of the fiber, one skilled in the art recognizes that process conditions which impact the rate of mass transfer, such as temperature and gas flow, can impact taggant cross-section shape. In another aspect, at least a portion of the spinneret hole geometries are selected from the group consisting of circle, rectangle square, flattened round, trapezoid hexagon, pentagon, and D-shaped.

In one aspect, the distinct features comprise taggant cross-section sizes. The taggant cross-section sizes are produced using design and process conditions including spinneret hole geometry, extrusion flow rate, draft ratio, and/or solids level. When each of the other design and process conditions is held constant, one skilled in the art recognizes the impact of a change in one factor on taggant cross-section size. For example taggant cross-section size increases with increased spinneret hole size. Taggant cross-section size increases with increased extrusion rate. Taggant cross-section size decreases with increased draft ratio. Finally, taggant cross-section size increases with increased solids.

In one aspect, the identification fibers consist of 1 to 50 groups of distinguishable identification fibers, each group of the distinguishable identification fibers being formed by the identification fibers having the same distinct feature or combination of distinct features. The number of the identification fibers in each group of the distinguishable identification fibers is defined as a fiber count. The distinct features in each group of the distinguishable identification fibers and the fiber counts are representative of at least one supply chain component of the acetate tow band.

In one aspect, the single-component identification fibers are produced using distinguishable spinneret holes, each group of the distinguishable spinneret holes being formed by spinneret holes having the same distinguishable spinneret hole geometry. Each group of the distinguishable identification fibers are produced using a corresponding group of the distinguishable spinneret holes. There is a one-to-one relationship between a specific distinguishable spinneret hole geometry and a specific distinguishable identification fiber produced using the specific distinguishable spinneret hole geometry. The number of each of the distinguishable spinneret holes used to make a corresponding group of distinguishable identification fibers is equal to the fiber count for the corresponding group of distinguishable identification fibers.

The spinneret configuration for producing identification fibers is not particularly limiting. In one aspect, all of the identification fibers are produced from a single spinneret or from multiple spinnerets in a single spinning cabinet Such a configuration can concentrate the identification fibers in a single region of the tow band or article, depending on the band and/or article production arrangement, allowing for more efficient and effective location and characterization of the identification fibers. In another aspect, identification fibers are produced from multiple spinnerets or from multiple spinnerets in multiple spinning cabinets. Such a configuration can allow for higher total counts of identification fibers or could improve overall spinnanability of the identification fibers by reducing concentration of the identification fibers being produced from any one spinneret.

Different groups of the distinguishable identification fibers can be produced from separate spinnerets or from several spinnerets in various combinations. For example, each group of distinguishable identification fibers can be produced using a spinneret different from the one used to produce every other group of the distinguishable identification fibers. Such a configuration might allow for improved spinnability of the identification fibers through the optimization of the spinneret and/or the spinning conditions for each group of the distinguishable identification fibers. In another aspect, all groups of the distinguishable identification fibers can be produced from the same spinneret. Such a configuration might allow for reduced variation in the shape or size of the distinguishable identification fibers.

The arrangement of the distinguishable spinneret holes with distinguishable spinneret hole geometry on a particular spinneret is not particularly limiting. In one aspect, all of the holes having a particular spinneret hole geometry can be arranged in the same row or in adjacent rows, or could be arranged in the same concentric ring or adjacent concentric rings, or can be grouped in a specific region of the spinneret. Such configurations may improve the spinnability of the identification fibers or reduce the variation of the shape or size of a distinguishable identification fiber, thereby enabling improved characterization. In another aspect, distinguishable spinneret holes for each group of the distinguishable identification fibers can be distributed uniformly in various patterns, or can be distributed randomly with standard spinneret holes.

In one aspect, one or more distinct features comprise taggant optical properties. The taggant optical properties can be produced by incorporating a substance, for example, fluorescent compounds and/or dyes, in one or more identification fibers. In one aspect, the substance is applied to the surface of one or more identification fibers. The method for applying the substance to the surface of one or more identification fibers is not particularly limited and includes dipping, immersing, submerging, soaking, rinsing, washing, painting, coating, showering, drizzling, spraying (as liquid or atomized), placing, dusting, sprinkling, affixing, pouring, and/or direct metering.

In one aspect, the substance is added to the spinning solution. The spinning solution is subsequently spun into one or more identification fibers. The substance can be added to the spinning solution upstream of the production line, spinning cabinets, and/or individual spinnerets.

In one aspect, one or more distinguishable identification fibers comprises multicomponent fibers. The number of multicomponent fibers, the segment counts in each of the multicomponent fibers, the segment geometrical relationships, and the segment pointers are produced using specific multicomponent spinpack configurations. In one aspect, the multicomponent spinpack is configured to be able to change the polymers going to different segments of a portion of the identification fibers without switching out the multicomponent spinpack. This can allow the implementation of several potential codes without the labor and expense of changing out the multicomponent spinpack. In one aspect, multicomponent distinguishable identification fibers comprising different numbers of segments are produced within a single multicomponent spinpack. In one aspect, identification fibers comprise islands and sea and wherein a portion of the identification fibers are produced with the islands comprising a first polymer and the sea comprising a second polymer and a different portion of the identification fibers are produced with the islands comprising the second polymer and the sea comprising the first polymer. In one aspect, changing the first polymer or the second polymer from the island to the sea or from the sea to the island for at least a portion of the identification fibers does not require changes to the multicomponent spinpack.

In one aspect, the disclosed embodiments provide a multicomponent spinpack capable of producing 1 to 200, 1 to 100 or 1 to 50 multicomponent fibers. In one aspect, the multicomponent spinpack is connected to a manifold system that allows switching among various polymers to feed the various segments.

In one aspect the number of groups of the distinguishable identification fibers ranges from 1 to 25, 1 to 15, 1 to 10, 2 to 20, 2 to 15, 3 to 20, and 3 to 15.

Non-limiting examples of specific multicomponent fiber sets and a means for switching the polymer in the island versus the sea are given in FIG. 3 through FIG. 4.

FIG. 3(a) illustrates multicomponent fiber spinpack 200 capable of producing fourteen multicomponent distinguishable identification fibers. Each of the fibers comprises at least one island and sea. For example, as shown in FIG. 3(a), an island is produced from polymer extruded through small circle 230 and sea is produced from the polymer extruded through the area surrounding the small circles 240. In addition to illustrating different numbers of islands FIG. 3(a) illustrates different segment geometrical relationships as seen in comparing the designs of sections 220(a) and 220(b).

Figure 3B:
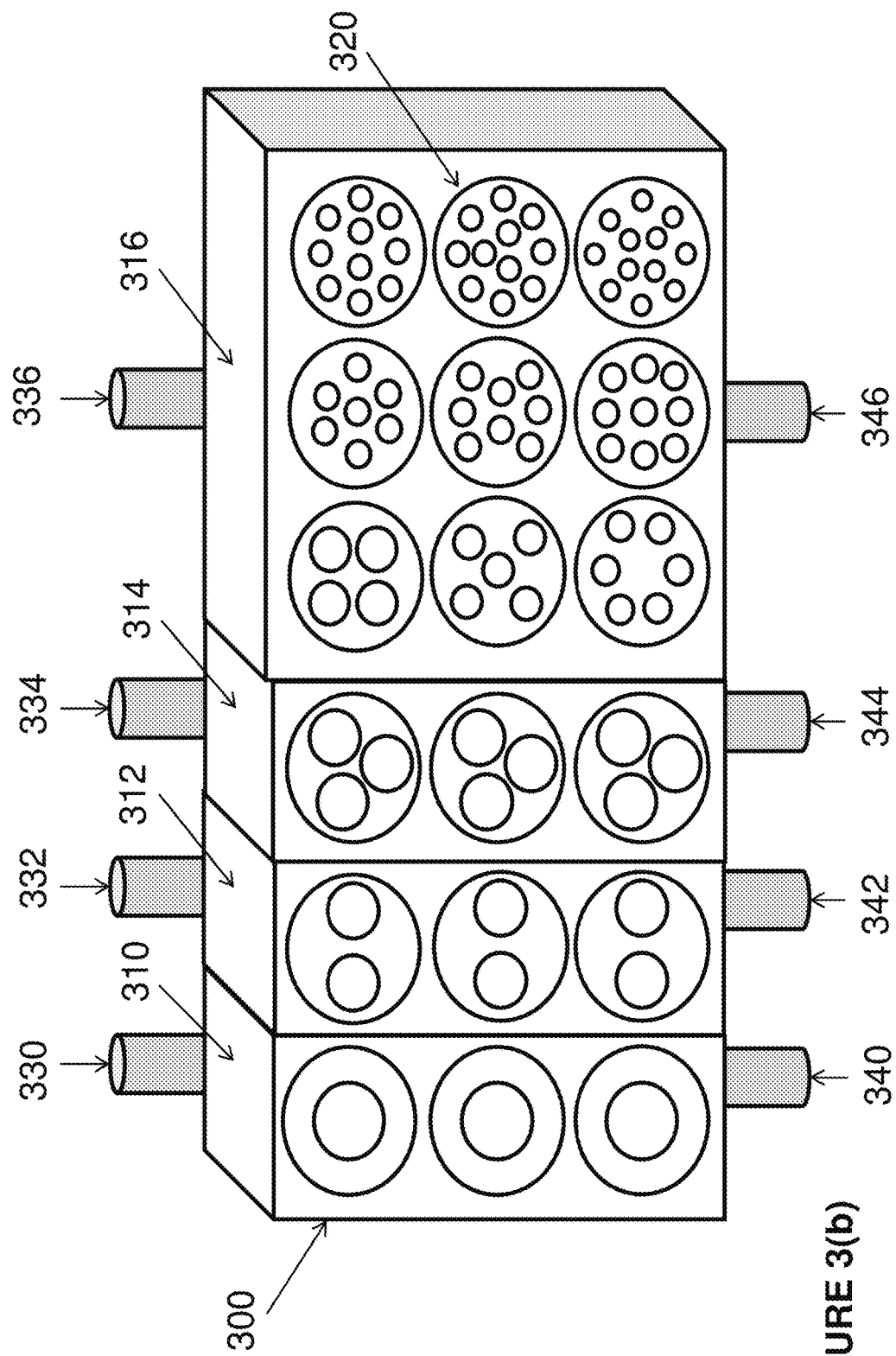
Figure 4A:
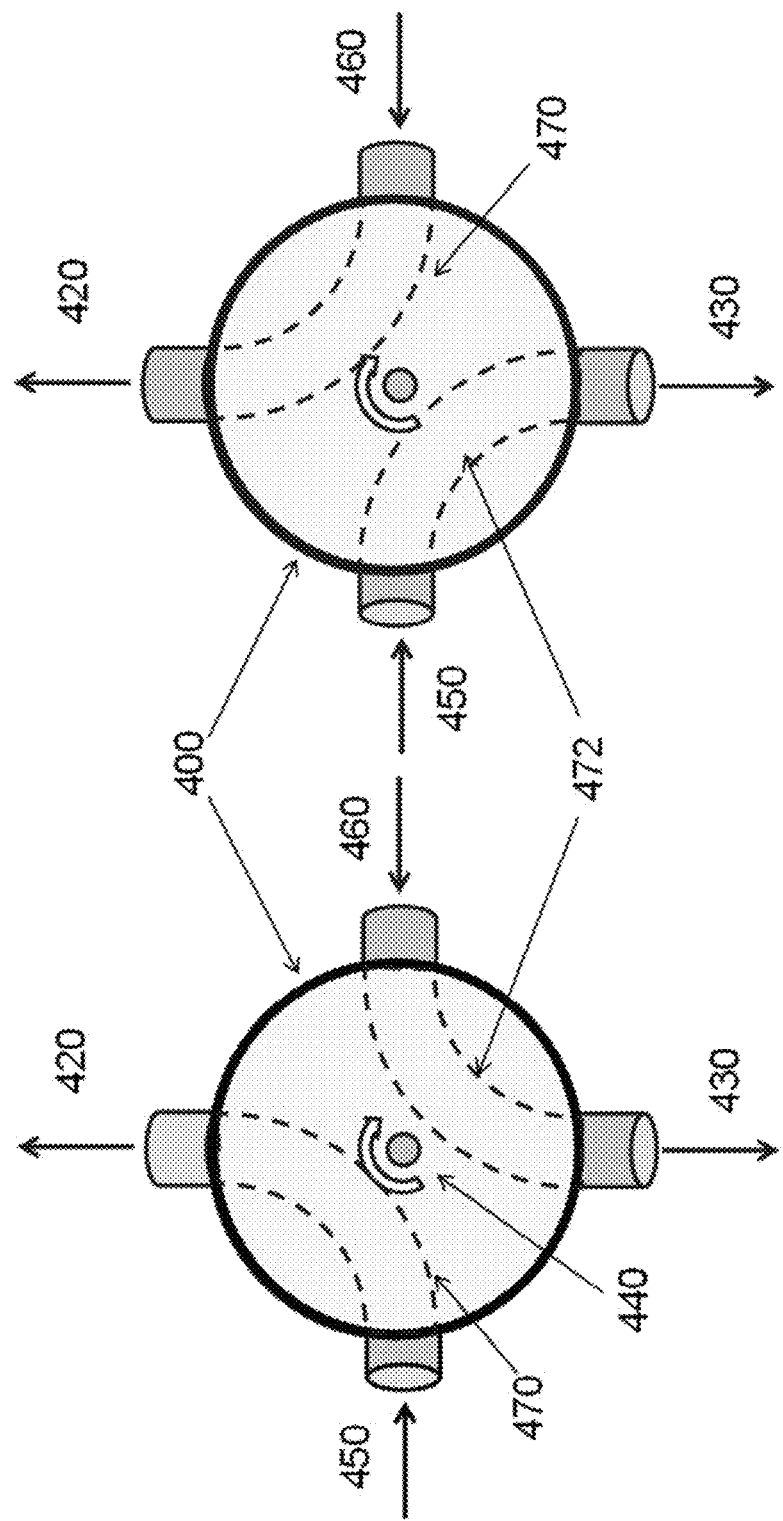
FIGS. 4(a) and 4(b) illustrates a non-limiting example of a polymer feed system which allows for ready exchange of polymers between segments of multicomponent fibers.
Figure 4B:
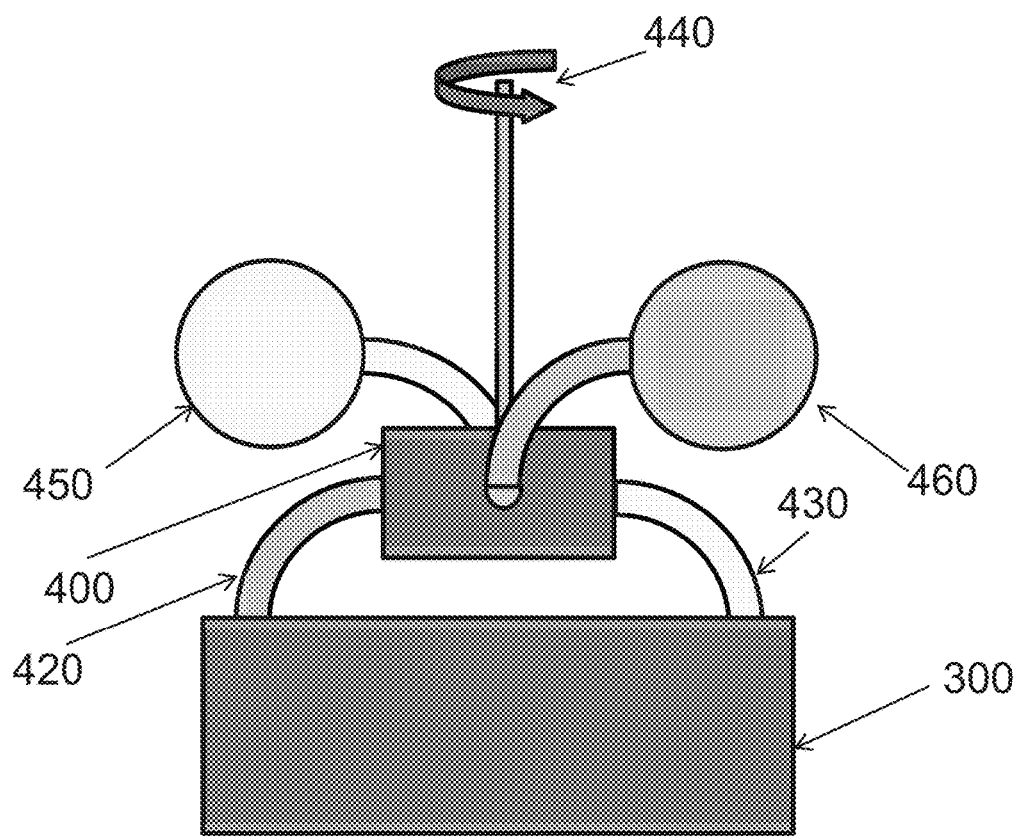

FIGS. 3(b), 4(a), and 4(b) illustrate a non-limiting example of a multicomponent spinpack system wherein the polymer of the islands and the polymer of the sea can be independently exchanged for subsets of the multicomponent fibers. Multicomponent fiber spinpack 300 contains four sections for producing eighteen multicomponent fibers 320. Each section, 310, 312, 314 and 316 comprises independent polymer feeds for the islands and the sea of each multicomponent fiber produced. Section 310 can be used to produce three multicomponent fibers with one island. In one example, polymer feed 330 extrudes through the islands and polymer feed 340 extrudes through the sea. Section 312 can be used to produce three multicomponent fibers with two islands. In one example, polymer feed 332 extrudes through the islands and polymer feed 342 extrudes through the sea. Section 314 can be used to produce three multicomponent fibers with three islands. In one example, polymer feed 334 extrudes through the islands and polymer feed 344 extrudes through the sea. Section 316 can be used to produce nine multicomponent fibers with four to twelve islands in each fiber. In one example, polymer feed 336 extrudes through the islands and polymer feed 346 extrudes through the sea.

In one aspect, the polymer feeds can be readily exchanged between islands in the sea in any section of multicomponent fiber spinpack 300. FIG. 4(a) illustrates valve 400 providing flow paths for polymers 450 and 460. In a first configuration, polymer 450 exits outlet 420 via connection 470 and polymer 460 exits outlet 430 via connection 472. FIG. 4(a) illustrates a second configuration wherein polymer 450 exits outlet 430 via connection 472 and polymer 460 exits outlet 420 via connection 470. Switch 440 can be turned to alternate the inlet/outlet configuration, to configure flow path 470 between polymer inlet 450 and outlet 420 and flow path 472 between polymer 460 inlet and 430 outlet; or alternatively, to configure flow path 472 between polymer inlet 450 and outlet 430 and flow path 470 between polymer 460 inlet and 420 outlet. Outlet 420 can be connected to feed the islands and outlet 430 can be connected to feed the seas of a multicomponent fiber spinpack not shown. FIG. 4(b) illustrates the connection of the reservoir of polymer 450 and polymer 460 to multicomponent fiber spinpack 300 through valve 400. Switch 440 is set to allow polymer 450 to flow through outlet 430 to spinpack 300 (e.g., to feed the islands not shown) and polymer 460 to flow through outlet 420 to spinpack 300 (e.g., to feed the seas not shown).

In one aspect, the identification fibers comprise 1 to 50 groups of distinguishable identification fibers, each group of the distinguishable identification fibers being formed by the identification fibers having the same distinct feature or combination of distinct features. The number of the identification fibers in each group of the distinguishable identification fibers is defined as a fiber count. In one aspect, each of the distinguishable identification fibers are produced using a distinguishable spinneret hole or a multicomponent spinpack. Each of the distinguishable spinneret holes exhibit a distinguishable spinneret hole geometry. In one aspect the number of distinguishable identification fibers ranges from 1 to 25, 1 to 15, 1 to 10, 2 to 20, 2 to 15, 3 to 20, and 3 to 15.

In one aspect, distinguishable identification fibers comprise a reference fiber. The reference fibers comprises a reference cross-section size and a reference cross-section shape. The reference fibers are produced using distinguishable spinneret holes comprising reference spinneret holes. In one aspect, the number of reference fibers is larger than the number of each other of the distinguishable identification fibers. In one aspect, the number of reference fibers is larger than the number of all other of the distinguishable identification fibers.

The reference fibers can serve to differentiate, for example, large and small sizes of the same cross-section shape. In one aspect, the geometry of the distinguishable spinneret holes is selected relative to the geometry of the reference spinneret hole. In one aspect, the distinguishable identification fibers, excluding the reference fibers, exhibit taggant cross-section sizes either smaller than, the same as, or larger than the cross-section size as determined by effective diameter.

In one aspect the number of reference fibers is selected such that the total number of all distinguishable identification fibers equals a taggant total identification fiber number.

In a fourth embodiment, a method of characterizing a fiber sample comprising (1) applying imaging technology to the fiber sample, (2) detecting the groups of the distinguishable identification fibers, and (3) counting a number of each of the distinguishable identification fibers. The fiber sample comprises fibers, wherein the fibers comprise identification fibers and standard fibers. The identification fibers comprise multicomponent fibers, wherein each of the multicomponent fibers comprises 2 to 100 segments. Each of the identification fibers exhibits at least one distinct feature. Each of the multicomponent fibers exhibit the at least one distinct feature comprising one or more taggant segment counts, one or more taggant segment shapes, one or more taggant segment geometrical relationships, or one or more taggant segment pointers. The identification fibers comprise one or more groups of distinguishable identification fibers, each group of the distinguishable identification fibers being formed by the identification fibers having the same distinct feature or a same combination of the distinct features The number of the identification fibers in each group of the distinguishable identification fibers is defined as a fiber count and at least one of the fiber counts corresponds to a taggant fiber count. The distinct features in each group of the distinguishable identification fibers and the one or more taggant fiber counts represent at least one supply chain component of the of the fiber sample.

The method for testing a fiber sample encompasses testing a fiber sample comprising the fibers with any combination of attributes disclosed above. The fiber sample can comprise fibers, a portion of a fiber band, a portion of a yarn, or a portion of an article. Specifically, the identification fiber composition, the sizes and numbers of fibers, the percentage of distinct features in a fiber band, the distinct features, the number of distinct features, the combinations of distinct features, groups of distinguishable identification fibers, fiber counts, descriptions of cross-section shapes, cross-section sizes, optical properties, surface markings, multicomponent fibers, segment counts, segment shapes, segment sizes, segment geometries, descriptions of segment pointers, the number of identification fibers, the variation among fibers, the supply chain information, and the non-limiting coding/correlation systems above apply equally well to the fourth embodiment. Also, the fiber sample can comprise the acetate tow band of the second embodiment with any combinations of its features or filter comprising the acetate tow band.

In one aspect, the fiber counts are added to calculate a taggant total identification fibers number.

In one aspect, the imaging technology comprises the use of electromagnetic radiation at visible wavelengths. In another aspect, the image technology comprises the use of electromagnetic radiation at invisible wavelengths. The equipment useful for imaging technology is not particularly limited. Non-limiting examples include human visual inspection, microscopy, electron microscopy, confocal microscopy, fluorescence microscopy, and optical scanning.

The imaging technology can be applied to the fiber sample transverse to the length of the fibers. This direction allows, for example, a view of the cross-section shapes of the fibers. The imaging technology can also be applied along the length of fibers. This direction allows, for example, a view of a pattern of surface markings on the fibers.

The preparation of the fiber band, yarn, and/or one or more fibers for application of the imaging technology is not particularly limiting. In one aspect, the fibers are incorporated into a matrix prior to applying the imaging technology. For example, fibers can be immobilized in a polymer that does not interfere with the imaging technology and cut into appropriate sample sizes.

The imaging technology may also be applied to the article comprising the fibers, fiber band, or yarn.

In one aspect, the method for characterizing the fiber sample further comprises (a) correlating the distinct features in each group of the distinguishable identification fibers and the one or more taggant fiber counts to a database comprising manufacturer-specific taggants; and (b) determining at least one supply chain component of the fiber sample. The supply chain component comprises a manufacturer of the standard fibers, a manufacture site of the standard fibers, a manufacturing line of the standard fibers, a production run of the standard fibers, a production date of the standard fibers, a package of the standard fibers, a warehouse of the standard fibers, a customer of the standard fibers, a ship-to location of the standard fibers, a manufacturer of a yarn or fiber band comprising the fibers, a manufacturing site of the yarn or fiber band, a manufacturing line of the yarn or fiber band, a production run of the yarn or fiber band, a production date of the yarn or fiber band, a package of the yarn or fiber band, a warehouse of the yarn or fiber band, a customer of the yarn or fiber band, a ship-to location of the yarn or fiber band, a manufacturer of an article comprising the fibers, a manufacture site of the article, a manufacturing line of the article, a production run of the article, a production date of the article, a package of the article, a warehouse of the article, a customer of the article, or a ship-to location of the article. In one aspect the correlating is among the distinct features and/or the combinations of distinct features. In another aspect, the correlating is among the distinct features, the combinations of distinct features, and/or the total number of each of the distinguishable identification fibers. In another aspect, the correlating is among the distinct features, the combinations of distinct features, the total number of each of the distinguishable identification fibers, and/or the taggant total identification fiber number. In one aspect, at least one supply chain component comprises a manufacturer of a yarn comprising the fibers, a manufacturing site of the yarn, a manufacturing line of the yarn, a production run of the yarn, a production date of the yarn, a package of the yarn, a warehouse of the yarn, a customer of the yarn, a ship-to location of the yarn.

In one aspect, the supply chain information comprises the manufacturer of the yarn or fiber band. In one aspect, the supply chain information comprises the manufacture site of the yarn or fiber band. In one aspect the supply chain information comprises the manufacturing line of the yarn or fiber band. The manufacturing line of the yarn or fiber band is the manufacturing line on which the yarn or fiber band was produced. In one aspect, the supply chain information comprises the production run of the yarn or fiber band. The production run of the yarn or fiber band is the production run within which the yarn or fiber band was produced. In one aspect, the supply chain information comprises the production date of the yarn or fiber band. The production date of the yarn or fiber band is the production date on which the yarn or fiber band was produced. In one aspect, the supply chain information comprises the bale of the yarn or fiber band. In one aspect, the supply chain information comprises the customer of the yarn or fiber band. The customer of the yarn or fiber band is the customer to whom the manufacturer plans to send or has sent the yarn or fiber band. In one aspect, the supply chain information comprises the ship-to location of the yarn or fiber band. The ship-to location of the yarn or fiber band is the specific geographic location to which the manufacturer plans to send or has sent the yarn or fiber band.

When determining the supply chain information of a yarn, fiber band, and/or an article comprising the yarn or fiber band, the fibers to be analyzed may be in raw form such as a yarn or fiber band, (a collection of fibers) or tow (a crimped fiber band). Additionally, the article can be in a finished form such as a cylindrical filter (cigarette), a pleated filter, a fabric or a non-woven material. A goal of identifying the fibers, yarn, or the fiber band is to prevent counterfeiting, and/or illicit sales, of articles by enabling the identification of supply chain information from testing the yarn, fiber band and/or the article.

The disclosed embodiments also include making an article with fibers, a fiber band, and/or yarn having any of the disclosed features. The disclosed embodiments further include of characterizing an article comprising a fibers, fiber band, or yarn having any of the disclosed features.

Figure 5A:
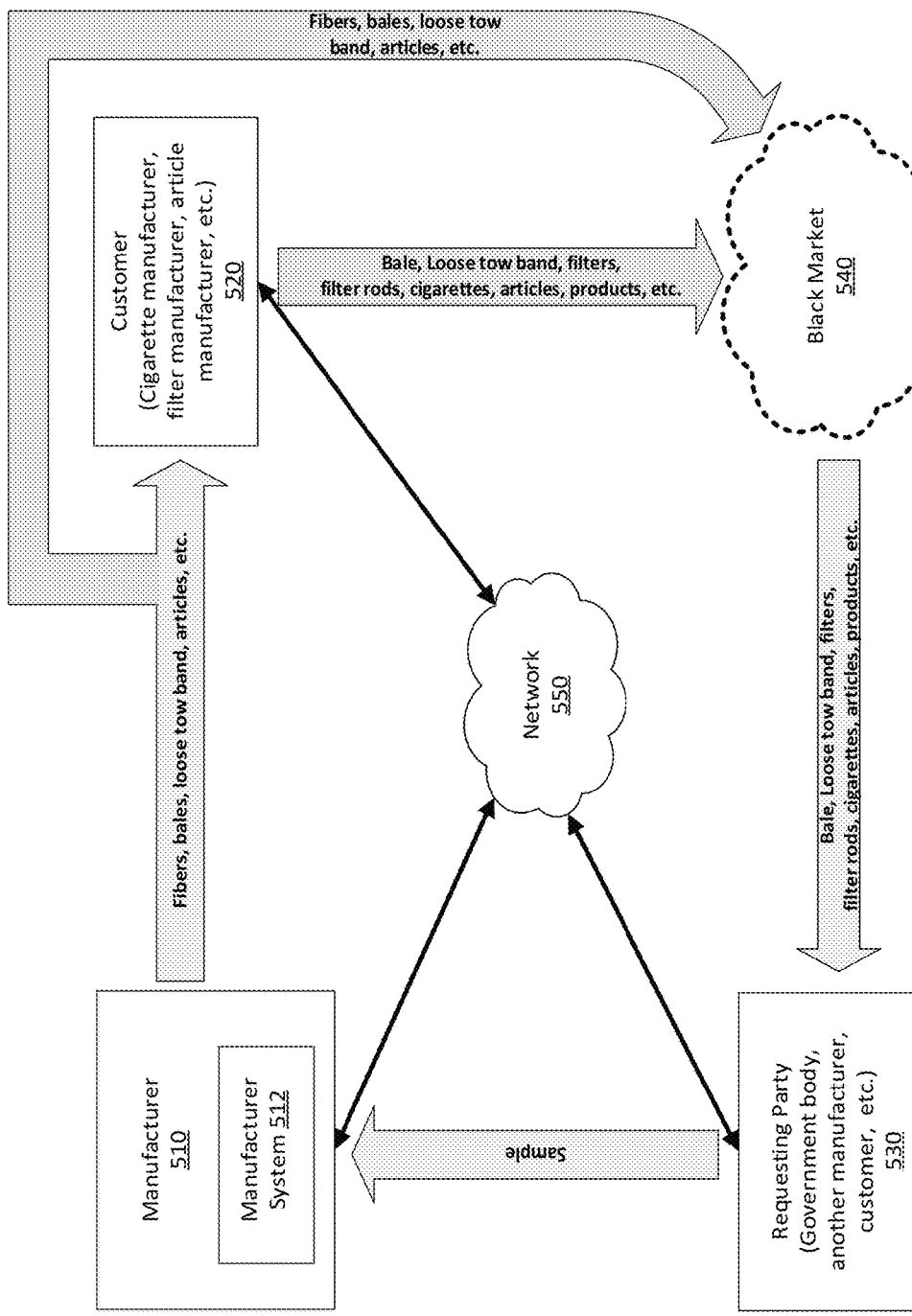
FIGS. 5A and 5B illustrate non-limiting examples of communication and shipping channels among one or more entities consistent with disclosed embodiments
Figure 5B:
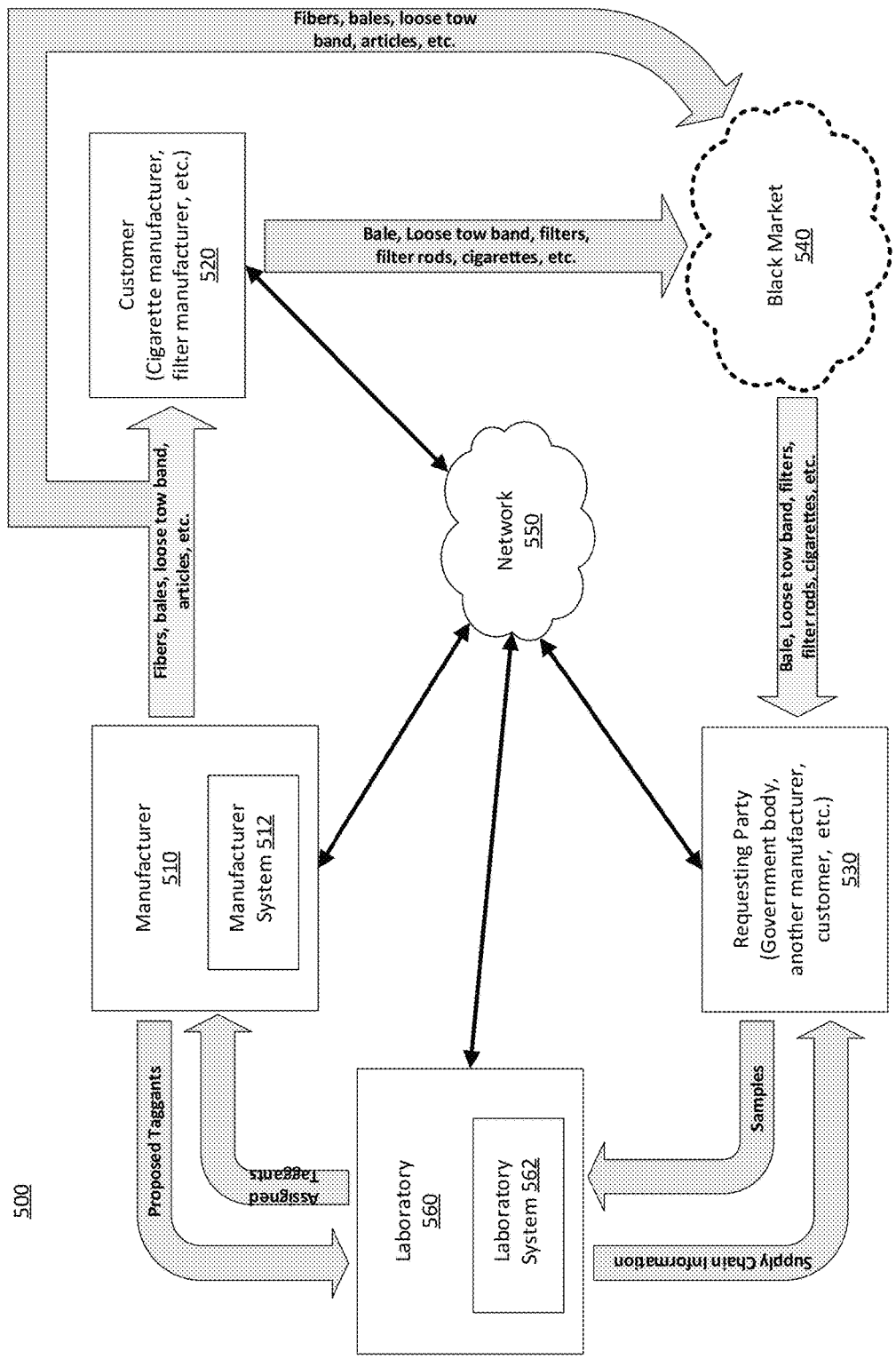

FIGS. 5A and 5B illustrate non-limiting examples of an environment 500 depicting communication and shipping channels among entities consistent with disclosed embodiments. In one embodiment, environment 500 of FIGS. 5A and 5B may include one or more manufacturers 510, one or more customers 520, a black market 540 or other illicit trade network, one or more requesting parties 530, one or more laboratories 560, and communication network 550. The components and arrangement of the components included in environment 500 (e.g., as illustrated in FIGS. 5A and 5B) may vary. Thus, environment 500 may include other components that perform or assist in the performance of one or more processes consistent with the disclosed embodiments.

In some aspects, network 550 may be any type of network configured to provide communication means between systems of components of environment 500 (e.g., manufacturing system 512 and/or laboratory system 562). For example, network 550 may be any type of network (including infrastructure) that facilitates communications, exchanges information, etc., such as the Internet, a Local Area Network, near field communication, and/or other suitable connection(s) that enables the sending and receiving of information between the component systems associated with environment 500. In other embodiments, one or more component systems of environment 500 may communicate directly through a dedicated communication link(s), such as links between manufacturer 510, customer 520, requesting party 530, and/or laboratory 560.

Further, and as stated above, manufacturers (e.g., manufacturer 510) may produce cellulose acetate fibers and fiber products that incorporate the cellulose acetate fibers on an industrial scale. In some embodiments, the produced cellulose acetate fibers and fiber products may include standard fibers and identification fibers. Each of the identification fibers exhibits one or more distinct features (e.g., distinct cross-section sizes, distinct cross-section shapes, distinct optical properties, and additionally or alternatively, distinct surface markings, such as a script, a digital code, an analog code, or a pictograph and repeating surface patterns) that visually distinguish the identification fibers from the standard fibers. In additional aspects, the identification fibers may include groups of distinguishable identification fibers that exhibit the same distinct feature or the same combination of the distinct features. Further, in some aspects, the identification fibers may include multi-component fibers having two or more distinguishable segments per filament. The multi-component identification fibers may, for example, exhibit additional distinct features (e.g., taggant segment counts, taggant segment geometrical relationships, and/or taggant segment points) that further distinguish the multi-component identification fibers from the standard fibers (and additionally or alternatively, from single-filament identification fibers). In additional aspects, each of the groups may be associated with a corresponding number of the distinguishable identification fibers, defined as the fiber count which may correspond to a taggant fiber count. In some aspects a number of taggant fiber counts may be associated with each group of the distinguishable identification fibers.

In some embodiments, the inclusion of identification fibers in the cellulose acetate fibers may enable manufacturer 510 to tag the cellulose acetate fibers, and thus, the fiber products that include the cellulose acetate fibers, with supply chain information prior to shipment to customers 520. By way of example, fiber products consistent with the disclosed embodiments may include, but are not limited to, cellulose acetate tow, loose bands of cellulose acetate tow, bales of cellulose acetate tow, and fabrics and other articles that include the cellulose acetate fibers and/or tow.

For example, and in the context of cigarette manufacturing, customer 520 may use a bale of acetate tow to produce various intermediate and/or final stage products (e.g., loose tow band, filter rods, filters, and/or cigarettes) and a fraction of these products can ultimately find their way onto the black market (e.g., black market 440). Thus, because supply chain information can be determined from a sample of any black market product having tagged identification fibers, a party interested in combating illicit trade (e.g., requesting party 530) may obtain a black market product and submit a sample for analysis in order to identify supply chain information associated with the black market product.

Thus, in one embodiment, requesting party 530 may provide the sample to manufacturer 510, as depicted in FIG. 5A. Manufacturer 510 may, in certain aspects, analyze the sample to identify at least one component of a supply chain associated with the sample. For example, the sample may include standard and identification fibers, and in some instances, manufacturer 510 may analyze the sample using any of the exemplary techniques outlined above.

Based on the analysis, manufacturer 510 may identify groups of distinguishable identification fibers that exhibit corresponding distinct features or combinations of distinct features. As noted above, the distinct features include, but are not limited to, cross-section size and/or cross-section shape. Manufacturer 510 may also identify the fiber count, the number of identification fibers in each of the groups of distinguishable identification fibers. Manufacturer 510 may also establish a number of taggant fiber counts for the exhibited groups of distinguishable identification fibers that, in some instances, represent the number of the taggant fiber counts alternatives available for each group of the distinguishable identification fibers.

In certain aspects, manufacturer 510 may access correlation data mapping components of the supply chain to the exhibited distinct features, combinations of distinct features and/or the established taggant fiber counts. Manufacturer 510 may identify the at least one component of the supply chain based on, for example, a comparison of the exhibited distinct features, combinations of distinct features and/or the established taggant fiber counts to the accessed correlation data. In some instances, manufacturer 510 may transmit information identifying the at least one supply chain component to requesting party 530 (e.g., across network 550).

In further embodiments, the accessed correlation data may map the supply chain components to not only the exhibited distinct features, combinations of distinct features, the taggant fiber counts, but also to a number of taggant fiber counts for each group of distinguishable identification fibers. Thus, in some aspects, manufacturer 510 may also establish (i.e., count) the number of the distinguishable identification fibers included within each of the groups and determine the corresponding taggant fiber count, and may identify the at least one component of the supply chain based on, for example, a comparison of the exhibited distinct features, combinations of distinct features, the established taggant fiber counts, and/or the number of taggant fiber counts to the accessed correlation data.

In other embodiments, and as described above, the distinguishable identification fibers may include one or more multi-component fibers having two or more distinguishable segments per filament. The distinguishable segments may correspond to distinct polymer compositions, which may be identified within a filament cross-section using any of the exemplary analytical techniques described above. In certain aspects, a manufacturer (e.g., manufacturer 510) may tailor one or more of the distinct polymer compositions to suit aesthetic and functional requirements for numerous applications and further, to produce fibers with unique optical or physical properties that identify one or more components of the supply chain. For example, the distinguishable segments may represent distinct polymer compounds, polymer compounds having distinct additives, and/or polymer compounds having distinct physical characteristics (e.g., distinct degrees of crystallinity).

Further, in some aspects, multi-component fibers consistent with the disclosed embodiments may include various numbers of distinguishable segments (e.g., two, three, four, etc.) disposed at various locations within the filament cross-sections and oriented relative to various physical features of the multi-component fibers. In some instances, and as described above, the distinguishable segments may be disposed within the filament cross-section in a sheath/core orientation, in an "islands in the sea" orientation, in a side-by-side orientation, and/or in a segmented-pie orientation. The disclosed embodiments are, however, not limited to these exemplary orientations, and in further embodiments, the distinguishable segments may be disposed within the filament cross-section in any additional or alternate orientation appropriate to the multi-component fibers and distinguishable using any of the analytical and/or imaging technologies outlined above.

In certain aspects, groups of distinguishable, multi-component identification fibers may exhibit combinations of the exemplary distinct features outlined above, which include, but are not limited to, cross-section size, cross-section shape, optical properties, and/or surface markings. In other aspects, however, the distinguishable, multi-component identification fibers may exhibit or be associated with additional distinct features that further distinguish these multi-component identification fibers from standard fibers (and additionally or alternatively, from single-filament identification fibers).

For instance, the distinct features characterizing the distinguishable multi-component identification fibers may include taggant segment counts that identify a number of groups of multi-component fibers that include corresponding ones of the numbers of distinguishable segments. In additional instances, the distinct features may include taggant segment geometrical relationships that indicate, for each of the distinguishable multi-component identification fibers, a relative location and orientation of the corresponding distinguishable segments within a filament cross-section. Further, in other instances, the distinct features may include taggant segment pointers that identify, for each of the distinguishable multi-component identification fibers, at least one physical feature that establishes a relative disposition of the corresponding distinguishable segments within the filament cross-sections.

In an embodiment, and using any of the exemplary analytical techniques outlined above, manufacturer 510 may analyze a sample of a fiber product that includes distinguishable, multi-component identification fibers (e.g., as provided by requesting party 530). Based on the analysis, manufacturer 510 may identify groups of distinguishable, multi-component identification fibers that exhibit one or more distinct features, such as cross-section size, cross-section shape, optical properties, and/or surface markings, and additionally or alternatively, one or more combinations of the distinct features. Further, and based on the analysis, manufacturer 510 may establish also taggant segments counts, taggant segment geometrical relationships, and/or taggant segment pointers that characterize the distinguishable, multi-component identification fibers.

For example, and as described above, manufacturer 510 may subject the sample to one or more imaging technologies that include, but are not limited to, human visual inspection, microscopy, electron microscopy, confocal microscopy, florescence microscopy, and optical scanning. In certain aspects, manufacturer 510 may apply the one or more imaging technologies to the fiber sample in a direction transverse to a length of at least one of the fibers of the fiber sample, and additionally or alternatively, along a length of at least one of the fibers of the fiber sample. Further, in some aspects, at least a portion of the fiber sample may be incorporated into a solid matrix prior to an application of the one or more imaging technologies to the fiber sample. For example, manufacturer 510 may immobilize the fibers of the sample (e.g., distinguishable, multi-component and/or single-component fibers) in a polymer that does not interfere with the one or more imaging technologies, and may section the polymer and immobilized fibers into sample sizes appropriate for analysis.

In additional embodiments, manufacturer 510 may access correlation data mapping components of the supply chain to combinations of the taggant segment counts, taggant segment geometrical relationships, and/or taggant segment pointers, either alone or in conjunction with combinations of the other distinct features (e.g., cross-section size, cross-section shape, optical properties, surface markings, etc.), taggant fiber counts, and/or a number taggant fiber counts. Manufacturer 510 may identify the at least one component of the supply chain based on, for example, a comparison of the combinations of the taggant segments counts, the taggant segment geometrical relationships, the taggant segment pointers, the other distinct features, the taggant fiber counts, and/or the number of taggant fiber counts. In some instances, and as described above, manufacturer 510 may transmit information identifying the at least one supply chain component to requesting party 530 (e.g., across network 550).

Further, as noted above, the distinguishable identification fibers may include reference fibers having a corresponding reference cross-section shape and a corresponding reference cross-section size. The reference cross-section may, for example, represent an average effective diameter of at least a portion of the reference fibers, and in some aspects, the reference cross-section size may exceed, or alternatively, be smaller than, the cross-section sizes of each of the other distinguishable identification fibers in the sample. Thus, in an embodiment, manufacturer 510 may determine that a cross-section size of a first group of the distinguishable identification fibers is larger than or smaller than the cross-section sizes of each of the other groups of the distinguishable identification fibers (e.g., using any of the exemplary techniques described above), and may establish the first group of the distinguishable identification fibers as the reference fibers.

In further aspects, a number of the reference fibers within the sample may exceed the numbers of the distinguishable identification fibers within the other groups of distinguishable identification fibers. Thus, in an embodiment, manufacturer 510 may count the number of identification fibers included within each of the groups of distinguishable identification fibers, determine that the number of the distinguishable identification fibers included within a first groups of the distinguishable identification fibers exceeds the numbers of the distinguishable identification fibers within one or more of the other groups of distinguishable identification fibers, and based on the determination, establish the first group of distinguishable identification fibers as the reference fibers. For example, the number of reference fibers in the sample may exceed a sum of the numbers of the distinguishable identification fibers within each other of the groups of distinguishable identification fibers, and additionally or alternatively, the number of reference fibers may exceed a maximum of the numbers of the distinguishable identification fibers included within corresponding ones of the other groups of distinguishable identification fibers.

Furthermore, correlation data consistent with the disclosed embodiments may map the supply chain components to not only the exhibited distinct features (e.g., cross-section size and/or shape, optical properties, surface markings, taggant segment counts, taggant segment geometrical relationships, and/or taggant segment pointers), combinations of the distinct features, the established taggant fiber counts, and/or the number of taggant fiber counts, but also to the number of reference fibers counted within the sample. Thus, in some aspects, manufacturer 510 may identify the at least one component of the supply chain based on, for example, a comparison of the exhibited distinct features and combinations of distinct features, the established taggant fiber counts, the number of taggant fiber counts and/or the number of reference fibers counted within the sample to the accessed correlation data.

In the exemplary embodiments described above, manufacturer 510 may analyze the sample to identify at least one component of a supply chain associated with the sample. The disclosed embodiments are, however, not limited to exemplary analyses conducted by manufacturer 510, and in further embodiments, customer 520, requesting party 530, or a third-party (not shown) may conduct the analysis for identifying supply chain information from tagged fibers.

For example, as illustrated in FIG. 5B, a laboratory 560 may act on behalf of requesting party 530 and perform the analysis on the sample to identify the at least one supply chain component associated with the sample. In some instances, laboratory 560 may represent a governmental entity, a quasi-governmental entity, or a private entity capable of performing the analysis, and requesting party 530 may contract with or retain laboratory 560 to perform the analysis on a one-time or recurring basis.

In other instances, however, laboratory 560 may be established by one of more of manufacturer 510, customers 520, and/or requesting party 530 in order to regularly and reliably identify supply chain components associated with samples taken from illicitly traded cellulose acetate fibers or fiber products that incorporate the cellulose acetate fibers (e.g., as obtained by requesting party 530 from black market 540). Laboratory 560 may, in certain aspects, perform the analysis of the sample in accordance with one or more procedures established by a manufacturer 510, customers 520, and/or requesting party 530. For example, one or more of manufacturer 510, customers 520, and/or requesting party 530 may collectively establish standardized procedures and protocols for receiving and handling samples, analyzing the samples to identify the supply chain components in an accurate and repeatable manner, and reporting portions of the identified supply chain components to manufacturer 510, customers 520, and/or requesting party 530. Further, in additional embodiments, laboratory 560 may also assign the distinct features (e.g., cross-section size and/or shape, optical properties, surface markings, taggant segment counts, taggant segment geometrical relationships, and/or taggant segment pointers), combinations of distinct features, the taggant fiber counts, and/or the number of taggant fiber counts to various components of the supply chain (e.g., manufacturers) to uniquely identify these supply chain components. In further embodiments, customer 520, requesting party 530, or a third-party (not shown) may assign this distinct features, the combinations of distinct features, the taggant fiber counts, and/or the number of taggant fiber counts to various components of the supply chain (e.g., manufacturers) to uniquely identify these supply chain components.

In one embodiment, as illustrated in FIG. 5B, requesting party 530 may provide the sample to laboratory 560. Laboratory 560 may, in certain aspects, analyze the sample to identify at least one component of a supply chain associated with the sample (e.g., a manufacturer). For example, using any of the exemplary techniques described above, laboratory 560 may analyze the sample to identify each of the groups of distinguishable identification fibers that exhibits the same distinct features and/or the same combination of distinct features, count a number of distinguishable identification fibers included within each of the groups (establishing the taggant fiber count for each group of distinguishable identification fibers), and additionally or alternatively, identify and count a number of reference fibers within the sample. Further, laboratory 560 may access correlation data, and using any of the exemplary techniques described above, identify the at least one supply chain component based on a comparison of the exhibited distinct features, combinations of distinct features, the established taggant fiber counts, the number of taggant fiber counts, and/or the number of reference fibers included within the sample to the accessed correlation data.

In additional embodiments, laboratory 560 may function as a centralized facility that assigns unique distinct features, combinations of distinct features (e.g., as exhibited by groups of distinguishable identification fibers), taggant fiber counts (e.g., representative of the number of fibers in each group of distinguishable identification fibers), and/or a number of taggant fiber counts (e.g., as representative of a number of the of alternative fiber counts) to various components of the supply chain (e.g., to manufacturer 510). For example, laboratory 560 may assign, to manufacturer 510, a particular taggant fiber count (e.g., a taggant fiber count of ten) and/or particular combinations of cross-section size and shape (e.g., large and small Y-shaped identification fibers, and large and small D-shaped identification fibers).

When exhibited by identification fibers included within cellulose acetate fibers and corresponding fiber products produced by manufacturer 510, the assigned combinations of cross-section size and cross-section shape and/or taggant fiber counts may uniquely represent manufacturer 510 and may enable laboratory 560 (and additionally or alternatively, any other entity within environment 500) to identify manufacturer 510 as a source of the fiber products using any of the analytical techniques described above. Further, laboratory 560 (and additionally or alternatively, any other entity within environment 500) may also establish and maintain data records (e.g., within a centralized database implemented using the exemplary computing systems outlined below) that identify a correlation between the various supply chain components (e.g., manufacturer 510) and corresponding ones of the assigned distinct features, combinations of distinct features, taggant fiber counts, and/or number of taggant fiber counts.

The disclosed embodiments are, however, not limited to the assignment of exemplary taggant fiber counts, cross-section sizes, and cross-section shapes to manufacturer 510. In further embodiments, laboratory 560 may assign any additional or alternate set or combinations of sets of distinct features to uniquely identify manufacturer 510. For example, laboratory 560 may assign one or more cross-section sizes and/or one or more cross-section shapes to manufacturer 510. In other instances, laboratory 560 may assign one or more optical properties, and additionally or alternatively, one or more surface markings, to represent manufacturer 510, either alone or in combination with the assigned cross-section sizes and/or shapes. Additionally, and by way of example, laboratory 560 may also assign one or more taggant segment counts, taggant segment geometrical relationships, and/or taggant segment pointers to manufacturer 510.

In certain aspects, laboratory 560 may establish a centralized repository for data and data records (e.g., using any of the exemplary computing systems outlined below) that correlate the various supply chain components (e.g., manufacturer 510) to corresponding ones of taggant fiber counts, distinct features (e.g., cross-section size and/or shape, optical properties, surface markings, taggant segment counts, taggant segment geometrical relationships, and/or taggant segment pointers), combinations of the distinct features, and/or number of taggant fiber counts. Further, in other aspects, laboratory 560 may access the centralized repository and generate one or more reports specifying the taggant fiber counts, the distinct features, the combinations of distinct features, and/or the number of taggant fiber counts that uniquely identify at least one of the supply chain components (e.g., manufacturers). Laboratory 560 may, in some instances, generate the reports at predetermined intervals or in response to received requests (e.g., from requesting party 530, manufacturer 510, etc.), and may provide the generated reports to various parties and entities within environment 500 (e.g., across network 550).

In some embodiments, laboratory 560 may access the centralized repository to identify at least one supply chain component (e.g., manufacturer 510) associated with a distinct feature, combination of distinct features, taggant fiber counts, and/or number of taggant fiber counts determined by laboratory 560 (e.g., using any of the analytical techniques outlined above) and additionally or alternatively, obtained from any third party or other entity within environment 500. Further, and as described below, the centralized repository may enable laboratory 560 to determine whether proposed distinct features, combinations of distinct features, proposed taggant fiber counts, and/or proposed number of taggant fiber counts (e.g., as selected by manufacturer 510) are capable of uniquely representing fibers and fiber products of manufacturer 510 that are introduced into the supply chain.

In certain embodiments, laboratory 560 may receive proposed distinct features, combinations of distinct features (e.g., proposed cross-section sizes and/or cross-section shapes), proposed taggant fiber counts, and/or proposed number of taggant fiber counts from manufacturer 510. Laboratory 560 may, for example, compare the proposed distinct features, combinations of distinct features, proposed taggant fiber counts, and/or proposed number of taggant fiber counts against the established data records (e.g., within the centralized repository) to determine whether these proposed distinct features, combinations of distinct features, proposed taggant fiber counts, and/or proposed number of taggant fiber counts are capable of uniquely identifying manufacturer 510 (e.g., that the proposed distinct features, combinations of distinct features, proposed taggant fiber, pace that counts are assigned to no other supply chain components, such as another manufacturer). If the proposed distinct features, combinations of distinct features, proposed taggant fiber counts, and/or proposed number of taggant fiber counts could uniquely represent manufacturer 510, laboratory 560 may assign the proposed distinct features, combinations of distinct features, proposed taggant fiber counts, and/or proposed number of taggant fiber counts to manufacturer 510, update the data records to reflect the assignment, and provide confirmation of the assignment to manufacturer 510 (e.g., between computing systems of laboratory 560 and manufacturer 510 across network 550).

Alternatively, if laboratory 560 previously assigned the proposed distinct features, combinations of distinct features, proposed taggant fiber counts and/or proposed number of taggant fiber counts to another manufacturer (or the proposed distinct features, combinations of distinct features, proposed taggant fiber counts, and/or proposed number of taggant fiber counts are inappropriate to represent manufacturer 510), laboratory 560 may assign alternate distinct features, combinations of distinct features, alternate taggant fiber counts, and/or alternative number of taggant fiber counts to manufacturer 510, update the data records to reflect the alternate assignment, and provide confirmation of the alternate assignment to manufacturer 510. In other aspects, laboratory 560 could provide, to manufacturer 510, an indication of the assignment of the proposed distinct features, combinations of distinct features, taggant fiber counts, and/or number of taggant fiber counts to another manufacturer, and request that manufacturer 510 propose additional distinct features, combination of distinct features, taggant fiber counts, and/or number of taggant fiber counts for assignment by laboratory 560, as described above.

In certain aspects, upon confirmation of the assignment, manufacturer 510 may obtain and/or produce identification fibers that exhibit the assigned distinct features, combinations of distinct features, the taggant fiber counts, number of taggant fiber counts. For example, the obtained or produced identification fibers may include groups of distinguishable identification fibers that exhibit the assigned distinct features or combinations of distinct features and further, are present in the fiber counts that correspond to the assigned taggant fiber counts.

In other aspects, however, manufacturer 510 may further correlate the assigned distinct features, combinations of distinct features, the taggant fiber counts, and/or number of taggant fiber counts to one or more upstream components of the supply chain (e.g., a manufacture site, a manufacturing line, a production run, a production date, a bale) and/or various downstream components of the supply chain (e.g., a warehouse, a customer, a ship-to location, etc.). For example, manufacturer 510 may further specify fiber counts, in combination with the assigned distinct features, combinations of distinct features, taggant fiber counts, and/or number of taggant fiber counts uniquely represent a particular customer within the supply chain (e.g., customer 520).

The disclosed embodiments are, however, not limited to techniques that enable manufacturer 510 to correlate customer 520 to assigned distinct features, combinations of distinct features, taggant fiber counts, and/or number of taggant fiber counts. In further embodiments, manufacturer 510 may specify any additional or alternate taggant information (e.g., numbers of reference fibers, etc.) to represent other upstream or downstream supply components (or combinations thereof) in conjunction with the assigned distinct features, combinations of distinct features, taggant fiber counts, and/or number of taggant fiber counts.

In some aspects, while laboratory 560, or another entity, may maintain information linking manufacturer 510 to assigned distinct features, combinations of distinct features, taggant fiber counts, and/or number of taggant fiber counts manufacturer 510 may hold confidential additional taggant information (e.g., fiber counts, numbers of reference fibers, non-assigned taggant fiber counts, etc.) that links identification fibers, and thus fiber products produced by manufacturer 510, to other upstream and downstream components of the supply chain. The confidentiality of the additional taggant information may, in certain instances, enable manufacturer 510 to prevent laboratory 560 from identifying customers (e.g., customer 520), ship-to locations, warehouses, and other internal supply chain components (e.g., manufacture site or line, and production run or date) associated with manufacturer 510.

The embodiments described above identify particular combinations of taggant information that correlate to a specific component of a supply chain and, when exhibited in identification fibers of a sample, enable a laboratory, a manufacturer, or other entities to identify the specific supply chain component associated with the sample. One of ordinary skill in the art would, however, understand that the disclosed embodiments are not limited to the particular combinations or taggant information outlined above, and in further embodiments, specific supply chain components may be correlated with any additional or alternate physical, chemical, and/or optical characteristic exhibited by the identification fibers. Moreover, while not depicted in FIGS. 5A and 5B, one of skill in the art would understand that entities associated with environment 500 (shown and not shown) may employ one or more warehouses to store raw materials, intermediate products, final stage products, etc. in conducting operations consistent with disclosed embodiments.

Figure 6:
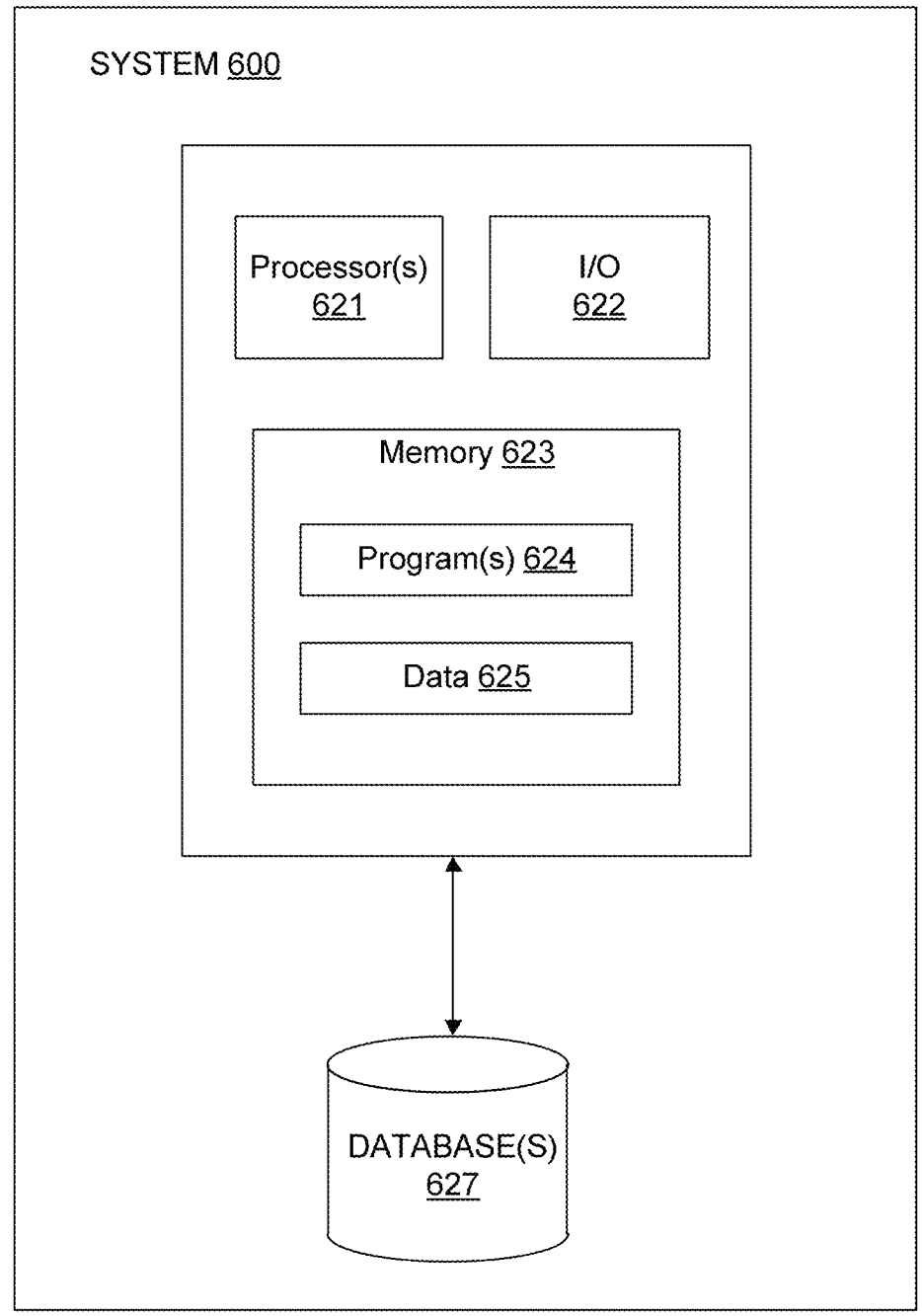
FIG. 6 illustrates a non-limiting example of a computing system used by one or more entities consistent with disclosed embodiments.

FIG. 6 illustrates a non-limiting example of a computing system 600 used by one or more entities consistent with disclosed embodiments. Variations of exemplary system 600 may be used by manufacturer 510 (e.g., as manufacturer system 512), customer 520, requesting party 530, and/or laboratory 560 (e.g., as laboratory system 562). In one embodiment, system 600 may comprise one or more processors 621, one or more input/output (I/O) devices 622, and one or more memories 623. In some embodiments, system 600 may take the form of a server, mainframe computer, or any combination of these components. In some embodiments, system 600 may take the form of a mobile computing device such as a smartphone, tablet, laptop computer, or any combination of these components. Alternatively, system 600 may be configured as a particular apparatus, embedded system, dedicated circuit, and the like based on the storage, execution, and/or implementation of the software instructions that perform one or more operations consistent with the disclosed embodiments.

Processor 621 may include one or more known processing devices, such as mobile device microprocessors or any various other processors. The disclosed embodiments are not limited to any type of processor(s) configured in system 600.

Memory 623 may include one or more storage devices configured to store instructions used by processor 624 to perform functions related to the disclosed embodiments. For example, memory 623 may be configured with one or more software instructions, such as program(s) 624 that may perform one or more operations consistent with disclosed embodiments when executed by processor 621. The disclosed embodiments are not limited to separate programs or computers configured to perform dedicated tasks. For example, memory 623 may include a single program 624 that performs the functions of system 600, or program 624 may comprise multiple programs. Memory 623 may also store data 625 that is used by one or more programs 612, such as correlation data mapping distinct features to one or more components of the supply chain information.

I/O devices 622 may be one or more devices configured to allow data to be received and/or transmitted by system 600. I/O devices 622 may include one or more digital and/or analog devices that allow components of environment 500 to communicate with other machines and devices, such as other components of environment 500. For example, I/O devices 622 may include a screen for displaying messages, distinct feature information, supply chain information, or providing other information to the user, such as an employee of manufacturer 510, customer 520, requesting party 530, and/or laboratory 560. I/O devices 622 may also include one or more digital and/or analog devices that allow a user to interact with system 600 such as a touch-sensitive area, keyboard, buttons, or microphones. I/O devices 622 may also include other components known in the art for interacting with a user.

The components of system 600 may be implemented in hardware, software, or a combination of both hardware and software, as will be apparent to those skilled in the art. For example, although one or more components of system 600 may be implemented as computer processing instructions, all or a portion of the functionality of system 600 may be implemented instead in dedicated electronics hardware.

System 600 may also be communicatively connected to one or more database(s) 627. System 600 may be communicatively connected to database(s) 627 through network 550. Database 627 may include one or more memory devices that store information and are accessed and/or managed through system 600. By way of example, database(s) 627 may include Oracle™ databases, Sybase™ databases, or other relational databases or non-relational databases, such as Hadoop sequence files, HBase, or Cassandra.

The databases or other files may include, for example, data and information related to distinct features, supply chain information, correlation data mapping the distinct features to the supply chain information, data indicative of distinct features assigned to the supply chain information, etc. For example, the databases and other files may include correlation data mapping the supply chain components to distinct features, combinations of distinct features, taggant fiber counts, number of taggant fiber counts, and/or numbers of reference fibers included in fiber samples, as described above. Further, by way of example, the databases and other files may also include distinct features, combinations of the distinct features, the taggant fiber counts, number of taggant fiber counts, and/or the numbers of reference fibers included in fiber samples assigned to supply chain components by laboratory 560, as outlined above.

Systems and methods of disclosed embodiments, however, are not limited to separate databases. In one aspect, system 600 may include database 627. Alternatively, database 627 may be located remotely from the system 600. Database 627 may include computing components (e.g., database management system, database server, etc.) configured to receive and process requests for data stored in memory devices of database(s) 627 and to provide data from database 627.

Although the above description has designated laboratory 560 as the entity assigning various taggants, in other aspects, manufacturer 510, customer 520, requesting party 530 or a third-party entity not shown may be the one assigning taggants for identification fibers. Furthermore, as seen from FIGS. 5A and 5B, although the description has focused on cellulose acetate tow and the black market associated with cigarette filters, the embodiments clearly apply to fibers of any material and any article subject to illicit trade.

Figure 7:
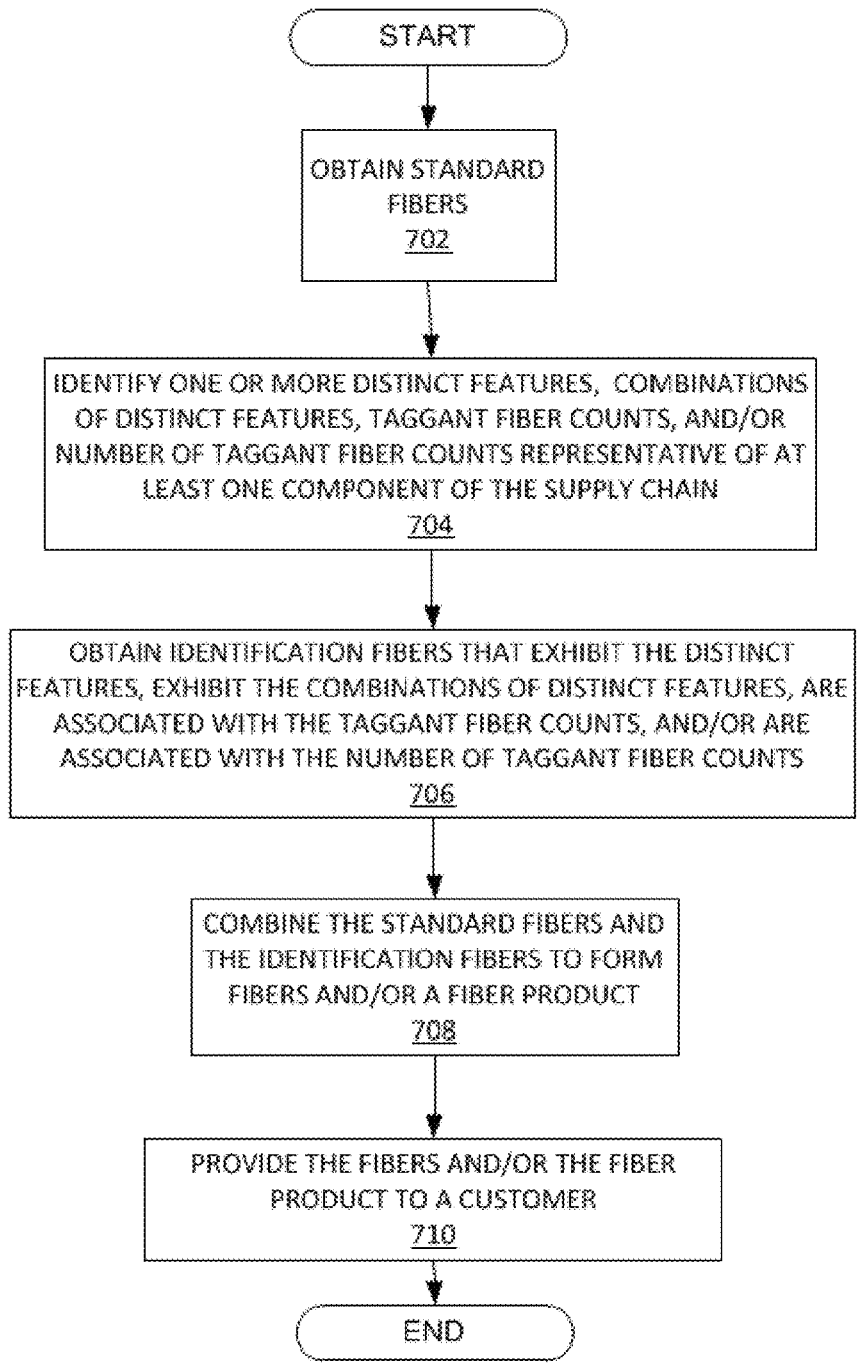
FIG. 7 illustrates a non-limiting example of a process for embedding supply chain information into fibers, consistent with disclosed embodiments.

FIG. 7 illustrates a non-limiting example of a process for embedding supply chain information into fibers, as seen and described above with respect to disclosed embodiments.

Figure 8:
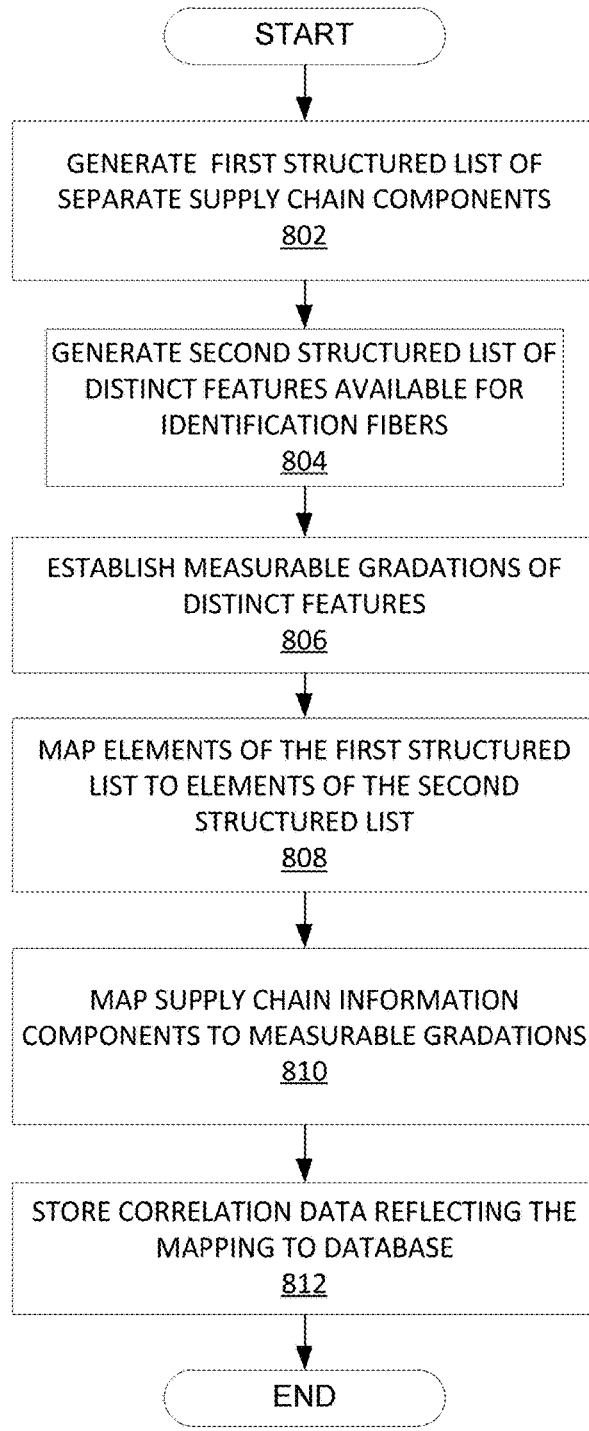
FIGS. 8 and 9 illustrate non-limiting examples of processes for generating correlation data, consistent with disclosed embodiments.

FIG. 8 illustrates a non-limiting example of a process for generating correlation data, as seen and described above with respect to disclosed embodiments. For example, as described in FIG. 8, manufacturer 510 (and additionally or alternatively, laboratory 560) may generate a first structured list of the supply chain components having one or more corresponding attributes, and may generate a second structured list of the distinct features (e.g., cross-section size and/or shape, optical properties, surface markings, taggant segment counts, taggant segment geometrical relationships, and/or taggant segment pointers). In some aspects, manufacturer 510 may establish measurable gradations of the distinct features included in the second structured list, and further, may map (i) elements of the first structured list to elements of the second structured list and (ii) the attributes of the supply chain components to the established measurable gradations. Manufacturer 510 may, in additional aspects, store correlation data (e.g., in database 627) reflecting the mapping of the elements of the first and second structured lists and the mapping of the supply attributes of the supply chain components to the established measurable gradations.

Figure 9:
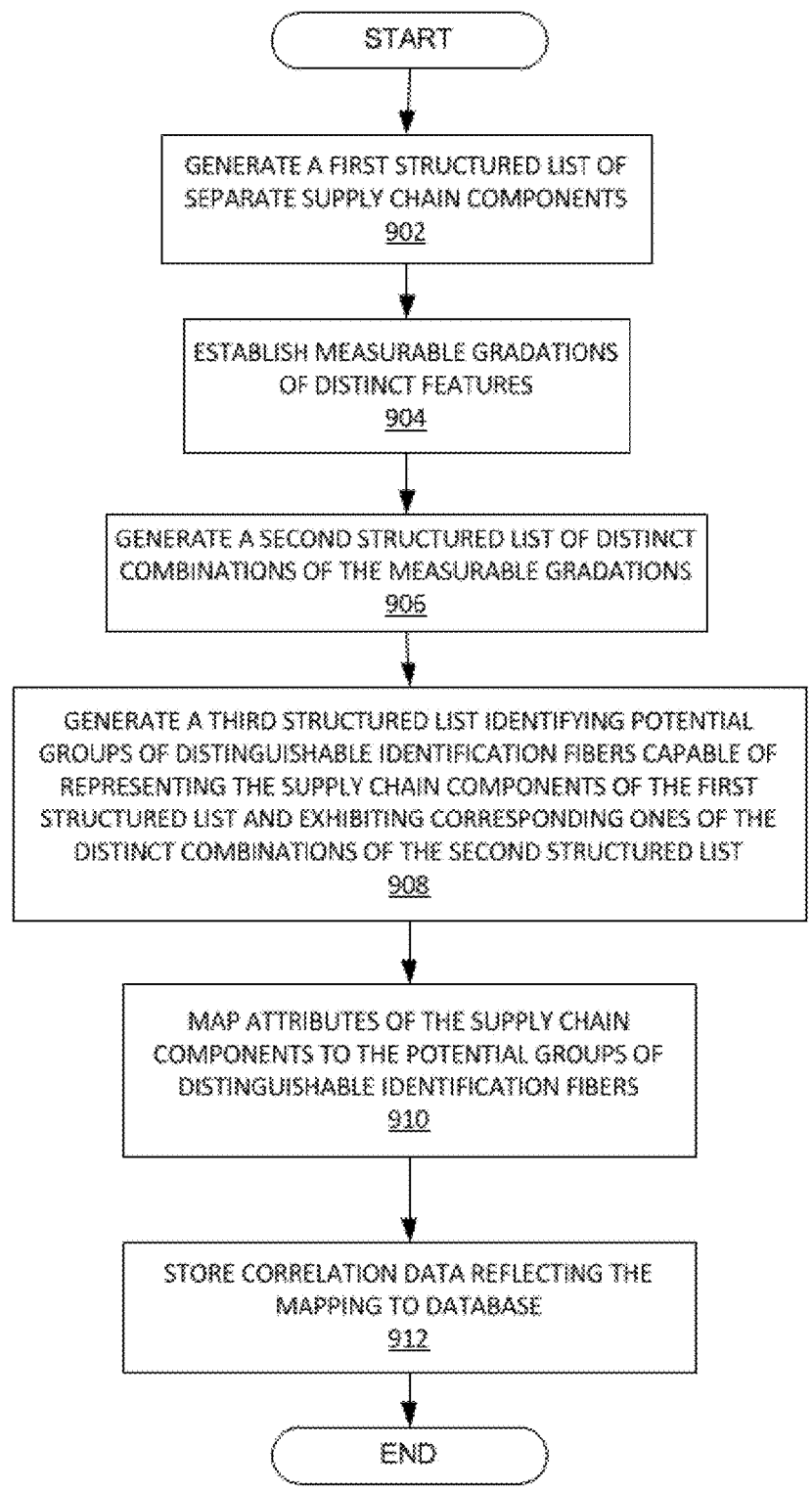

FIG. 9 illustrates an additional non-limiting example of a process for generating correlation data, as seen and described above with respect to disclosed embodiments. For example, as described in FIG. 9, laboratory 560 (and additionally or alternatively, manufacturer 510) may generate a first structured list of components of the supply chain. In one instance, the supply chain components may represent one or more corresponding attributes. Laboratory 560 may also establish measurable gradations in the distinct features (e.g., gradations in cross-section size and/or shape, optical properties, surface markings, taggant segment counts, taggant segment geometrical relationships, and/or taggant segment pointers), and may generate a second structured list comprising distinct combinations of the established measurable gradations of the distinct features. In some aspects, laboratory 560 may generate a third structured list identifying potential groups of the distinguishable identification fibers that exhibit corresponding ones of distinct features or combinations of the distinct features included within the third structured list. The potential groups of the distinguishable identification fibers may, for example, be capable of representing the supply chain components included within the first structured list. Laboratory 560 may further map the attributes of the supply chain components to the potential groups of the distinguishable identification fibers, and store correlation data (e.g., in database 627) reflecting the mapping of the attributes of the supply chain components to the potential groups of the distinguishable identification fibers.

Figure 10:
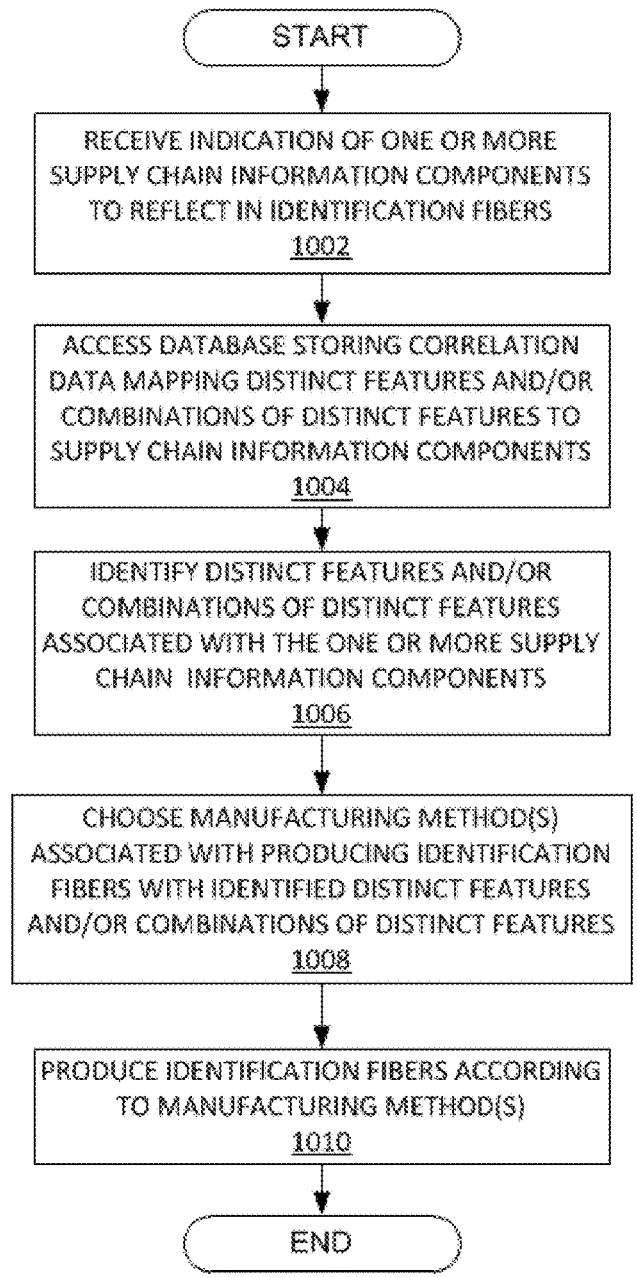
FIG. 10 illustrates a non-limiting example of a process for producing identification fibers, consistent with disclosed embodiments.

FIG. 10 illustrates a non-limiting example of a process for producing single-filament and/or multi-component identification fibers, as seen and described above with respect to disclosed embodiments.

Figure 11:
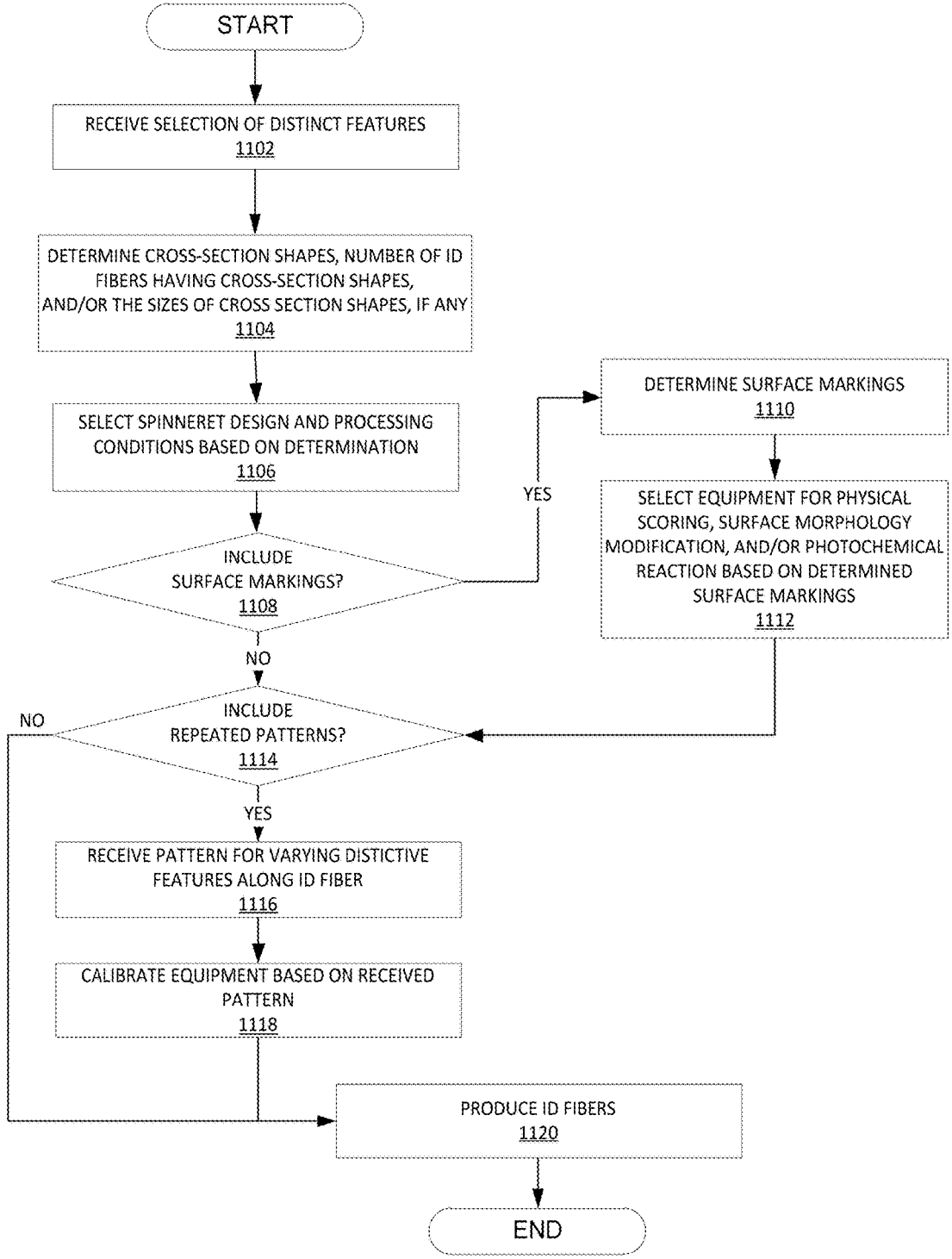
FIG. 11 illustrates a non-limiting example of a process for choosing one or more manufacturing methods for producing identification fibers, consistent with disclosed embodiments.

FIG. 11 illustrates a non-limiting example of a process for choosing one or more method for manufacturing single-filament and/or multi-component identification fibers, as seen and described above with respect to disclosed embodiments.

Figure 12:
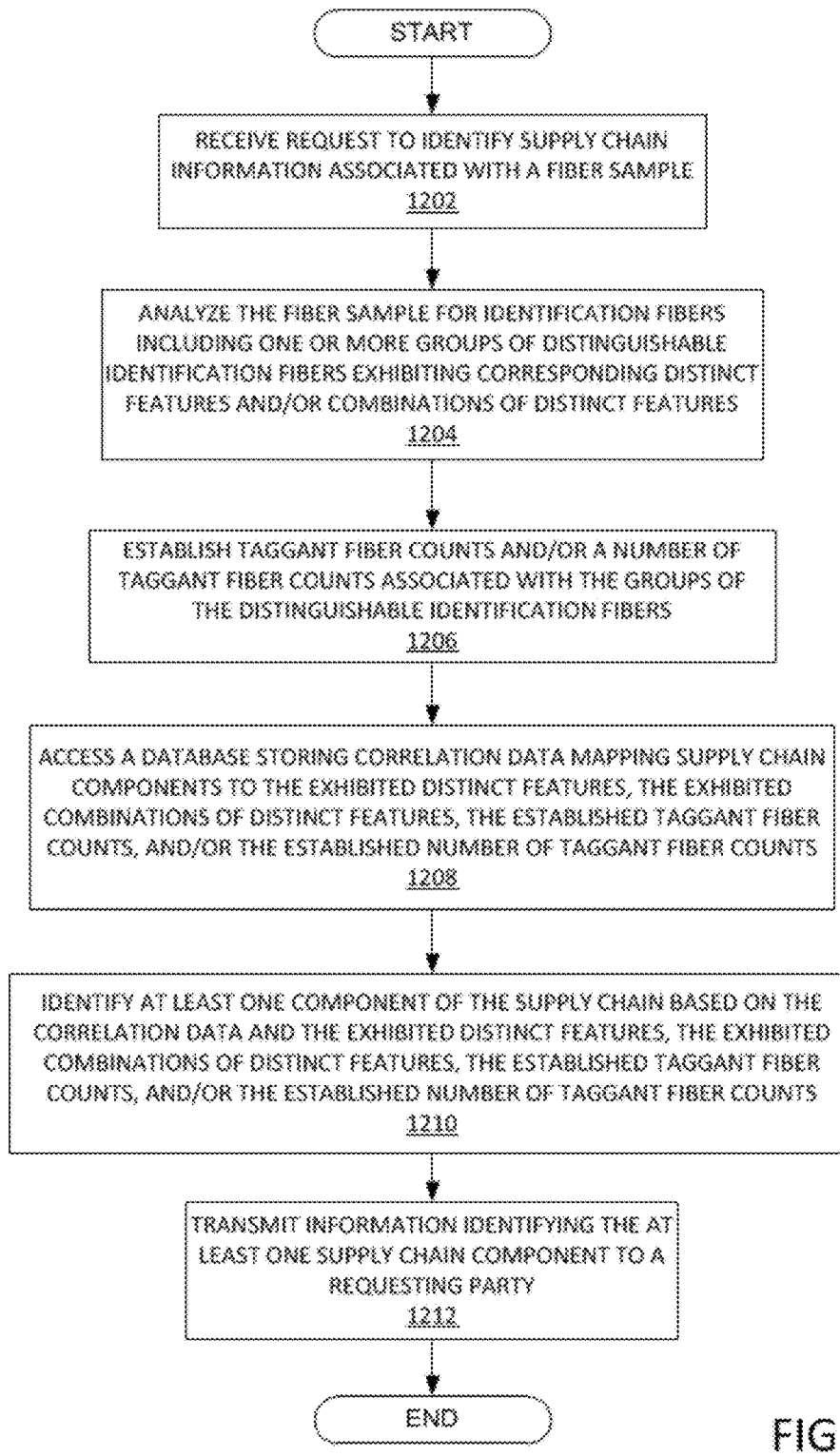
FIG. 12 illustrates a non-limiting example of a process for identifying supply chain information from a sample, consistent with disclosed embodiments.

FIG. 12 illustrates a non-limiting example of a process for identifying at least one supply chain component associated with a fiber sample, as seen and described above with respect to disclosed embodiments.

Figure 13:
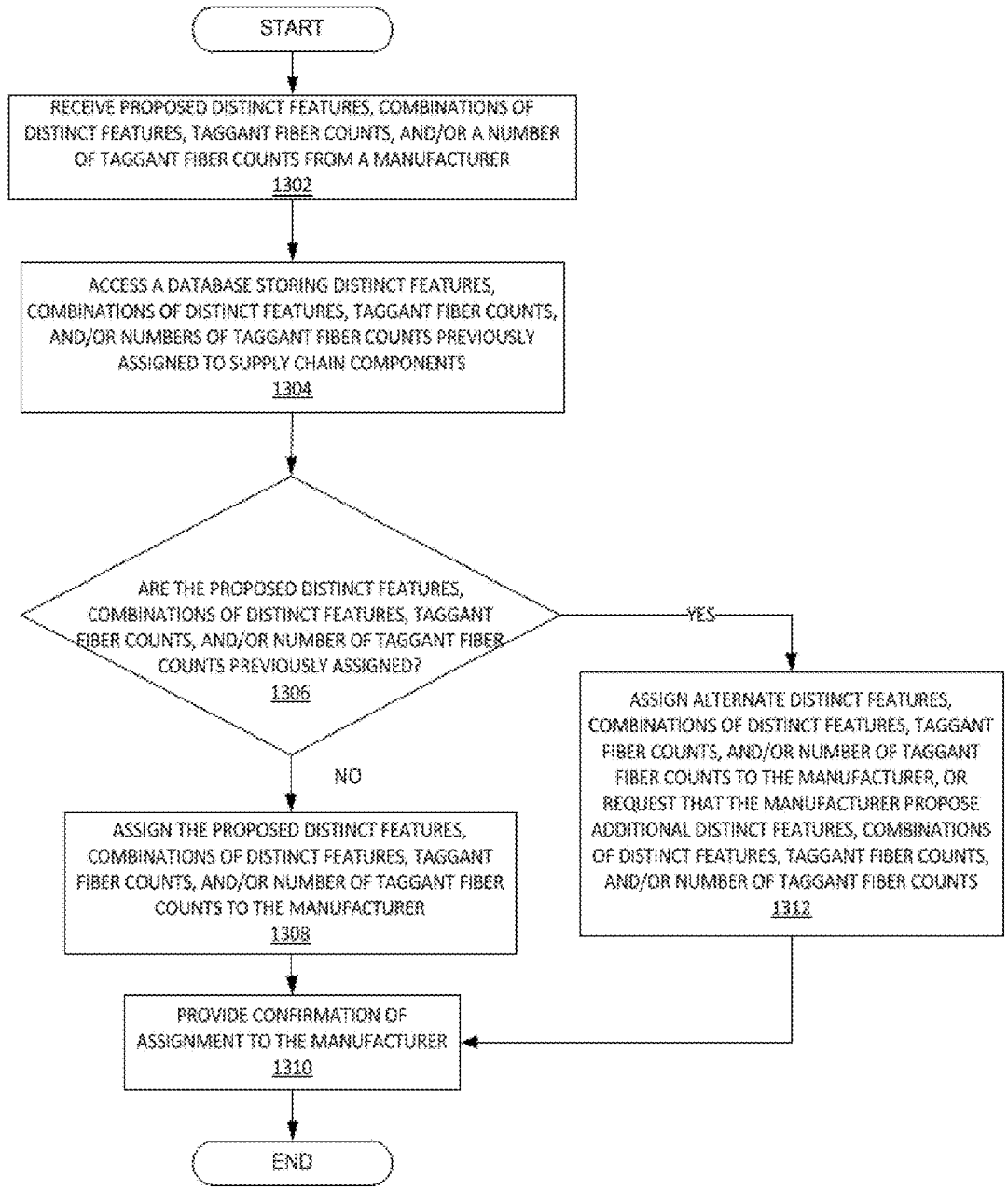
FIG. 13 illustrates a non-limiting example of a process for a non-assigning combinations of distinct features and taggant fiber counts to supply chain components, consistent with the disclosed embodiments.

FIG. 13 illustrates a non-limiting example of a process for assigning, to supply chain components, combinations of distinct features and taggant fiber counts that uniquely represent the supply chain components, as seen and described above with respect to disclosed embodiments.

Using the exemplary techniques described above, a manufacturer (e.g., manufacturer 510), a laboratory (e.g., laboratory 560), or other entity (e.g., a third-party entity) may regularly and reliably identify supply chain components associated with samples taken from illicitly traded cellulose acetate fibers or fiber products that incorporate the cellulose acetate fibers (e.g., as obtained by requesting party 530 from black market 540). The disclosed embodiments are, however, not limited to techniques that combat illicitly traded acetate fibers or fiber products. In further embodiments, manufacturer 510, laboratory 560, and/or another entity may perform any of the exemplary techniques outlined above to identify supply chain components associated with legitimately traded samples of cellulose acetate fibers and/or fiber products obtained from an authorized source within the supply chain (e.g., requesting party 530 and/or customer 520).

Listed below are non-limiting embodiments A1-A24.

A1. Fibers comprising identification fibers, wherein the identification fibers comprise multicomponent fibers, wherein each of the multicomponent fibers comprises 2 to 100 segments, wherein each of the identification fibers exhibits at least one distinct feature, wherein each of the multicomponent fibers exhibits the at least one distinct feature comprising one or more taggant segment counts, one or more taggant segment shapes, one or more taggant segment sizes, one or more taggant segment geometrical relationships, or one or more taggant segment pointers, wherein the identification fibers comprise one or more groups of distinguishable identification fibers, each group of the distinguishable identification fibers being formed by the identification fibers having the same distinct feature or a same combination of the distinct features, wherein a number of the identification fibers in each group of the distinguishable identification fibers is defined as a fiber count, wherein at least one of the fiber counts corresponds to a taggant fiber count; and wherein (i) the distinct features in each group of the distinguishable identification fibers and (ii) the one or more taggant fiber counts are representative of a code of the fibers.

A2. The fibers of embodiment A1, further comprising standard fibers and wherein the code is representative of at least one supply chain component of the fibers.

A3. The fibers of any of embodiments A1-A2, wherein each of the multicomponent fibers comprises 2 to 50 of the segments and wherein a number of the taggant fiber counts for each group of the distinguishable identification fibers ranges from 1 to 10.

A4. The fibers of any embodiments A1-A3, wherein the multicomponent fibers have an island and sea configuration, with the segments being formed by 1 to 50 of the islands and the sea.

A5. The fibers of any of embodiments A2-A4, wherein a number of the identification fibers ranges from 0.01 to 15 percent of a total number of the fibers.

A6. The fibers of any of embodiments A1-A5, wherein the at least one distinct feature comprises one or more taggant segment counts and wherein a number of the taggant segment counts ranges from 1 to 50.

A7. The fibers of any of embodiments A1-A6, wherein the at least one distinct feature comprises one or more the taggant segment geometrical relationships.

A8. The fibers of any of embodiments A1-A7, wherein the at least one distinct feature comprises one or more of the taggant segment pointers and wherein a number of the taggant segment pointers ranges from 1 to 50.

A9. The fibers of any of embodiments A1-A8, wherein the identification fibers comprises acrylic, modacrylic, aramid, nylon, polyester, polypropylene, rayon, polyacrylonitrile, polyethylene, PTFE, or cellulose acetate fibers.

A10. The fibers of any of embodiments A2-A9, wherein the standard fibers comprise cellulose acetate fibers.

A11. The fibers of any of embodiments A1-A10, wherein the at least one distinct feature further comprises one or more taggant optical properties, the taggant optical properties distinguishing the segments of the multicomponent fibers.

A12. The fibers of embodiment A11, wherein at least one of the segments in each of the multicomponent fibers comprises at least one of Cromophtal Red 2030 (CAS No. 84632-65-5), Copper Phthalocyanine (CAS No. 147-14-8), FD&C Yellow Lake No. 5 (CAS No. 12225-21-7), anatase titanium dioxide, rutile titanium dioxide, and mixed-phase titanium dioxide, whereby the segments exhibit the taggant optical properties.

A13. The fibers of any of embodiments A2-A12, wherein the at least one supply chain component comprises a manufacturer of the standard fibers, a manufacture site of the standard fibers, a manufacturing line of the standard fibers, a production run of the standard fibers, a production date of the standard fibers, a package of the standard fibers, a warehouse of the standard fibers, a customer of the standard fibers, a ship-to location of the standard fibers, a manufacturer of a fiber band comprising the fibers, a manufacturing site of the fiber band, a manufacturing line of the fiber band, a production run of the fiber band, a production date of the fiber band, a package of the fiber band, a warehouse of the fiber band, a customer of the fiber band, a ship-to location of the fiber band, a manufacturer of an article comprising the fibers, a manufacture site of the article, a manufacturing line of the article, a production run of the article, a production date of the article, a package of the article, a warehouse of the article, a customer of the article, or a ship-to location of the article.

A14. An acetate tow band comprising the fibers of any of embodiments A2-A13, wherein the standard fibers comprise cellulose acetate fibers.

A15. A method for making the identification fibers of embodiments A2-A13, wherein the method comprises spinning one or more polymers into the multicomponent fibers using one or more multicomponent spinpacks.

A16. The method of embodiment A15, wherein the distinguishable identification fibers comprising multicomponent fibers exhibiting two or more taggant segment counts are produced using a single one of the multicomponent spinpacks.

A17. The method of embodiment A15, wherein the distinct feature comprise one or more of the taggant optical properties, the segments exhibit the taggant optical properties, the method further comprising adding a substance to the one or more polymers prior to spinning of one or more of the multicomponent fibers, wherein the spinning comprises directing a feed stream to a hole for each of the segments, wherein the method further comprises selecting the feed stream for a portion of the segments from the one or more polymers that exhibit the taggant optical properties, wherein a number of the taggant optical properties ranges from 1 to 4.

A18. The method of embodiment 17, wherein a first polymer of the one or more polymers exhibits a first of the taggant optical properties, wherein a second polymer of the one or more polymers exhibits a second of the taggant optical properties, wherein the multicomponent fibers have an island and sea configuration, with the segments being formed by 1 to 50 of the islands and the sea, and wherein a first portion of the multicomponent fibers are produced with the islands comprising the first polymer and the sea comprising the second polymer and a second portion of the multicomponent fibers are produced with the islands comprising the second polymer and the sea comprising the first polymer.

A19. The method of embodiment A18, wherein the first portion of the multicomponent fibers and the second portion of the multicomponent fibers are produced within a single one of the multicomponent spinpacks.

A20. The method of any of embodiments A15-A19, wherein the code represents at least one supply chain component of a standard fiber, a fiber band, or an article and wherein the at least one supply chain component comprises a manufacturer of the standard fibers, a manufacture site of the standard fibers, a manufacturing line of the standard fibers, a production run of the standard fibers, a production date of the standard fibers, a package of the standard fibers, a warehouse of the standard fibers, a customer of the standard fibers, a ship-to location of the standard fibers, a manufacturer of a fiber band comprising the fibers, a manufacturing site of the fiber band, a manufacturing line of the fiber band, a production run of the fiber band, a production date of the fiber band, a package of the fiber band, a warehouse of the fiber band, a customer of the fiber band, a ship-to location of the fiber band, a manufacturer of an article comprising the fibers, a manufacture site of the article, a manufacturing line of the article, a production run of the article, a production date of the article, a package of the article, a warehouse of the article, a customer of the article, or a ship-to location of the article.

A21. A method of characterizing a fiber sample comprising (1) applying imaging technology to the fiber sample, wherein the fiber sample comprises the fibers of any of embodiments A2-A13, (2) detecting the groups of the distinguishable identification fibers, and (3) counting a number of each of the distinguishable identification fibers to determine the fiber counts of each group of the distinguishable identification fibers.

A22. The method of embodiment A21, further comprising correlating the distinct features in each group of the distinguishable identification fibers and the one or more taggant fiber counts to a database comprising manufacture specific taggants and determining the at least one supply chain component, wherein the at least one supply chain component comprises a manufacturer of the standard fibers a manufacture site of the standard fibers, a manufacturing line of the standard fibers, a production run of the standard fibers, a production date of the standard fibers, a package of the standard fibers, a warehouse of the standard fibers, a customer of the standard fibers, a ship-to location of the standard fibers, a manufacturer of a fiber band comprising the fibers, a manufacturing site of the fiber band, a manufacturing line of the fiber band, a production run of the fiber band, a production date of the fiber band, a package of the fiber band, a warehouse of the fiber band, a customer of the fiber band, a ship-to location of the fiber band, a manufacturer of an article comprising the fibers, a manufacture site of the article, a manufacturing line of the article, a production run of the article, a production date of the article, a package of the article, a warehouse of the article, a customer of the article, or a ship-to location of the article.

A23. The method of embodiment A22, wherein the at least one supply chain component comprises the manufacturer of the standard fibers and the customer of the standard fibers.

A24. The method of embodiment A22, wherein the at least one supply chain component comprises the manufacturer of the standard fibers and the ship-to location of the standard fibers.

Listed below are additional non-limiting embodiments B1-B53:

B1. A method for embedding supply chain information into fibers, the method comprising:
obtaining standard fibers;
obtaining identification fibers, the identification fibers comprising one or more groups of distinguishable identification fibers, each of the groups of distinguishable identification fibers exhibiting a corresponding distinct feature or a corresponding combination of distinct features, the identification fibers being associated with taggant fiber counts, and the taggant fiber counts being indicative of a number of the identification fibers in each of the groups; and
combining the standard fibers with the identification fibers, the distinct features, the combinations of distinct features, and/or the taggant fiber counts being representative of at least one component of a supply chain.

B2. The method of embodiment B1, wherein the distinct features comprise cross-section shapes, cross-section sizes, optical properties, and/or surface markings.

B3. The method of embodiment B2, wherein the combinations of distinct features exhibited by the groups comprise combinations of the cross-section shapes, the cross-section sizes, the optical properties, and/or the surface markings.

B4. The method of any of embodiments B1-B3, wherein the at least one supply chain component comprises a manufacturer, a manufacture site, a manufacturing line, a production run, a production date, a package, a bale, a warehouse, a customer, and/or a ship-to location.

B5. The method of any of embodiments B1-B4, comprising establishing a number of distinguishable identification fibers included within each of the groups as the fiber count and determining the corresponding taggant fiber count.

B6. The method of embodiment B5, wherein (i) the distinct features, (ii) the combinations of distinct features, (iii) the taggant fiber counts, and/or (iv) a number of taggant fiber counts are representative of the at least one supply chain component.

B7. The method of any of embodiments B1-B6, further comprising receiving, from a third party, information identifying (i) the cross-section shapes, (ii) the cross-section sizes, (iii) the optical properties, (iv) the surface markings, (v) the distinct features exhibited by the groups, (vi) the combinations of the distinct features exhibited by the groups, (vii) the taggant fiber counts, and/or (viii) the number of taggant fiber counts.

B8. The method of any of embodiments B1-B7, further comprising:
identifying proposed cross-section shapes, proposed cross-section sizes, proposed distinct features, proposed combinations of distinct features, proposed taggant fiber counts, and/or proposed number of taggant fiber counts to represent the at least one component of the supply chain;
providing the proposed cross-section shapes, the proposed cross-section sizes, the proposed distinct features, the proposed combinations of distinct features, the proposed taggant fiber counts, and/or the proposed number of taggant fiber counts to a third party; and
receiving, from the third party, information indicative of an assignment of the proposed cross-section shapes, the proposed cross-section sizes, the proposed distinct features, the proposed combinations of distinct features, the proposed taggant fiber counts, and/or the proposed number of taggant fiber counts to the at least one component of the supply chain.

B9. The method of any of embodiments B1-B7, further comprising
identifying proposed cross-section shapes, proposed cross-section sizes, proposed distinct features, proposed combinations of distinct features, proposed taggant fiber counts, and/or a proposed number of taggant fiber counts capable of representing the at least one component of the supply chain;
assigning the proposed cross-section shapes, the proposed cross-section sizes, the proposed distinct features, the proposed combinations of distinct features, the proposed taggant fiber counts, and/or the proposed number of taggant fiber counts to the at least one component of the supply chain.

B10. The method of any of embodiments B1-B7, further comprising:
identifying proposed cross-section shapes, proposed cross-section sizes, proposed optical properties, proposed surface markings, proposed distuinct features, proposed combinations of distinct features, proposed taggant fiber counts, and/or a proposed number of taggant fiber counts to represent the at least one component of the supply chain;
providing the proposed cross-section shapes, the proposed cross-section sizes, the proposed optical properties, the proposed surface markings, proposed distuinct features, the proposed combinations of distinct features, the proposed taggant fiber counts, and/or the proposed number of taggant fiber counts to a third party; and
receiving, from the third party, information indicative of an assignment of the proposed cross-section shapes, the proposed cross-section sizes, the proposed optical properties, the proposed surface markings, proposed distuinct features, the proposed combinations of distinct features, the proposed taggant fiber counts, and/or the proposed number of taggant fiber counts to the at least one component of the supply chain.

B11. The method of any of embodiments B1-B7, further comprising
identifying proposed cross-section shapes, proposed cross-section sizes, proposed optical properties, proposed surface markings, proposed distuinct features, proposed combinations of distinct features, proposed taggant fiber counts, and/or a proposed number of taggant fiber counts capable of representing the at least one component of the supply chain;
assigning the proposed cross-section shapes, the proposed cross-section sizes, the proposed optical properties, the proposed surface markings, proposed distuinct features, the proposed combinations of distinct features, the proposed taggant fiber counts, and/or the proposed number of taggant fiber counts to the at least one component of the supply chain.

B12. The method of any of embodiments B8-B11, wherein the at least one component of the supply chain corresponds to a manufacturer.

B13. The method of any of embodiments B1-B12, wherein the distinguishable identification fibers comprise at least one multi-component fiber, the at least one multi-component fiber comprising a plurality of segments.

B14. The method of embodiment B13, wherein the distinct features comprise taggant segment counts, taggant segment geometrical relationships, and/or taggant segment pointers exhibited by the at least one multi-component fiber.

B15. The method of embodiment B14, wherein the combinations of distinct features exhibited by the groups comprise combinations of the taggant segment counts, the taggant segment geometrical relationships, and/or the taggant segment pointers.

B16. The method of any of embodiments B13-B15, wherein the plurality of segments comprises at least one island and sea.

B17. The method of any of embodiments B13-B16, further comprising receiving, from a third party, information identifying the taggant segment counts, the taggant segment geometrical relationships, and/or the taggant segment pointers.

B18. The method of any of embodiments B13-B17, further comprising:
identifying proposed taggant segment counts, proposed taggant segment geometrical relationships, proposed taggant segment pointers, proposed distinct features, proposed combinations of distinct features, proposed taggant fiber counts, and/or a proposed number of taggant fiber counts to represent the at least one component of the supply chain;
providing the proposed taggant segment counts, the proposed taggant segment geometrical relationships, the proposed taggant segment pointers, the proposed distinct features, the proposed combinations of distinct features, the proposed taggant fiber counts, and/or the proposed number of taggant fiber counts to a third party; and
receiving, from the third party, information indicative of an assignment of the proposed taggant segment counts, the proposed taggant segment geometrical relationships, the proposed taggant segment pointers, the proposed distinct features, the proposed combinations of distinct features, the proposed taggant fiber counts, and/or the proposed number of taggant fiber counts to the at least one component of the supply chain.

B19. The method of any of embodiments B13-B17, further comprising
identifying proposed taggant segment counts, proposed taggant segment geometrical relationships, proposed taggant segment pointers, proposed distinct features, proposed combinations of distinct features, proposed taggant fiber counts, and/or a proposed number of taggant fiber counts capable of representing the at least one component of the supply chain;

assigning the proposed taggant segment counts, the proposed taggant segment geometrical relationships, the proposed taggant segment pointers, the proposed distinct features, the proposed combinations of distinct features, the proposed taggant fiber counts, and/or the proposed number of taggant fiber counts to the at least one component of the supply chain.

B20. The method of any of embodiments B1-B19, wherein the distinguishable identification fibers include reference fibers, the reference fibers having a corresponding reference cross-section shape and a corresponding reference cross-section size.

B21. The method of embodiment B20, wherein the reference cross-section size corresponds to an average effective diameter of a plurality of the reference fibers, the average effective diameter being larger than or smaller than the cross-section sizes associated with each of the distinct groups of the distinguishable identification fibers.

B22. The method of any of embodiments B19 and B21, wherein a sum of a number of the reference fibers and a number of the other distinguishable identification fibers corresponds to a predetermined value.

B23. The method of any of embodiment B1-B22, wherein a portion of the standard fibers and/or the identification fibers comprises cellulose acetate fibers.

B24. The method of embodiment B23, further comprising combining the standard fibers with the identification fibers to form a cellulose acetate tow band.

B25. The method of embodiment B24, further comprising producing a portion of a filter rod and/or cigarette filter from the cellulose acetate tow band.

B26. The method of any of embodiments B1-B25, further comprising combining the standard fibers with the identification fibers to form a portion of fabrics, other textile products, non-wovens, and/or absorbent products.

B27. The method of any of embodiments B1-B26, wherein obtaining the standard fibers comprises producing at least a portion of the standard fibers on a first fiber production process.

B28. The method of embodiment B27, wherein the first fiber production process comprises a dry-spinning process, a solution-spinning process, a melt-spinning process, an electro-spinning process, a gel-spinning process, a multi-component-spinning process, a melt-blowing process, and/or a solution-blowing process.

B29. The method of any of embodiments B27 and B28, wherein obtaining the identification fibers comprises receiving at least a portion of the identification fibers from a third party.

B30. The method of any of embodiments B27-B29, wherein obtaining the identification fibers comprises producing at least a portion of the identification fibers on a second fiber production process.

B31. The method of embodiment B30, wherein the second fiber production process comprises a dry-spinning process, a solution-spinning process, a melt-spinning process, an electro-spinning process, a gel-spinning process, a multi-component-spinning process, a melt-blowing process, and/or a solution-blowing process B32. The method of any of embodiments B30 and B31, wherein the first production process and the second fiber production process correspond to a common fiber production process.

B33. The method of any of embodiments B1-B32, further comprising generating correlation data mapping the distinct features, the combinations of distinct features, and/or the taggant fiber counts to the at least one supply chain component.

B34. The method of any of embodiments B1-B33, wherein generating the correlation data comprises mapping the distinct features, the combinations of distinct features, the taggant fiber counts, and/or a number of taggant fiber counts to the at least one supply chain component.

B35. The method of any of embodiments B1-B34, further comprising:
generating a first structured list of components of the supply chain, the supply chain components having one or more corresponding attributes;
establishing measurable gradations in the distinct features;
generating a second structured list comprising distinct combinations of the established measurable gradations of the distinct features;
generating a third structured list identifying potential groups of the distinguishable identification fibers that exhibit corresponding ones of the distinct combinations included within the third structured list, the potential groups of the distinguishable identification fibers being capable of representing the supply chain components included within the first structured list;
mapping the attributes of the supply chain components to the potential groups of the distinguishable identification fibers; and
storing correlation data reflecting the mapping of the attributes of the supply chain components to the potential groups of the distinguishable identification fibers.

B36. The method of embodiment B35, further comprising:
establishing a taggant fiber count for each of the potential groups; and
mapping the attributes of the supply chain components to the potential groups of the distinguishable identification fibers and the established taggant fiber count of each of the potential groups.

B37. The method of embodiment B35, further comprising:
mapping subsets of the attributes of the supply chain components to the potential groups of the distinguishable identification fibers; and
storing correlation data reflecting the mapping of the subsets of the attributes of the supply chain components to the potential groups of the distinguishable identification fibers.

B38. The method of any of embodiments B1-B34, further comprising:
generating a first structured list of the supply chain components, the supply chain components having one or more corresponding attributes;
generating a second structured list of the distinct features;
establishing measurable gradations of the distinct features included in the second structured list;
mapping elements of the first structured list to elements of the second structured list;
mapping the attributes of the supply chain components to the established measurable gradations; and
storing correlation data reflecting the mapping of the elements of the first and second structured lists and the mapping of the attributes of the supply chain components to the established measurable gradations.

B39. The method of embodiment B38, wherein the supply chain components comprise an indication of a manufacturer, a manufacture site, a manufacturing line, a production run, a production date, a package, a bale, a warehouse, a customer, and/or a ship-to location.

B40. The method of any of embodiments B38 and B39, wherein:
obtaining the identification fibers comprises producing at least a portion of the identification fibers; and
producing the portion of the identification fibers comprises:
receiving an indication of one or more supply chain components to reflect in the identification fibers;
accessing the stored correlation data;
identifying, from the stored correlation data, at least one applicable distinct feature mapped to the one or more selected supply chain information components;
selecting at least one manufacturing method associated with producing the identification fibers based on the at least one applicable distinct feature; and
producing the identification fibers according to the selected at least one manufacturing method.

B41. The method of embodiment B40, wherein selecting the at least one manufacturing method comprises:
determining whether an introduction of the at least one of applicable distinct feature of the identification fibers includes manipulating physical properties of the identification fibers;
identifying one or more manufacturing methods for the identification fibers based on the determination regarding the introduction of the at least one applicable distinct feature of the identification fibers; and
producing the identification fibers according to the identified one or more manufacturing methods.

B42. The method of embodiment B41, further comprising:
determining that the introduction of the at least one applicable distinct feature of the identification fibers includes at least a manipulation of physical properties; and
determining one or more cross-section shapes for the identification fibers.

B43. The method of embodiment B42, further comprising determining a number of identification fibers that exhibit each of the one or more cross-section shapes.

B44. The method of any of embodiments B42 and B43, further comprising:
determining a cross-section size for identification fibers exhibiting each of the one or more cross-section shapes.

B45. The method of any of embodiments B41-B44, further comprising:
determining that the introduction of the at least one applicable distinct feature of the identification fibers includes at least a manipulation of physical properties; and
determining a number of identification fibers that exhibit each of the one or more cross-section shapes.

B46. The method of any of embodiments B41-B45, further comprising:
determining that the introduction of the at least one applicable distinct feature of the identification fibers includes at least a manipulation of physical properties; and
determining one or more sizes exhibited by the identification fibers.

B47. The method of any of embodiments B41-B46, further comprising:
determining that the introduction of the at least one applicable distinct feature of the identification fibers includes at least a manipulation of physical properties; and
determining a number of identification fibers exhibiting each of the one or more cross-section sizes.

B48. The method of any of embodiments B41-B47, further comprising:
determining that the introduction of the at least one applicable distinct feature of the identification fibers includes at least a manipulation of physical properties;
determining that the manipulation of physical property comprises an introduction of surfaces markings on the identification fibers;
identifying a type of surface markings to introduce on the identification fibers; and
selecting at least one manufacturing method associated with producing the identified type of surface markings on the identification fibers.

B49. The method of embodiment B48, wherein the surface markings comprise notches in the identification fibers, a scoring or etching of the identification fibers, a morphological change on a surface of the identification fibers, barcodes printed on the identification fibers, and/or intermittent bleaching of the identification fibers to produce a pattern of optical properties.

B50. The method of embodiment B40, wherein selecting the at least one manufacturing method comprises:
determining whether an introduction of the at least one of applicable distinct feature of the identification fibers includes manipulating at least one optical property of the identification fibers;
identifying one or more manufacturing methods for the identification fibers based on the determination regarding the introduction of the at least one applicable distinct feature of the identification fibers; and
producing the identification fibers according to the identified one or more manufacturing methods.

B51. The method according to any of embodiments B1-B50, wherein at least one of the identification fibers comprises a monofilament, the monofilament being produced separately from at least a portion of the identification fibers and/or standard fibers.

B52. The method of embodiment B51, wherein the monofilament exhibits at least one surface marking, the at least one surface marking being representative of the at least one component of the supply chain.

B53. The method of embodiment B52, wherein the at least one surface marking comprises a bar code.

Listed below are additional non-limiting embodiments C1-C36:

C1. A method for identifying supply chain information from fiber samples, the method comprising:
analyzing a fiber sample for identification fibers, the identification fibers comprising one or more groups of distinguishable identification fibers, each of the groups of the distinguishable identification fibers exhibiting a corresponding distinct feature or a corresponding combination of distinct features;
establishing taggant fiber counts for the identification fibers, the taggant fiber counts being indicative of a number of the identification fibers in each of the groups;
accessing correlation data mapping components of a supply chain to the exhibited distinct features, the exhibited combinations of distinct features, and/or the established taggant fiber counts; and
based on the accessed correlation data, the exhibited distinct features, the exhibited combinations of distinct features, and/or the established taggant fiber counts, identifying at least one component of the supply chain associated with the fiber sample.

C2. The method of embodiment C1, wherein the fiber sample comprises standard fibers and the identification fibers.

C3. The method of any of embodiments C1 and C2, wherein the distinct features comprise cross-section shapes, cross-section sizes, optical properties, and/or surface markings of the distinguishable identification fibers.

C4. The method of embodiment C3, wherein the exhibited combinations of distinct features comprise distinct combinations of the cross-section-shapes, the cross-section sizes, the optical properties, and/or the surface markings.

C5. The method of any of embodiments C1-C4, wherein the at least one supply chain component comprises a manufacturer, a manufacture site, a manufacturing line, a production run, a production date, a package, a bale, a warehouse, a customer, and/or a ship-to location.

C6. The method of any of embodiments 1-C5, wherein the at least one identified supply chain component comprises a manufacturer, a manufacture site, a manufacturing line, a production run, a production date, a package, a bale, a warehouse, a customer, and/or a ship-to location.

C7. The method of any of embodiments C1-C6, wherein the distinguishable identification fibers comprise at least one multi-component fiber, the at least one multi-component fiber comprising a plurality of segments.

C8. The method of embodiment C7, wherein the distinct features comprise taggant segment counts, taggant segment geometrical relationships, and/or taggant segment pointers exhibited by the at least one multi-component fiber.

C9. The method of embodiment C8, wherein the combinations of distinct features exhibited by the distinct groups comprise combinations of the taggant segment counts, the taggant segment geometrical relationships, and/or the taggant segment pointers.

C10. The method of any of claims C7-C9, wherein the plurality of segments comprises at least one island and sea.

C11. The method of any of embodiments C1-C10, further comprising establishing a number of distinguishable identification fibers within each of the groups as the fiber count and determining the corresponding taggant fiber count.

C12. The method of embodiment C11, wherein
the correlation data maps the supply chain components to the exhibited distinct features, the exhibited combinations of distinct features, the taggant fiber counts, and/or the number of taggant fiber counts; and
the method further comprises identifying the at least one supply chain component associated with the fiber sample based on the accessed correlation data, and the exhibited distinct features, the exhibited combinations of distinct features, the established taggant fiber counts, and/or the number of taggant fiber counts.

C13. The method of any of embodiments C1-C12, wherein the distinguishable identification fibers comprise reference fibers, the reference fibers having a corresponding reference cross-section shape and a corresponding reference cross-section size.

C14. The method of embodiment C13, wherein:
analyzing the fiber sample comprises identifying the reference fibers within the fiber sample; and
the method further comprises establishing a number of the reference fibers identified within the fiber sample.

C15. The method of any of embodiments C13 and C14, wherein the reference cross-section size corresponds to an average effective diameter of at least a portion of the reference fibers, the effective diameter being larger than or smaller than cross-section sizes of the distinguishable identification fibers.

C16. The method of any of embodiments C13-C15, wherein analyzing the fiber sample comprises:
identifying the groups of distinguishable identification fibers within the fiber sample;
establishing a cross-section size of the distinguishable identification fibers included within each of the groups;
determining that the cross-section size of the distinguishable identification fibers included within a first one of the groups is larger than or smaller than the cross-section size of the distinguishable identification fibers within each of the other groups; and
based on the determination, establishing the distinguishable identification fibers included within the first group as the reference fibers.

C17. The method of any of embodiments C13-C15, wherein analyzing the fiber sample comprises:
identifying the groups of distinguishable identification fibers within the fiber sample;
establishing the number of the distinguishable identification fibers included within each of the groups;
determining that the number of the distinguishable identification fibers included within a first one of the groups exceeds the numbers of the distinguishable identification fibers within each of the other groups; and
based on the determination, establishing the distinguishable identification fibers included within the first distinct group as the reference fibers.

C18. The method of embodiment C17, wherein the determining comprises determining that the number of the distinguishable identification fibers included within the first group exceeds a sum of the numbers of the distinguishable identification fibers within the other groups.

C19. The method of embodiment C17, wherein the determining comprises determining that the number of the distinguishable identification fibers included within the first group exceeds a maximum of the numbers of the distinguishable identification fibers included within the other groups.

C20. The method of embodiment C19, wherein a ratio between (i) the maximum of the numbers of the distinguishable identification fibers included within the other groups and (ii) the number of the distinguishable identification fibers included within the first group is at least 2:1.

C21. The method of any of embodiments C13-C15, wherein:
the accessed correlation data maps the supply chain components to the exhibited distinct features, the exhibited combinations of distinct features, the established taggant fiber counts, the number of taggant fiber counts, and/or the number of the reference fibers included within the fiber sample; and
the method further comprises identifying the at least one component of the supply chain based on the accessed correlation data, and the exhibited distinct features, the exhibited combinations of distinct features, the taggant fiber counts, the number of taggant fiber counts, and/or the reference fiber count.

C22. The method of any of embodiments C1-C21, wherein the fiber sample comprises cellulose acetate fibers.

C23. The method of any of embodiments C1-C22, wherein the fiber sample comprises a portion of a cellulose acetate tow band.

C24. The method of any of embodiments C1-C23, wherein the fiber sample comprises a portion of a filter rod and/or a cigarette filter.

C25. The method of any of embodiments C1-C24, wherein the fiber sample comprises a portion of a textile product, a woven fabric, a non-woven fabric, and/or an absorbent product.

C26. The method of any of embodiments C1-C25, further comprising:
receiving a request to identify supply chain information associated with the fiber sample from a requesting entity; and
transmitting information identifying the at least one supply chain component to the requesting entity.

C27. The method of embodiment C26, wherein the requesting entity comprises a manufacturer, a customer, a governmental entity, a law enforcement entity, and/or a third-party requestor.

C28. The method of any of embodiments C26 and C27, wherein:
identifying the at least one supply chain component comprises identifying a plurality of supply chain components based on the correlation data, and the exhibited distinct features, the exhibited combinations of distinct features, the established taggant fiber counts, and/or a number of the taggant fiber counts; and
the transmitting comprises transmitting information identifying a subset of the plurality of supply chain components to the requesting entity.

C29. The method of any of embodiments C26-C28, wherein the transmitting further comprises transmitting information identifying a manufacturer to the requesting entity.

C30. The method of any of embodiments C26-C29, further comprising transmitting a portion of at least one of the exhibited distinct features, combinations of distinct features, or the established taggant fiber counts to the requesting entity.

C31. The method of any of embodiments C1-C30, wherein the analyzing comprises subjecting the fiber sample to an imaging technology.

C32. The method of embodiment C31, wherein the imaging technology comprises human visual inspection, microscopy, electron microscopy, confocal microscopy, florescence microscopy, and/or optical scanning.

C33. The method of embodiment C31, wherein the analyzing further comprises subjecting the fiber sample to light having a visible wavelength and/or an invisible wavelength.

C34. The method of embodiment C31, wherein the analyzing further comprises applying the imaging technology to the fiber sample in a direction transverse to a length of at least one of the fibers of the fiber sample.

C35. The method of embodiment C31, wherein the analyzing further comprises applying the imaging technology to the fiber sample in along a length of at least one of the fibers of the fiber sample.

C36. The method of embodiment C31, further comprising incorporating the fibers of the fiber sample into a solid matrix prior to subjecting the fiber sample to an imaging technology.

EXAMPLES

Sample Preparation for Fibers—Examples 1 and 2

The fibers were washed with ether solvent to remove the spin finish and dyed red. The fibers were then stretched across a frame and epoxied together to form a rigid rod of encapsulated fibers. The epoxied rod of fibers was cut perpendicular to the fiber axis to form a sample of 3 micron thickness. The sample was placed endwise on a microscope slide with cover plate and observed and photographed under a microscope.

Sample Preparation for Filter Rods—Examples 3-16

25 g of Electron Microscopy Sciences® Epo-Fix low viscosity resin with 3 g of hardener were mixed together. To the mixture was added 0.5 mL of dye mixture (14 g of ORCO® Orcocil Red B dye in 760 mL of ethanol). The mixture was stirred slowly until it was homogeneous. A 1.5-mL micro centrifugation tube was filled to ¾ capacity with the epoxy mixture. A 10 mm thick specimen from a filter rod was cut and placed on top of the epoxy. The filter was allowed to absorb the epoxy and the tube was placed in a tray and left in a controlled laboratory environment for up to 12 hours to allow the epoxy mixture to harden and embed the filter rod specimen. The specimen was removed from the tube by pitching the bottom of the tube with pliers.

The specimen was placed in a vice and a jeweler's saw was used to cut the specimen to a size suitable for the polishing chuck. The specimen was polished using the Allied MultiPrep polishing system with the following media and rotation speed sequence.
(1) 600 grit silicon carbide at 200 rpm
(2) 800 grit silicon carbide paper at 125 rpm
(3) Pan-B polishing mat with 6 micron diamond suspension at 100 rpm
(4) Pan-B polishing mat with 3 micron diamond suspension at 75 rpm
(5) Pan-B polishing mat with 1 micron diamond suspension at 50 rpm
(6) Final-A polishing mat with 0.5 micron diamond suspension at 30 rpm The diamond suspensions were in polycrystalline glycol. After each polishing step, the specimen was rinsed with water, dried under nitrogen, and visually inspected using a compound microscope to ensure that the scratches from the previous step were sufficiently removed.

Image analysis of the polished specimen was generated by the following technique. The polished specimen was placed on an Olympus MZ-130X85 motorized microscope stage. Either the 5× or 10× magnification setting was activated. BX61 STREAM Motion system software was opened. The "Define MIA scanning area with stage" function in the software's "Process Manager" was used to identify the top left and bottom right corners of the polished specimen. Each frame was focused as indicated by the software, the image collection process was run, and the data was saved. The software can be used to produce a single stitched image of the full filter rod cross-section.

Example 1

A cellulose acetate yarn was produced with three different filament sizes. A single 19-hole spinneret contained the three differently sized holes. The 7 medium-size holes represented 36.8% of the total number of spinneret holes. The 6 large size holes were 1.32 times the area of the medium-size holes and represented 31.6% of the spinneret holes. The 6 small size holes were 0.67 times the area of the medium-size holes and represented 31.6% of the spinneret holes.

The yarn was produced using the above-described spinneret with typical production conditions for acetate yarn. Multiple plies of the yarn were wound to produce a fiber band with several hundred filaments. The sample of the fibers was prepared according to the sample preparation method discussed above. The areas of 275 individual filament cross-sections were measured. The filament areas were grouped into bins to produce a filament area distribution.

The measured filament area distribution was fit with the sum of three independent Gaussian distributions using the Solver function in Microsoft EXCEL. The mean, standard deviation, and a scalar (amplitude factor) were determined for each of the three Gaussian distributions with the constraint that the three scalars summed to 1.0. Area measurements and statistical analysis for the fibers produced from small size holes, medium-size holes, and large size holes are given in Table 1 under columns labeled 1, 2, and 3 respectively. Pair-wise t-tests showed that the three Gaussian distributions are significantly different at the 99% confidence level. For each Gaussian distribution, 'n' was taken to be the corresponding scalar times the total number of filaments. This statistical analysis is summarized in Table 1.

These results show that filaments of different sizes can be produced from the same spinneret and can be recognized as significantly different by routine image analysis.

TABLE 1

Parameters and statistical comparison of optimized Gaussian distributions for Example 1

|  | 1 | 2 | 3 |
|---|---|---|---|
| Mean | 0.587 | 1.003 | 1.406 |
| Standard Deviation | 0.094 | 0.092 | 0.099 |
| Scalar | 0.364 | 0.335 | 0.301 |
| 'n' = scalar × 275 | 100 | 92 | 82 |
| Statistical comparison | #2 − #1 | #3 − #2 | #3 − #1 |
| t-statistic | 31.07 | 27.60 | 56.75 |
| Degrees of freedom | 190 | 172 | 180 |
| t-critical, 95% | 1.97 | 1.97 | 1.97 |
| t-critical, 99% | 2.60 | 2.60 | 2.60 |

Example 2

A cellulose acetate yarn was produced using a 19 hole spinneret with triangle, circle, and square holes. FIG. 1(a) gives a photomicrograph showing the cross-section shapes of the fibers.

Example 3

Taggant spinnerets were manufactured with the same hole pattern and hole size as is typically used to produce an acetate tow item with a nominal 3.0 filament denier and 32,000 total denier. Each taggant spinneret had 20 round holes and 20 square holes with the remaining holes all being triangles as typically used to make tri-lobal or "Y" cross section fibers. One taggant spinneret was installed on an acetate tow production line to produce a nominal 3.0 filament denier and 32,000 total denier band which corresponds to 11,160 filaments. The number of spinneret holes with taggant cross-section shapes and total number of spinneret holes is given in Table 2. The tow was produced, conditioned, and baled using standard manufacturing conditions.

Filter rods were produced from the tow on an AF4/KDF4 plug maker at a tape speed of 600 m/m. The rod length was 120 mm. The combined weight of the paper and glue was 91 mg/rod, and the plasticizer weight was 44 mg/rod. Table 3 shows the average tow weight, pressure drop, and circumference, as well as the standard deviation, for 30 filter rods of each Example. FIG. 1(b) shows a stitched image of a full filter rod cross-section with an expanded region; the filter rod was made with acetate tow from Example 3. All 40 taggant fibers were counted in the filter rod.

TABLE 2

The number of each of two taggant cross-section shapes in each Example

| Example | Taggant spinnerets | Number of holes | | | |
|---|---|---|---|---|---|
|  |  | Round | Square | Triangle | Total |
| 3 | 1 | 20 | 20 | 11,120 | 11,160 |
| 4 | 2 | 40 | 40 | 11,080 | 11,160 |
| 5 | 3 | 60 | 60 | 11,040 | 11,160 |
| 6 | 4 | 80 | 80 | 11,000 | 11,160 |
| 7 | 5 | 100 | 100 | 10,960 | 11,160 |
| 8 | 6 | 120 | 120 | 10,920 | 11,160 |
| 9 | 7 | 140 | 140 | 10,880 | 11,160 |
| 10 | 8 | 160 | 160 | 10,840 | 11,160 |
| 11 | 0 | 0 | 0 | 11,160 | 11,160 |

TABLE 3

Properties of filter rods comprising identification fibers

| Sample | Tow Weight, MG | | Pressure Drop, mm w.g. | | Circumference, mm | |
|---|---|---|---|---|---|---|
|  | Average | Std. Dev. | Average | Std. Dev. | Average | Std. Dev. |
| 3 | 550.6 | 5.5 | 316.5 | 6.4 | 24.27 | 0.04 |
| 4 | 554.8 | 4.5 | 316.5 | 5.6 | 24.28 | 0.05 |
| 5 | 555.1 | 7.0 | 317.7 | 7.2 | 24.28 | 0.04 |
| 6 | 558.4 | 5.7 | 314.3 | 5.9 | 24.29 | 0.03 |
| 7 | 552.6 | 5.9 | 315.1 | 7.1 | 24.29 | 0.05 |
| 8 | 550.5 | 5.2 | 315.6 | 6.1 | 24.28 | 0.04 |
| 9 | 556.2 | 6.5 | 318.9 | 6.2 | 24.29 | 0.04 |
| 10 | 553.3 | 4.9 | 311.5 | 5.2 | 24.29 | 0.03 |
| 11 | 552.8 | 5.3 | 320.0 | 7.2 | 24.28 | 0.04 |
| Average | 553.8 |  | 316.2 |  | 24.28 |  |
| Std. Dev. | 2.6 |  | 2.5 |  | 0.01 |  |

Examples 4-11

Example 3 was repeated using the number of taggant spinnerets and corresponding number of holes as given in Table 2. Example 11 used no taggant spinnerets. The number of taggant fibers were also counted in a filter rod made from Example 4 and all of the expected taggant fibers were detected.

The average weight, pressure drop, and circumference of the filter rods made using the acetate tow from each of the examples is given in Table 3. The average weight and pressure drop for each of the 9 Examples are within two-sigma of the grand averages which indicates that inclusion of the identification fibers produced using round and square spinneret holes did not have a statistically significant effect on the measured rod properties.

Example 12

An acetate yarn sample was produced with a single spinneret having 19 flattened round holes. The taggant yarn sample was wound onto a package. The yarn sample was withdrawn from its package and fed into a tow band prior to crimping. The cellulose acetate tow was a typical commercial, "Y" cross section tow item with a nominal 3.0 filament denier and 32,000 total denier.

The tow sample with the taggant yarn was produced, conditioned, and baled using the same manufacturing conditions as normally used for the tow item. Filter rods were produced from the tow on an AF4/KDF4 plug maker at a tape speed of 600 m/m. The rod length was 120 mm. The combined weight of the paper and glue was 91 mg/rod, and the plasticizer weight was 44 mg/rod.

A sample of a filter rod from each Example was prepared for analysis by the analytical procedure described above. All 19 taggant filaments included in the tow band were identified in the sample.

Examples 13-16

Example 12 was repeated using hexagon, pentagon, "D", and circle shaped spinneret holes, respectively. The yarns of Example 16 were dyed red. All 19 taggant filaments included in each tow band were identified in the sample of the corresponding filter rod.

Examples 12-16 show the ability to insert taggant yarns with different cross-section shapes into a tow band and successfully identify the taggant yarns in a filter rod.

Example 17

Two sets of forty polypropylene/polypropylene multicomponent fibers were produced wherein each multicomponent fiber comprised 19 islands in the sea. In the first set, the polypropylene of the islands were dyed blue while the polypropylene of the sea was undyed. In the second set, the polypropylene of the sea was dyed blue while the polypropylene of the islands were undyed. The islands were readily counted in each multicomponent fiber of both sets. The multicomponent fibers were drawn down in size and incorporated into an acetate tow band under normal conditions for producing acetate tow.

Filter rods were produced from the acetate tow band incorporating the multicomponent fibers. The multicomponent fibers were detected and counted (40) in both the acetate tow band and in the filter rod. Initial attempts to count the islands in the multicomponent fibers of the acetate tow band and filter rod were unsuccessful.

Other embodiments will be apparent to those skilled in the art from consideration of the specification and practice of the embodiments disclosed herein. It will be understood that variations and modifications can be effected within the spirit and scope of the disclosed embodiments. It is further intended that the specification and examples be considered as exemplary only, with a true scope and spirit of the disclosed embodiments being indicated by the following claims.

We claim:

1. A method of characterizing a fiber sample wherein the fibers comprise identification fibers and standard fibers, wherein the identification fibers comprise multicomponent fibers, wherein each of the multicomponent fibers comprise 2 to 100 segments, wherein each of the identification fibers exhibits at least one distinct feature, wherein each of the multicomponent fibers exhibits the at least one distinct feature comprising one or more taggant segment counts, one or more taggant segment shapes, one or more taggant segment sizes, one or more taggant segment geometrical relationships, or one or more taggant segment pointers, wherein the identification fibers consist of one or more groups of distinguishable identification fibers, each group of the distinguishable identification being formed by the identification fibers having the same distinct feature or a same combination of the distinct features, the method comprising,
(1) applying imaging technology to the fiber sample to generate stitched image data of the fiber sample,
(2) detecting the groups of the distinguishable identification fibers based on the stitched image data,
(3) determining a number of each of the distinguishable identification fibers for each detected group, wherein the number of the identification fibers in each detected group of the distinguishable identification fibers is defined as a fiber count, wherein at least one of the fiber counts corresponds to a taggant fiber count and wherein (i) the distinct features in each group of the distinguishable identification fibers and (ii) the one or more taggant fiber counts are representative of at least one supply chain component of the fiber sample, and (4) generating, based on the detection and determination, supply chain information correlating at least one group of the distinguishable fibers and at least one of the taggant fiber counts to the at least one supply chain component of the fiber sample.

2. The method of claim 1, wherein each of the identification fibers comprises 2 to 50 of the segments and wherein a number of the taggant fiber counts for each group of the distinguishable identification fibers ranges from 1 to 10.

3. The method of claim 1, wherein the multicomponent fibers have an island and sea configuration, with the segments being formed by 1 to 50 of the islands and the sea.

4. The method of claim 1, wherein the at least one distinct feature comprises one or more of the taggant segment counts and a number of the taggant segment counts ranges from 1 to 50.

5. The method of claim 1, wherein the at least one distinct feature comprises one or more of the taggant segment pointers and wherein a number of the taggant segment pointers ranges from 1 to 50.

6. The method of claim 1, wherein the identification fibers comprise acrylic, modacrylic, aramid, nylon, polyester, polypropylene, rayon, polyacrylonitrile, polyethylene, PTFE, or cellulose acetate fibers.

7. The method of claim 1, wherein the standard fibers comprise cellulose acetate fibers.

8. The method of claim 1, wherein the at least one distinct feature comprises one or more taggant optical properties, the taggant optical properties distinguishing the segments of the multicomponent fibers.

9. The method of claim 8, wherein at least one of the segments in each of the multicomponent fibers comprises at least one of Cromophtal Red 2030 (CAS No. 84632-65-5), Copper Phthalocyanine (CAS No. 147-14-8), FD&C Yellow Lake No. 5 (CAS No. 12225-21-7), anatase titanium dioxide, rutile titanium dioxide, and mixed-phase titanium dioxide.

10. The method of claim 1, wherein the at least one supply chain component comprises a manufacturer of the standard fibers a manufacture site of the standard fibers, a manufacture line of the standard fibers, a production run of the standard fibers, a production date of the standard fibers, a package of the standard fibers, a warehouse of the standard fibers, a customer of the standard fibers, a ship-to location of the standard fibers, a manufacturer of a fiber band comprising the fibers, a manufacture site of the fiber band, a manufacture line of the fiber band, a production run of the fiber band, a production date of the fiber band, a package of the fiber band, a warehouse of the fiber band, a customer of the fiber band, a ship-to location of the fiber band, a manufacturer of an article comprising the fibers, a manufacture site of the article, a manufacture line of the article, a production run of the article, a production date of the article, a package of the article, a warehouse of the article, a customer of the article, or a ship-to location of the article.

11. The method of claim 10, wherein the at least one supply chain component comprises the manufacturer of the standard fibers and the customer of the standard fibers.

12. The method of claim 10, wherein the at least one supply chain component comprises the manufacturer of the standard fibers and the ship-to location of the standard fibers.

13. The method of claim 1, wherein the standard fibers comprise cellulose acetate and the fiber sample comprises a portion of an acetate tow band, a portion of a filter rod and/or a cigarette filter.

14. The method of claim 13, wherein each of the identification fibers comprises 2 to 50 of the segments and wherein a number of the taggant fiber counts for each group of the distinguishable identification fibers ranges from 1 to 10.

15. The method of claim 13, wherein the multicomponent fibers have an island and sea configuration, with the segments being formed by 1 to 50 of the islands and the sea.

16. The method of claim 13, wherein the at least one distinct feature comprises one or more of the taggant segment counts and a number of the taggant segment counts ranges from 1 to 50.

17. The method of claim 13, wherein the at least one distinct feature comprises one or more taggant optical properties, the taggant optical properties distinguishing the segments of the multicomponent fibers.

18. The method of claim 17, wherein at least one of the segments in each of the multicomponent fibers comprises at least one of Cromophtal Red 2030 (CAS No. 84632-65-5), Copper Phthalocyanine (CAS No. 147-14-8), FD&C Yellow Lake No. 5 (CAS No. 12225-21-7), anatase titanium dioxide, rutile titanium dioxide, and mixed-phase titanium dioxide.

19. The method of claim 13, wherein the at least one supply chain component comprises the manufacturer of the acetate tow band and the customer of the acetate tow band.

20. The method of claim 13, wherein the at least one supply chain component comprises the manufacturer of the acetate tow band and the ship-to location of the acetate tow band.

* * * * *